(12) United States Patent
Hwang et al.

(10) Patent No.: US 7,941,279 B2
(45) Date of Patent: May 10, 2011

(54) SYSTEMS AND METHODS FOR ANALYZING NANOREPORTERS

(75) Inventors: Jenq-Neng Hwang, Bellevue, WA (US); Jeffrey D. Mitton, Bellevue, WA (US)

(73) Assignee: Nanostring Technologies, Inc., Seattle, WA (US)

(*) Notice: Subject to any disclaimer, the term of this patent is extended or adjusted under 35 U.S.C. 154(b) by 999 days.

(21) Appl. No.: 11/805,273

(22) Filed: May 21, 2007

(65) Prior Publication Data

US 2010/0262374 A1    Oct. 14, 2010

Related U.S. Application Data

(60) Provisional application No. 60/802,862, filed on May 22, 2006.

(51) Int. Cl.
*G06F 11/00* (2006.01)
(52) U.S. Cl. ......................................................... 702/19
(58) Field of Classification Search .................... 702/19, 702/182–185
See application file for complete search history.

(56) References Cited

U.S. PATENT DOCUMENTS

| | | | |
|---|---|---|---|
| 5,137,819 A | 8/1992 | Kilburn et al. |
| 5,202,247 A | 4/1993 | Kilburn et al. |
| 5,293,050 A | 3/1994 | Chapple-Sokol et al. |
| 5,354,707 A | 10/1994 | Chapple-Sokol et al. |
| 5,496,934 A | 3/1996 | Shoseyov et al. |
| 5,840,862 A | 11/1998 | Bensimon et al. |
| 6,001,983 A | 12/1999 | Benner |
| 6,054,327 A | 4/2000 | Bensimon et al. |
| 6,225,055 B1 | 5/2001 | Bensimon et al. |
| 6,265,153 B1 | 7/2001 | Bensimon et al. |
| 6,303,296 B1 | 10/2001 | Bensimon et al. |
| 6,344,319 B1 | 2/2002 | Bensimon et al. |
| 6,548,255 B2 | 4/2003 | Bensimon et al. |
| 2003/0157504 A1 | 8/2003 | Chee et al. |
| 2005/0014217 A1 | 1/2005 | Mattheakis et al. |
| 2008/0279442 A1* | 11/2008 | Den Boef et al. ............. 382/144 |
| 2010/0015607 A1 | 1/2010 | Geiss et al. |
| 2010/0261026 A1 | 10/2010 | Ferree et al. |

OTHER PUBLICATIONS

Asbury et al, "Trapping of DNA by dielectrophoresis", *Electrophoresis*, 23(16):2658-2666 (2002).
Asbury et al., "Trapping of DNA in Nonuniform Oscillating Electric Fields", *Biophys. J.*, 74:1024-1030 (1998).
Ashkin et al., "Observation of a single-beam gradient force optical trap for dielectric particles", *Opt. Lett.*, 11(5):288-290 (1986).

(Continued)

*Primary Examiner* — Edward Raymond
(74) *Attorney, Agent, or Firm* — Mintz Levin Cohn Ferris Glovsky and Popeo, P.C.; Ivor R. Elrifi, Esq.

(57) ABSTRACT

Methods, computers, and computer program products for detecting the presence of a probe within a sample overlayed on a substrate are provided. The probe comprises a plurality of spatially arranged labels. A data storage module stores a plurality of light images, where each light image has light from the sample at a corresponding wavelength range in a plurality of different wavelength ranges. A label identification module identifies a plurality of labels in the plurality of light images that are proximate to each other on the substrate. A spatial order of the plurality of labels determines a string sequence of the plurality of labels. A probe identification module determines whether the string sequence of the plurality of labels comprises a valid reporter sequence.

158 Claims, 21 Drawing Sheets

OTHER PUBLICATIONS

Figure 1A:
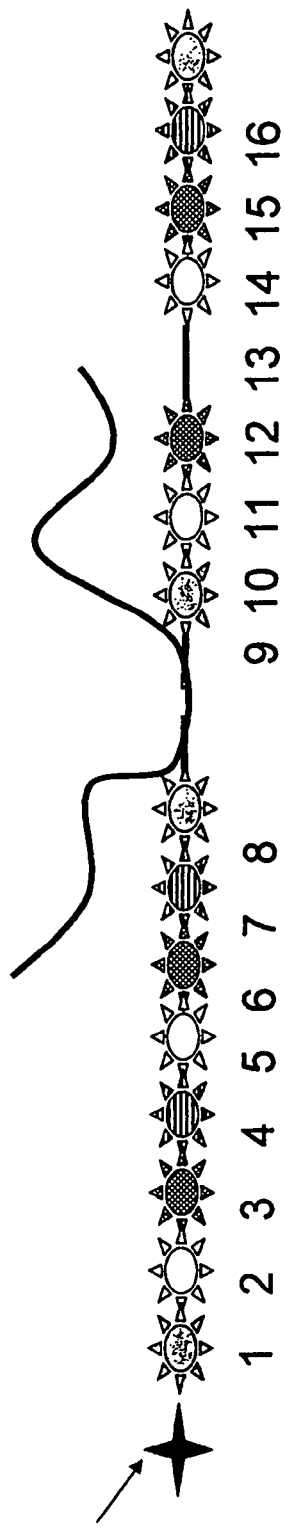

Ashkin et al., "Optical trapping and manipulation of single cells using infrared laser beams", *Nature*, 330:769-771 (1987).

Ashkin et al., "Optical Trapping and Manipulation of Viruses and Bacteria", *Science*, 235:1517-1520 (1987).

Bensimon et al., "Alignment and Sensitive Detection of DNA by a Moving Interface", *Science*, 265:2096-2098 (1994).

Blanchard et al., "Sequence to array: Probing the genome's secrets", *Nature Biotech.*, 14:1649 (1996).

Block et al., "Bead movement by single kinesin molecules studied with optical tweezers", *Nature*, 348:348-352 (1990).

Draghici, S., "Image processing", in *Data Analysis Tools for DNA Microarrays*, Chapman & Hall/CRC, New York, (2003) (36 pages).

Egholm et al., "Peptide Nucleic Acids (PNA). Oligonucleotide Analogues with an Achiral Peptide Backbone", *J. Am. Chem. Soc.*, 114:1895-1897 (1992).

Singer, B., "Alkyl Bases, Nucleosides, and Nucleotides. UV Spectral Characteristics and Acidic Dissociation Constants of 280 Alkyl Bases, Nucleosides, and Nucleotides", *Practical Handbook of Biochemistry and Molecular Biology*, Fasman, Ed., CRC Press, Inc., Boca Raton, FL, pp. 385-395 (1985).

Ferree et al., "Electrokinetic Stretching of Tethered DNA", *Biophys. J.*, 85(4):2539-2546 (2003).

Ferree et al., "The Hydrodynamics of DNA Electrophoretic Stretch and Relaxation in a Polymer Solution", *Biophys. J.*, 87(1):468-475 (2004).

Fortina et al., "Digital mRNA Profiling", *Nature Biotech.*, 26(3):293-294 (2008).

Geiss et al., "Direct multiplexed measurement of gene expression with color-coded probe pairs", *Nature Biotech.*, 26(3):317-325 (2008).

Goodchild, J., "Conjugates of Oligonucleotides and Modified Oligonucleotides: A Review of Their Synthesis and Properties", *Bioconjugate Chem.*, 1(3):165-187 (1990).

Grier, D. G., "A revolution in optical manipulation", *Nature*, 424:21-27 (2003).

Gryaznov et al., "Oligodeoxyribonucleotide N3'→P5' Phosphoramidates: Synthesis and Hybridization Properties", *J. Am. Chem. Soc.*, 116:3143-3144 (1994).

Guan et al., "Vectors that facilitate the expression and purification of foreign peptides in *Escherichia coli* by fusion to maltose-binding protein", *Gene*, 67:21-30 (1988).

Henegariu et al., "Rapid DNA Fiber Technique for Size Measurements of Linear and Circular DNA Probes", *BioTech.*, 31(2):246-250 (2001).

Hyrup et al., "Peptide nucleic acids (PNA): synthesis, properties and potential applications", *Bioorg. Med. Chem.*, 4(1):5-23 (1996).

Kabata et al., "Visualization of Single Molecules of RNA Polymerase Sliding along DNA", *Science*, 262(5139):1561-1563 (1993).

Kraus et al., "High-resolution comparative hybridization to combed DNA fibers", *Human Genet.*, 99:374-380 (1997).

Lockhart et al., "Expression monitoring by hybridization to high-density oligonucleotide arrays", *Nature Biotech.*, 14:1675-1680 (1996).

Mathews et al., "Expanded sequence dependence of thermodynamic parameters improves prediction of RNA secondary structure", *J. Mol. Biol.*, 288:911-940 (1999).

Matsuura et al., "One-End Immobilization of Individual DNA Molecules on a Functional Hydrophobic Glass Surface", *J. Biomol. Struct. Dyn.*, 20(3):429-436 (2002).

Matsuura et al., "Real-time observation of a single DNA digestion by λ exonuclease under a fluorescence microscope field", *Nucl. Acids Res.*, 29(16):E79 (2001).

Michalet et al., "Dynamic Molecular Combing: Stretching the Whole Human Genome for High-Resolution Studies", *Science*, 277:1518-1523 (1997).

Otobe et al., "Behavior of DNA fibers stretched by precise meniscus motion control", *Nucl. Acids Res.*, 29(22):E109 (2001).

Park et al., "Automatic Microarray Image Segmentation Based on Watershed Transformation", *Proceedings of the 17th International Conference on Pattern Recognition*, 3:786-789 (2004).

Pease et al., "Light-generated oligonucleotide arrays for rapid DNA sequence analysis", *Proc. Natl. Acad. Sci. U.S.A.*, 91:5022-5026 (1994).

Perkins et al., "Relaxation of a Single DNA Molecule Observed by Optical Microscopy", *Science*, 264:822-826 (1994).

Perry-O'Keefe et al., "Peptide nucleic acid pre-gel hybridization: an alternative to southern hybridization", *Proc. Natl. Acad. Sci. U.S.A.*, 93:14670-14675 (1996).

Schena et al., Quantitative Monitoring of Gene Expression Patterns with a Complementary DNA Microarray *Science*, 270:467-470 (1995).

Simmons et al., "Quantitative Measurements of Force and Displacement Using an Optical Trap", *Biophys. J.*, 70:1813-1822 (1996).

Smith, D. B., "Purification of Glutathione S-Transferase Fusion Proteins", *Meth. Mol. Cell Biol.*, 4:220-229 (1993).

Smith, G., Statistical Reasoning, 3rd Ed., Allyn and Bacon, Ed., Boston, pp. 724-730 (1991).

Stigter et al., "Theory for the Hydrodynamic and Electrophoretic Stretch of Tethered B-DNA", *Biophys. J.*, 75(3):1197-1210 (1998).

Tomme et al., "An internal cellulose-binding domain mediates adsorption of an engineered bifunctional xylanase/cellulase", *Protein Eng.*, 7(1):117-123 (1994).

Uhlman et al., "Antisense Oligonucleotides: A New Therapeutic Principle", *Chem. Rev.*, 90(4):544-584 (1990).

Vincent et al., "Watersheds in Digital Spaces: An Efficient Algorithm Based on Immersion Simulations", *IEEE Transactions on Pattern Analysis and Machine Intelligence*, 13(6):583-598 (1991).

Yokota et al., "A new method for straightening DNA molecules for optical restriction mapping", *Nucl. Acids Res.*, 25(5):1064-1070 (1997).

Zimmermann et al., "DNA stretching on functionalized gold surfaces", *Nucl. Acids Res.*, 22(3):492-497 (1994).

Zuker, M., "Mfold web server for nucleic acid folding and hybridization prediction", *Nucl. Acids Res.*, 31(13):3406-3415 (2003).

\* cited by examiner

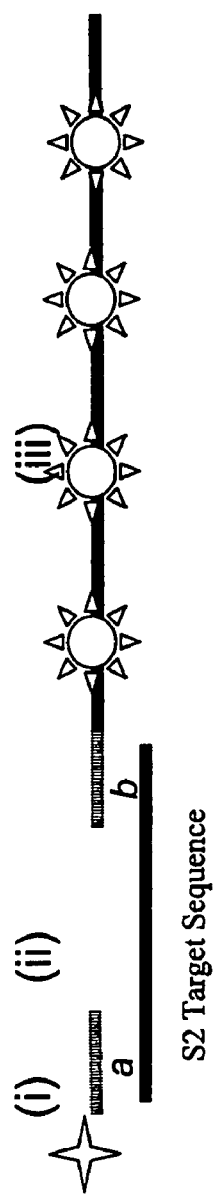
Figure 6A
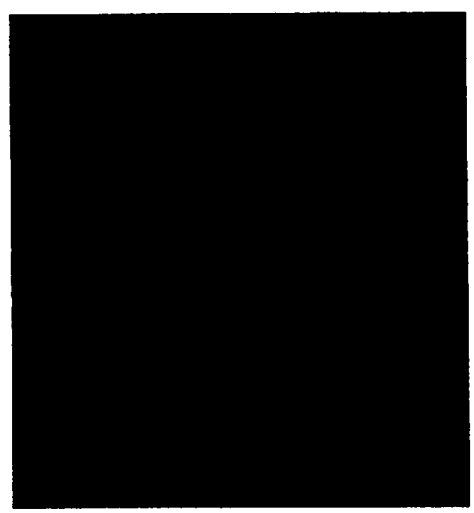
Figure 6D
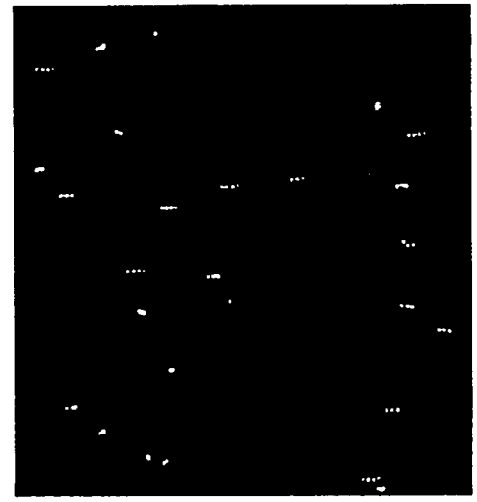
Figure 6C
Figure 6B

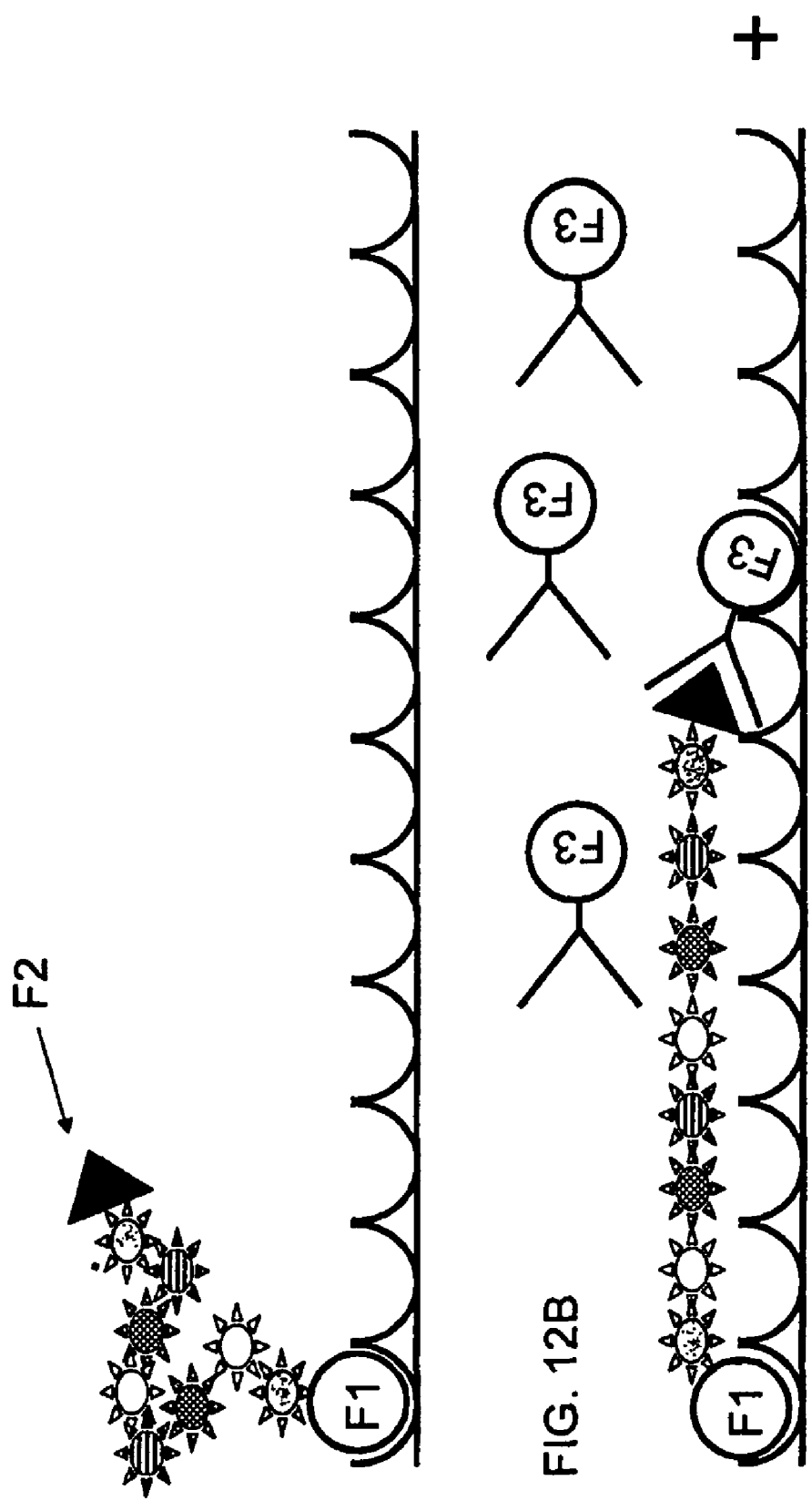

SYSTEMS AND METHODS FOR ANALYZING NANOREPORTERS

This application claims the benefit under 35 U.S.C. §119 (e) of U.S. Provisional Application No. 60/802,862 filed May 22, 2006, which is incorporated herein by reference in its entirety.

1. FIELD OF THE INVENTION

The present invention relates to compositions and methods for detection and quantification of individual target molecules in biomolecular samples. In particular, the invention relates to coded, labeled reporter molecules, referred to herein as labeled "nanoreporters," that are capable of binding individual target molecules. Through the nanoreporters' label codes, the binding of the nanoreporters to target molecules results in the identification of the target molecules. Methods of making and using such nanoreporters are also provided. The nanoreporters can be used in diagnostic, prognostic, quality control and screening applications.

2. BACKGROUND OF THE INVENTION

Although all cells in the human body contain the same genetic material, the same genes are not active in all of those cells. Alterations in gene expression patterns can have profound effects on biological functions. These variations in gene expression are at the core of altered physiologic and pathologic processes. Therefore, identifying and quantifying the expression of genes in normal cells compared to diseased cells can aid the discovery of new drug and diagnostic targets.

Nucleic acids can be detected and quantified based on their specific polynucleotide sequences. The basic principle underlying existing methods of detection and quantification is the hybridization of a labeled complementary probe sequence to a target sequence of interest in a sample. The formation of a duplex indicates the presence of the target sequence in the sample and the degree of duplex formation, as measured by the amount of label incorporated in it, is proportional to the amount of the target sequence.

This technique, called molecular hybridization, has been a useful tool for identifying and analyzing specific nucleic acid sequences in complex mixtures. This technique has been used in diagnostics, for example, to detect nucleic acid sequences of various microbes in biological samples. In addition, hybridization techniques have been used to map genetic differences or polymorphisms between individuals. Furthermore, these techniques have been used to monitor changes in gene expression in different populations of cells or in cells treated with different agents.

In the past, only a few genes could be detected in a complex sample at one time. Within the past decade, several technologies have made it possible to monitor the expression level of a large number of transcripts within a cell at any one time (see, e.g., Schena et al., 1995, Science 270: 467-470; Lockhart et al., 1996, Nature Biotechnology 14: 1675-1680; Blanchard et al., 1996, Nature Biotechnology 14:1649). In organisms for which most or all of the genome is known, it is possible to analyze the transcripts of large numbers of the genes within the cell. Most of these technologies employ DNA microarrays, devices that consist of thousands of immobilized DNA sequences present on a miniaturized surface that have made this process more efficient. Using a microarray, it is possible in a single experiment to detect the presence or absence of thousands of genes in a biological sample. This allows researchers to simultaneously perform several diagnostic tests on one sample, or to observe expression level changes in thousands of genes in one experiment. Generally, microarrays are prepared by binding DNA sequences to a surface such as a nylon membrane or glass slide at precisely defined locations on a grid. Then nucleic acids in a biological sample are labeled and hybridized to the array. The labeled sample DNA marks the exact position on the array where hybridization occurs, allowing automatic detection.

Unfortunately, despite the miniaturization of array formats, this method still requires significant amounts of the biological sample. However, in several cases, such as biopsies of diseased tissues or samples of a discrete cell type, the biological sample is in limited supply. In addition, the kinetics of hybridization on the surface of a microarray is less efficient than hybridization in small amounts of aqueous solution. Moreover, while methods exists to estimate the amount of nucleic acid present in a sample based on microarray hybridization result, microarray technology thus far does not allow for detection of target molecules on an individual level, nor are there microarray-based methods for directly quantifying the amount of target molecule in a given sample.

Thus, there exists a need for accurate and sensitive detection, identification and quantification of target molecules in complex mixtures.

Discussion or citation of a reference herein shall not be construed as an admission that such reference is prior art to the present invention.

3. SUMMARY OF THE INVENTION

One aspect of the present invention provides a computer program product comprising a computer readable storage medium and a computer program mechanism embedded therein. The computer program mechanism is for detecting the presence of a probe within a sample overlayed on a substrate. The probe comprises a plurality of spatially arranged labels. The computer program mechanism comprises a data storage module, a label identification module, and a probe identification module. The data storage module comprises instructions for storing a plurality of light images. Each light image in the plurality of light images is for light received from the sample at a wavelength range in a plurality of different wavelength ranges. The label identification module comprises instructions for identifying a plurality of labels, in the plurality of light images, that are proximate to each other on the substrate. A spatial order of the plurality of labels determines a string sequence of the plurality of labels. The probe identification module comprises instructions for determining whether the string sequence of the plurality of labels comprises a valid reporter sequence. When the string sequence of the plurality of labels is confirmed as a valid reporter sequence, the plurality of labels is deemed to be the probe. When the string sequence of the plurality of labels is not confirmed as a valid reporter sequence, the plurality of labels is deemed to not be the probe.

In some embodiments, a first label in the plurality of labels is associated with a first position on the substrate that emits light in a first wavelength range in the plurality of different wavelength ranges. Further, a second label in the plurality of labels is associated with a second position on the substrate that emits light in a second wavelength range in the plurality of different wavelength ranges. In some embodiments, a portion of the first wavelength range overlaps with a portion of the second wavelength range. In some embodiments, no part of the first wavelength range overlaps with any part of the second wavelength range. In some embodiments, each label in the plurality of labels is associated with a position on the substrate that emits more than a threshold amount of light in any one light image in the plurality of light images.

In some embodiments, the computer program mechanism further comprises a lookup table comprising a plurality of valid reporter sequences. In such embodiments, the probe identification module further comprises instructions for comparing the string sequence of the plurality of labels to valid reporter sequences in the lookup table. In some embodiments, the lookup table is dimensioned and configured to hold up to $4^4$, up to $7^4$, or up to $20^{20}$ different valid reporter sequences.

In some embodiments, the probe identification module further comprises instructions for storing the string sequence of the plurality of labels that is not confirmed as a valid reporter sequence. In some embodiments, the data storage module further comprises instructions for aligning a first light image to a second light image in the plurality of light images using a plurality of fiducials present on the substrate. In some embodiments, the position of the probe on the substrate is random. In some embodiments, the probe consists of a single molecule. In some embodiments, the probe comprises a molecular scaffold and each label in the plurality of labels represents a different position on the molecular scaffold. In some embodiments, each position on the molecular scaffold that is represented by a label is separated from a neighboring position on the scaffold by a spacer. In some embodiments, the probe comprises a single stranded deoxynucleic acid or ribonucleic acid scaffold and each label in the plurality of labels is represented by a dye laden single stranded deoxynucleic acid or ribonucleic acid sequence that hybridizes to a different position on the scaffold.

In some embodiments, the probe comprises a molecular scaffold having a first end and a second end. A target specific sequence is covalently attached to the first end. A binder sequence is covalently attached to the second end. In such embodiments, the probe is linearly arranged on the substrate through (i) the binding of the target specific sequence to a first molecular entity that is bound to a first position of the substrate and (ii) the binding of the binder sequence to a second molecular entity that is bound to a second position on the substrate. In some embodiments, the first molecular entity is a target (single stranded deoxynucleic acid or ribonucleic acid)-biotin complex and the second molecular entity is a predetermined (single stranded deoxynucleic acid or ribonucleic acid)-biotin complex.

In some embodiments, the label identification module further comprises instructions for identifying a plurality of candidate labels in the plurality of light images. This plurality of labels is a subset of the plurality of candidate labels that have been validated by the label identification module. In some embodiments, each candidate label in the plurality of candidate labels is associated with a position on the substrate that emits more than a threshold amount of light in any one light image in the plurality of light images. In some embodiments, the plurality of labels comprises a first candidate label that is associated with a first position on the substrate that emits light in a first wavelength range in the plurality of different wavelength ranges and a second candidate label that is associated with a second position on the substrate that emits light in a second wavelength range in the plurality of different wavelength ranges. In some embodiments, a portion of the first wavelength range overlaps with a portion of the second wavelength range. In some embodiments, the first wavelength range does not overlap with the second wavelength range. In some embodiments, the instructions for identifying the plurality of labels applies a first distance criterion between a centroid of a first candidate label and a centroid of a second candidate label in the plurality of candidate labels. The first distance criterion can be determined by a calculated distance between a first label and a second label in the probe. In some embodiments, the instructions for identifying the plurality of labels applies a second distance criterion between a centroid of the second candidate label and a centroid of a third candidate label in the plurality of candidate labels. The second distance criterion can be determined by a calculated distance between a second label and a third label in the probe. In some instances, the first distance criterion is the same as the second distance criterion. In other instances, the first distance criterion is different from the second distance criterion. In some embodiments, a value of the first distance criterion and a value of the second distance criterion contribute to determining whether the plurality of labels is the probe.

In some embodiments, the computer program mechanism further comprises a lookup table comprising a plurality of valid reporter sequences. In some embodiments, each valid reporter sequence in the plurality of valid reporter sequences comprises a first distance between a first pair of labels and a second distance between a second pair of labels. Further, the probe identification module comprises instructions for comparing the string sequence of the plurality of labels, the first distance criterion, and the second distance criterion, to valid reporter sequences in the lookup table.

In some embodiments, the instructions for identifying the plurality of labels applies an angle criterion to triplets of candidate labels in the plurality of candidate labels. In some embodiments, the instructions for identifying the plurality of labels comprises instructions for applying a model (e.g., linear regression) to select candidate labels in the plurality of candidate labels. In some embodiments, the label identification module further comprises instructions for verifying that a candidate label in the plurality of candidate labels satisfies a spot shape criterion. An example of a spot shape criterion is a match between an observed spot shape of the candidate label and the theoretical point spread of the diffraction limited point source light determined by a magnification of the candidate label. In some embodiments, the instructions for verifying that a candidate label in the plurality of candidate labels satisfies the spot shape criterion comprises instructions for performing point spread function modeling on the candidate label. In some embodiments, the instructions for verifying that a candidate label in the plurality of candidate labels satisfies the spot shape criterion comprises instructions for applying a spot segmentation algorithm to the candidate label. In some embodiments, the spot segmentation algorithm comprises a watershed transformation.

In some embodiments, the instructions for identifying the plurality of labels applies an absolute distance criterion between a centroid of a first terminal candidate label and a centroid of a second terminal candidate label in the plurality of candidate labels. In some embodiments, the instructions for identifying the plurality of labels comprises instructions for identifying a buffer zone around a portion of the substrate that has select candidate labels in the plurality of candidate labels, where there are no candidate labels in the buffer zone. In some embodiments, the plurality of labels are linearly arranged on the substrate (e.g., in the same linear orientation). In some embodiments, a linear orientation of each label in the plurality of labels is predetermined (e.g., by an application of an electrical current across the substrate or by an application of a fluid across the substrate, etc.). In some embodiments, each respective label in the plurality of labels occupies between 4 and 20 pixels, between 1 and 30 pixels, or between 4 and 100 pixels in a pixilated representation of the respective label in a light image in the plurality of light images.

In some embodiments, the label identification module further comprises instructions for identifying a first candidate label in the plurality of light images and instructions for identifying a second candidate label in the plurality of light images that is within a predetermined distance away from the first candidate label. In such embodiments, the plurality of labels comprises the first candidate label and the second candidate label.

In some embodiments, the plurality of different wavelength ranges consists of between two different wavelength ranges and six different wavelength ranges, or between two different wavelength ranges and twenty different wavelength ranges. In some embodiments, the plurality of labels comprises four or five labels. In some embodiments, the plurality of labels consists of between two labels and twenty labels.

In some embodiments, a first subset of the labels in the string sequence error check an identity of the labels in a second subset of the labels in the string sequence. In some embodiments, a first subset of labels in the string sequence are a checksum for a second subset of labels in the string sequence.

In some embodiments, the label identification module comprises instructions for repeating the instructions for identifying a plurality of labels a plurality of times. Each time the instructions for identifying a plurality of labels is repeated, a different plurality of labels is identified, in the plurality of light images, that are proximate to each other on the substrate. The probe identification module determines whether each of the different plurality of labels identified by the label identification module comprises a valid reporter sequence. For each different plurality of labels identified, the probe identification module deems the different plurality of labels to be a probe when the string sequence of the different plurality of labels is confirmed as a valid reporter sequence and deems the different plurality of labels to not be a probe when the string sequence of the different plurality of labels is not confirmed as a valid reporter sequence. In some embodiments, a plurality of probes is identified. In some embodiments, the plurality of probes consists of three or more probes. In some embodiments, the plurality of probes consists of ten or more probes. In some embodiments, the plurality of probes consists of less than 50 probes. In some embodiments, the probe identification module stores each type of probe identified. In some embodiments, the probe identification model stores each string sequence of each different plurality of labels that is not confirmed as a valid reporter sequence. In some embodiments, the probe identification model stores each string sequence of each different plurality of labels that is confirmed as a valid reporter sequence.

Another aspect of the invention provides a computer system for detecting the presence of a probe within a sample overlayed on a substrate. The probe comprises a plurality of spatially arranged labels. The computer system comprises a central processing unit and a memory, coupled to the central processing unit. The memory stores a data storage module, a label identification module, and a probe identification module. The data storage module comprises instructions for storing a plurality of light images. Each light image in the plurality of light images is for light received from the sample at a wavelength range in a plurality of different wavelength ranges. The label identification module comprises instructions for identifying a plurality of labels, in the plurality of light images, that are proximate to each other on the substrate. A spatial order of the plurality of labels determines a string sequence of the plurality of labels. The probe identification module comprises instructions for determining whether the string sequence of the plurality of labels comprises a valid reporter sequence. When the string sequence of the plurality of labels is confirmed as a valid reporter sequence, the plurality of labels is deemed to be the probe. When the string sequence of the plurality of labels is not confirmed as a valid reporter sequence, the plurality of labels is deemed to not be the probe.

Still another aspect of the invention comprises a system for detecting the presence of a probe within a sample overlayed on a substrate. The system comprises a light measuring mechanism, a data storage module, a label identification mechanism, and a probe identification mechanism. The light measuring mechanism measures a plurality of light images. Each light image in the plurality of light images is for light received from the sample at a wavelength range in a plurality of different wavelength ranges. The data storage module comprises instructions for storing the plurality of light images. The label identification mechanism identifies a plurality of labels in the plurality of light images that are proximate to each other on the substrate. A spatial order of the plurality of labels determines a string sequence of the plurality of labels. The probe identification mechanism determines whether the string sequence of the plurality of labels comprises a valid reporter sequence. When the string sequence of the plurality of labels is confirmed as a valid reporter sequence, the plurality of labels is deemed to be the probe. When the string sequence of the plurality of labels is not confirmed as a valid reporter sequence, the plurality of labels is deemed to not be the probe. In some embodiments, the system further comprises an illumination mechanism that illuminates the substrate. In some embodiments, the illumination mechanism comprises an excitation light source and a plurality of excitation filters. Each excitation filter in the plurality of excitation filters is used in a corresponding light image in the plurality of light images to confine the light source to a corresponding different spectral range when the corresponding light image is measured. In some embodiments, the light measuring mechanism comprises a plurality of measurement wavelength filters, where each measurement wavelength filter in the plurality of measurement wavelength filters is used in a corresponding light image in the plurality of light images to reject light not within a corresponding spectral range. In some embodiments, the light measuring mechanism comprises a photodetector that forms a detection signal in response to light emitted from the sample.

In some embodiments, the light measuring mechanism comprises a detector circuit addressed by the detection signal that measures light emitted from the sample overlayed on the substrate. In such embodiments, the light measuring mechanism further comprises an electronic memory for storing a plurality of label positions, where each label position in the plurality of label positions represents a label and each label position in the plurality of label positions originates more than a threshold amount of light. In some embodiments, the label identification mechanism identifies the plurality of labels that are proximate to each other from among the plurality of label positions stored in electronic memory. In some embodiments, the label identification mechanism comprises instructions for identifying a plurality of candidate labels in the plurality of light images and the plurality of labels is a subset of the plurality of candidate labels.

Yet another aspect of the invention provides methods for detecting the presence of a probe within a sample overlayed on a substrate. In this aspect of the invention, the probe comprises a plurality of spatially arranged labels. In one such method, a plurality of labels, in a plurality of light images, that are proximate to each other on the substrate is identified. The spatial order of the plurality of labels determines a string sequence of the plurality of labels. Each light image in the plurality of light images is for light received from the sample at a wavelength range in a plurality of different wavelength ranges. In the method, a determination is made as to whether the string sequence of the plurality of labels comprises a valid reporter sequence. When the string sequence of the plurality of labels is confirmed as a valid reporter sequence, the plurality of labels is deemed to be the probe. When the string sequence of the plurality of labels is not confirmed as a valid reporter sequence, the plurality of labels is deemed to not be the probe.

In some embodiments, the determining step comprises comparing the string sequence of the plurality of labels to valid reporter sequences in a lookup table. In some embodiments, the method further comprises storing the string sequence of the plurality of labels that is not confirmed as a valid reporter sequence. For instance, the string sequence can be stored in an electronic memory. In some embodiments, the method further comprises aligning a first light image to a second light image in the plurality of light images using a plurality of fiducials present on the substrate.

In some embodiments, the step of identifying a plurality of labels is repeated a plurality of times. Each time the step of identifying a plurality of labels is repeated, a different plurality of labels is identified, in the plurality of light images, that are proximate to each other on the substrate. In some embodiments, the method further comprises determining whether each of the different plurality of labels comprises a valid reporter sequence. Each different plurality of labels is deemed to be a probe when the string sequence of the different plurality of labels is confirmed as a valid reporter sequence. Furthermore, each different plurality of labels is deemed to not be a probe when the string sequence of the different plurality of labels is not confirmed as a valid reporter sequence. In some instances according to this embodiment of the present invention, a plurality of probes is identified. For instance, in some embodiments, two or more probes, three or more probes, ten or more probes, at least 5, 10, 15, 20, 50, 75, 100, 150, 200, 300, or 400 probes or more are identified.

In some embodiments where a plurality of probes are identified, each type of probe identified is recorded. A probe "type" is identified by the string sequence of the probe. Each unique valid string sequence represents a different probe type. In some embodiments, each string sequence of each different plurality of labels that is not confirmed as a valid reporter sequence is stored. In this way, it is possible to determine common conditions that arise on the substrate. One type of condition that can be identified by tracking pluralities of labels that do not form valid string sequences is the condition where there are too many probes on the substrate. When there are too many probes on the substrate, the labels of neighboring probes become proximate to each other, making it difficult to determine which probe each label belongs to. Another type of condition that can be identified is the condition in which an excessive number of probes are not full length. In some embodiments, all species of labels, strings, invalid reporter sequences, valid reporter sequences, probe types is tracked in the methods of the present invention.

4. BRIEF DESCRIPTION OF THE FIGURES

Figure 1B:
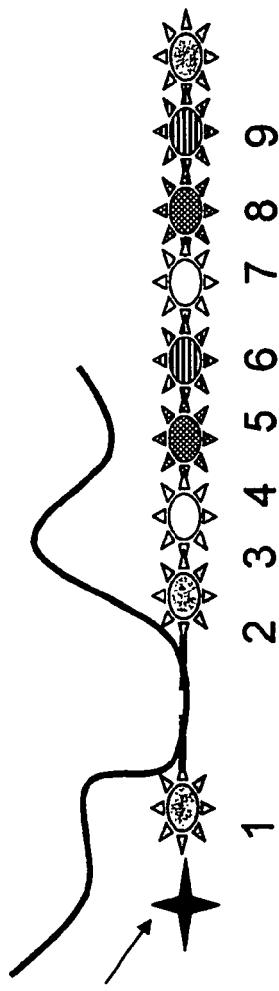
Figure 1C:
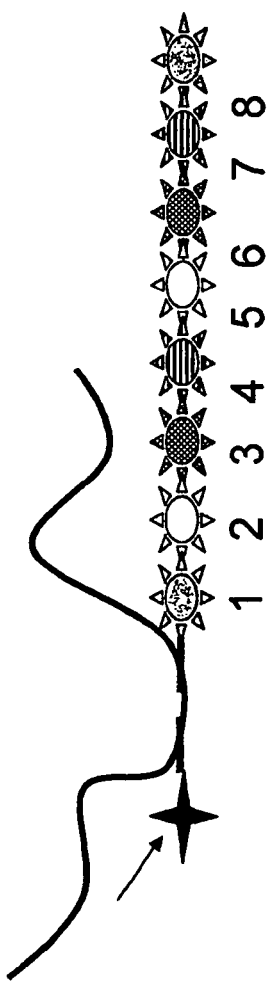
Figure 1D:
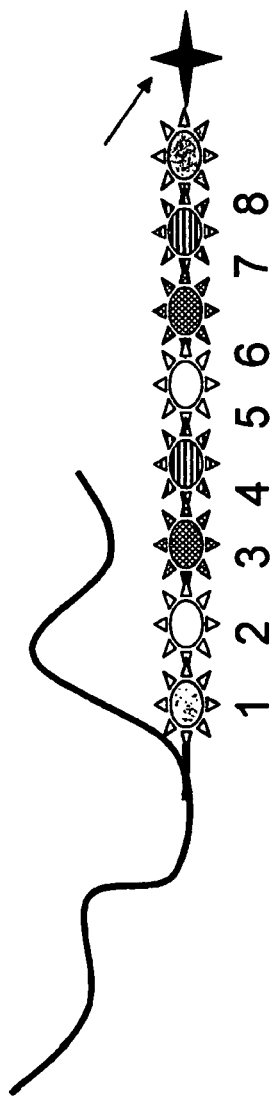
Figure 1E:
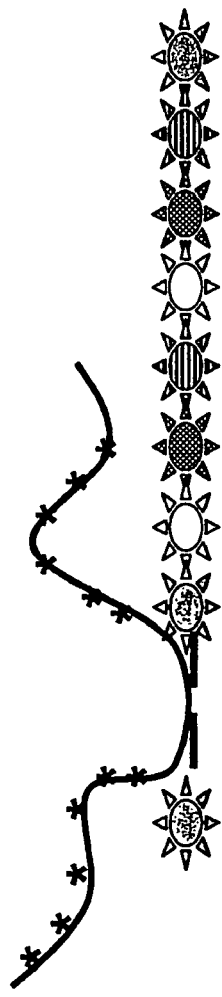
Figure 1F:
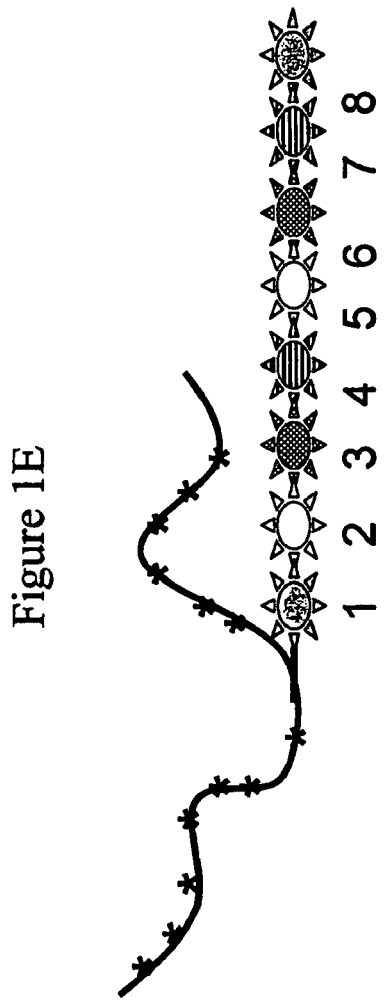

FIGS. 1A-1F. FIG. 1A illustrates a dual nanoreporter with a 16-position nanoreporter code, using two 8-position nanoreporter components. FIG. 1B illustrates a dual nanoreporter with a 9-position nanoreporter code, using one 8-position nanoreporter component and one single-position nanoreporter component. FIG. 1C illustrates a dual nanoreporter with an 8-position nanoreporter code, using one ghost probe and one 8-position nanoreporter component. FIG. 1D illustrates a single nanoreporter with an 8-position nanoreporter code. In FIGS. 1A-1D, the star shape (depicted with an arrow) is illustrative of an affinity tag, which can be used to purify the nanoreporter or immobilize the nanoreporter (or nanoreporter-target molecule complex) for the purpose of imaging. The numbered region in FIGS. 1A-1D refer to separate label attachment regions. All except for position 12 of FIG. 1A are labeled with one of four types of label monomers, depicted as grey, white, hatched or stripe "sun" diagrams. Position 12 of FIG. 1A is an unlabeled "dark spot." FIGS. 1E and 1F represent variations on the nanoreporters of FIGS. 1B and 1D, respectively, in which the target molecule to which the nanoreporters are bound comprises biotin moieties (shown as small asterisks), for example biotin-modified nucleotides randomly incorporated into a target nucleic acid. The nanoreporters themselves further optionally comprise an affinity tag (not shown).

Figure 2A:
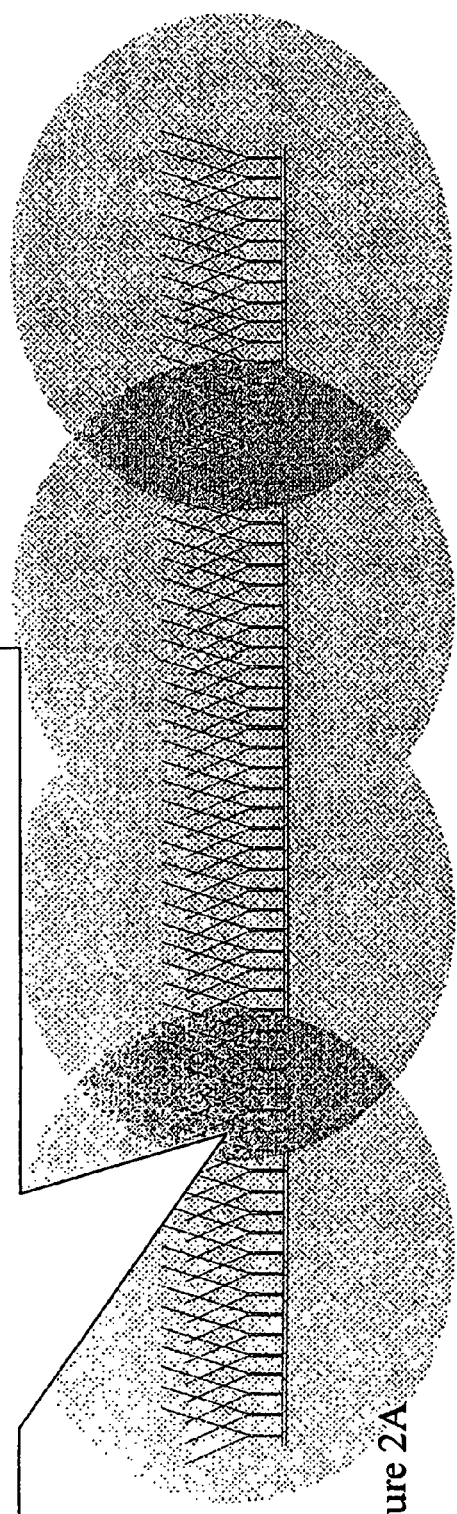
Figure 2C:
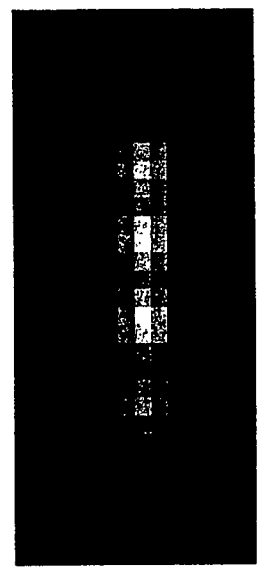
Figure 2B:
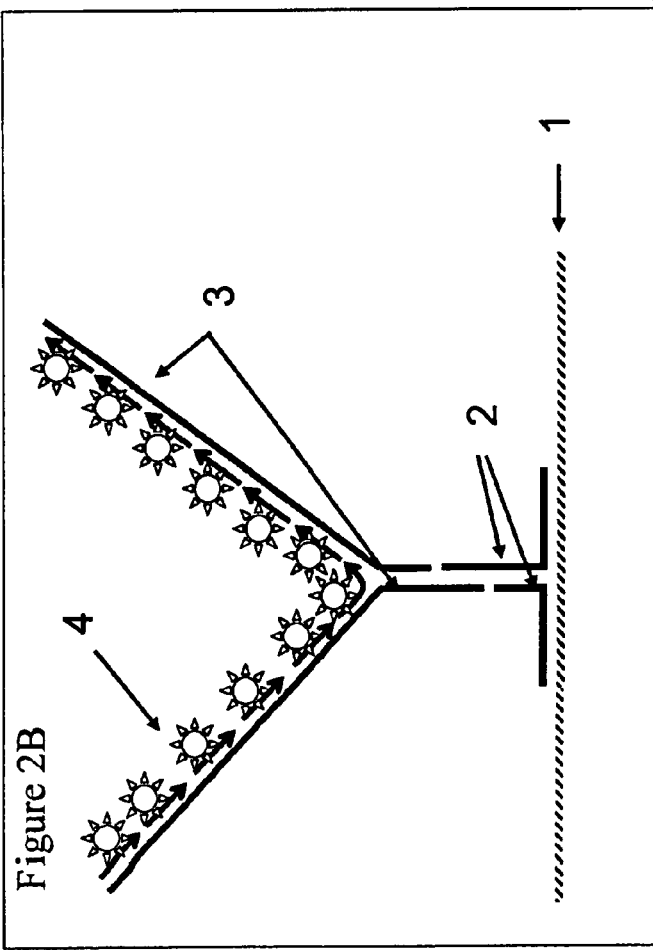

FIGS. 2A-2C. FIG. 2A shows an illustration of a label unit of a nanoreporter, containing a scaffold with patch units and corresponding split flaps disposed along its length. FIG. 2B illustrates the components of a single patch pair and its corresponding flap, containing: 1: a portion of a nanoreporter scaffold (e.g., M13 single-stranded DNA); 2: A patch pair; 3: a split flap pair; and 4: labeled oligonucleotides, each with a label monomer incorporated, hybridized to the split flap. FIG. 2C shows a nanoreporter with 4 "spots," each spot designed to contain 9 patch pairs of 60-65 nucleotides, each attached to a split flap pair of 95-100 nucleotides. Each split flap pair had binding site for 12 oligonucleotides each attached to a single label monomer. Each spot therefore had binding sites for 108 label monomers.

Figures 3A, 3B:
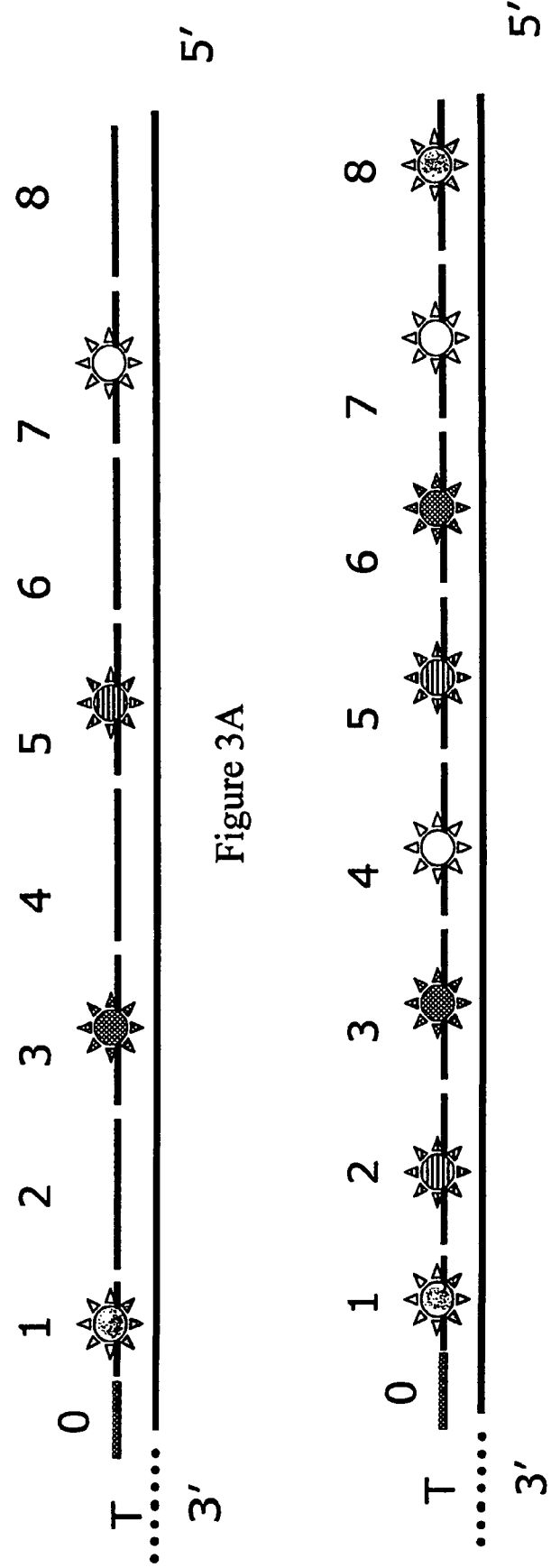

FIG. 3. A nanoreporter in which the patches that are RNA segments can be used with (FIG. 3A) and without registers (FIG. 3B). Both FIGS. 3A and 3B depict a (1) nanoreporter scaffold (heavy black line) to which are attached (2) eight RNA segments (lines 1-8), (3) a target-specific sequence (dotted line "T") and (4) an oligonucleotide (checkered line "O") that is partly complementary to the nanoreporter scaffold and partly complementary to the target-specific sequence. This oligonucleotide is referred to as a "ligator" oligonucleotide. In FIG. 3A, only one register, i.e., every alternate RNA segment is labeled. The second register positions serve as "spacers," making it possible to generate a nanoreporter code in which consecutive positions in the code are the same "color," or spectrally indistinguishable. In FIG. 3B, both registers, i.e., adjacent RNA segments with no intervening spacers, are labeled, with no nearest neighbor of the same "color."

Figure 4:
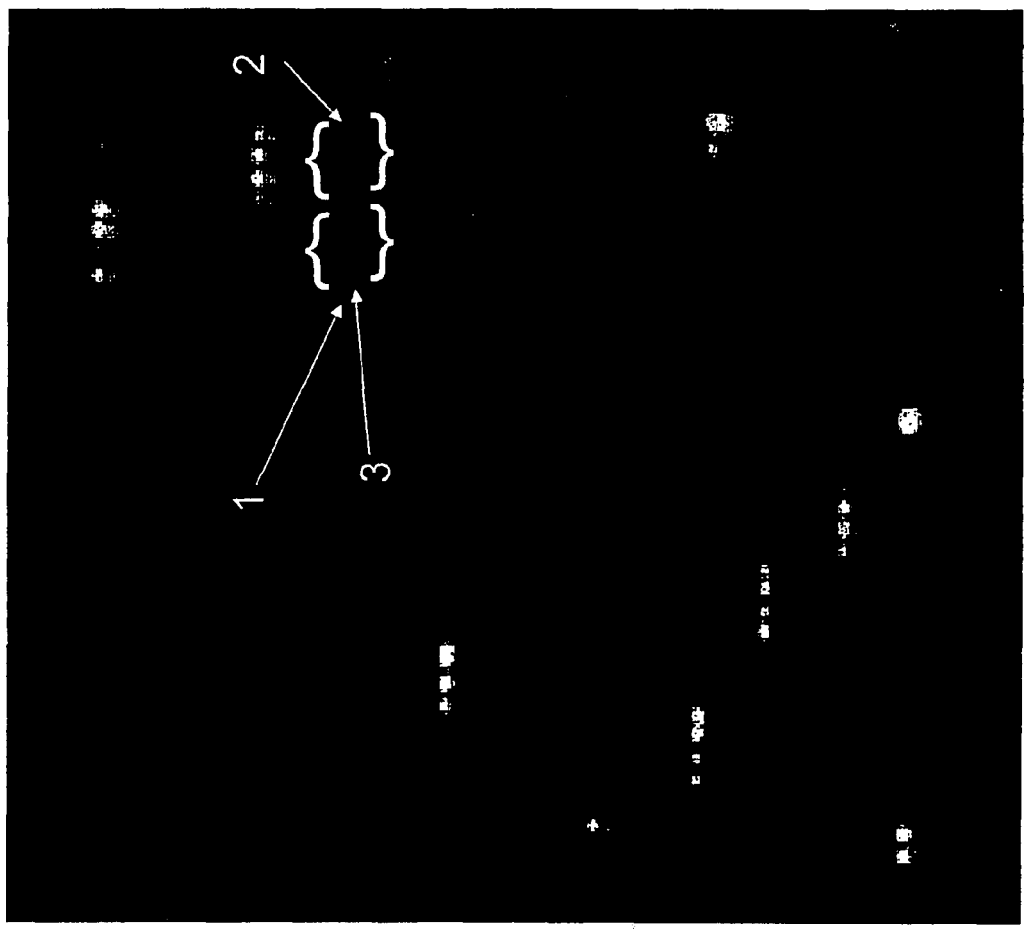

FIG. 4. is an image of a dual nanoreporter hybridized to a target molecule. Here, both registers are labeled. The nanoreporters are labeled with three different colors, Alexa 488, Cy3 and Alexa 647 (labeled 1, 2 and 3, respectively). The left brackets show one probe of the dual nanoreporter and the right brackets show the other probe of the dual nanoreporter. Colors 1, 2 and 3 were each acquired in different channels and the first and second registers, seen as rows of spots, were shifted up by several pixels to be able to show each register individually.

Figure 5A:
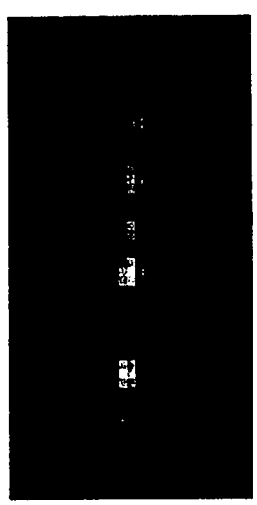
Figure 5B:
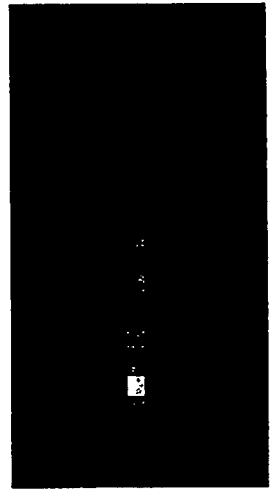
Figure 5C:
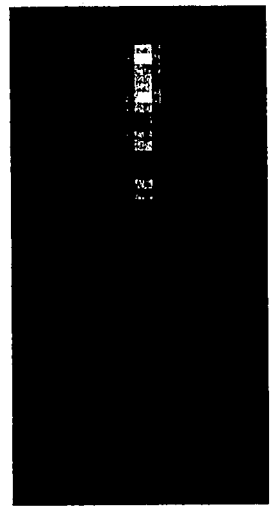
Figure 5D:

FIGS. 5A-5D. This figure illustrates the various components of the dual nanoreporters shown in FIG. 4. FIG. 5A illustrates one color (here, Alexa 488, depicted in the left column as open circles), which is spectrally distinguishable from Cy3 (shown in FIG. 5B, depicted in the left column as vertically striped circles) and Alexa 647 (shown in FIG. 5C as diagonally striped circles). The images obtained from each were superimposed to generate FIG. 5D.

FIGS. 6A-6E. FIG. 6A is a schematic illustration of the experiment shown in FIGS. 6B and 6C. In this case, the star represents biotin that was used to attach the complex by one end to the surface prior to stretching. FIGS. 6B and 6C show images from experiments in which S2-A ghost probe, S2-B labeled nanoreporter and S2 target DNA (FIG. 6B) or S2 target RNA (FIG. 6C) were hybridized. FIG. 6E shows a close-up of a nanoreporter complexes from FIG. 6B, each containing S2-A ghost probe, S2-B labeled nanoreporter and S2 target DNA. FIG. 6D shows an image of a negative control experiment, in which S2-A ghost probe, S2-B labeled nanoreporter and no S2 target RNA were hybridized. FIGS. 7A-G. FIGS. 7A, 7B, 7C and 7D depict different permutations of patches on a nanoreporter scaffold, FIGS. 7E and 7F depict different permutations of split flaps on a nanoreporter scaffold, optionally hybridized to one or more oligonucleotides, as in FIG. 7G. In FIG. 7A-G, α refers to a 5' or 3' molecule or end of a molecule, and β refers to a corresponding 3' or 5' molecule or end of a molecule.

Figure 8:
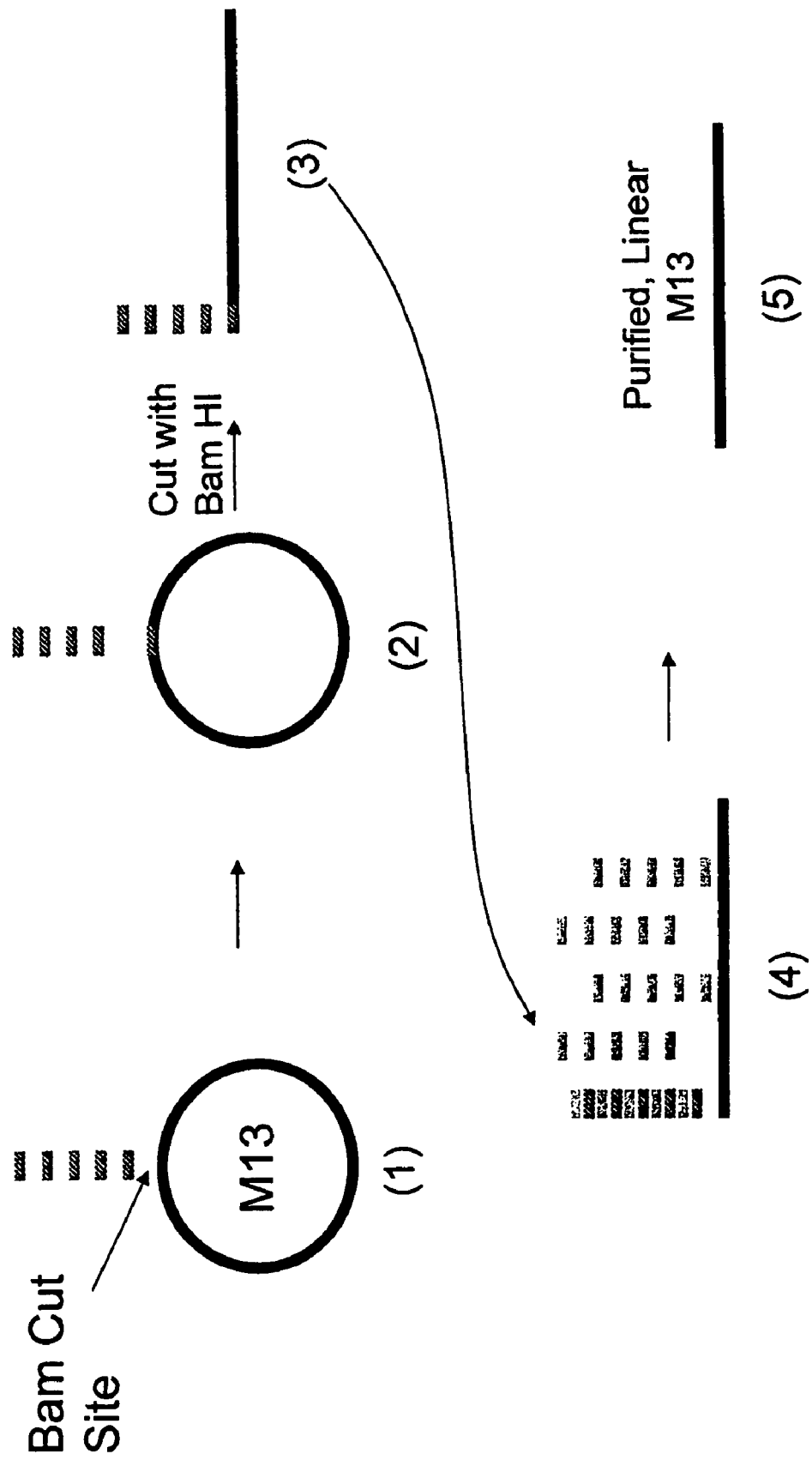

FIG. 8 depicts a scheme in which single-stranded M13 phage is linearized for use as a nanoreporter scaffold. The circular M13 phage is annealed to a five-fold excess of BamH1 cutter oligonucleotide (hatched lines) (1), and the resulting partially double-stranded M13 digested with the restriction endonuclease BamH1 (2), resulting in a linearized M13 in which BamH1 cutter oligonucleotide is still attached (3). This M13-oligonucleotide complex is heated in the presence of an excess oligonucleotide complementary to the BamH1 cutter oligonucleotide (an "anti-BamH1 oligonucleotide") (grey lines) (4). The BamH1 cutter oligonucleotide anneals to the excess of anti-BamH1 oligonucleotide, and the M13 molecule is purified from the oligonucleotide, for example by using size exclusion columns, to yield M13 scaffold.

Figure 9:
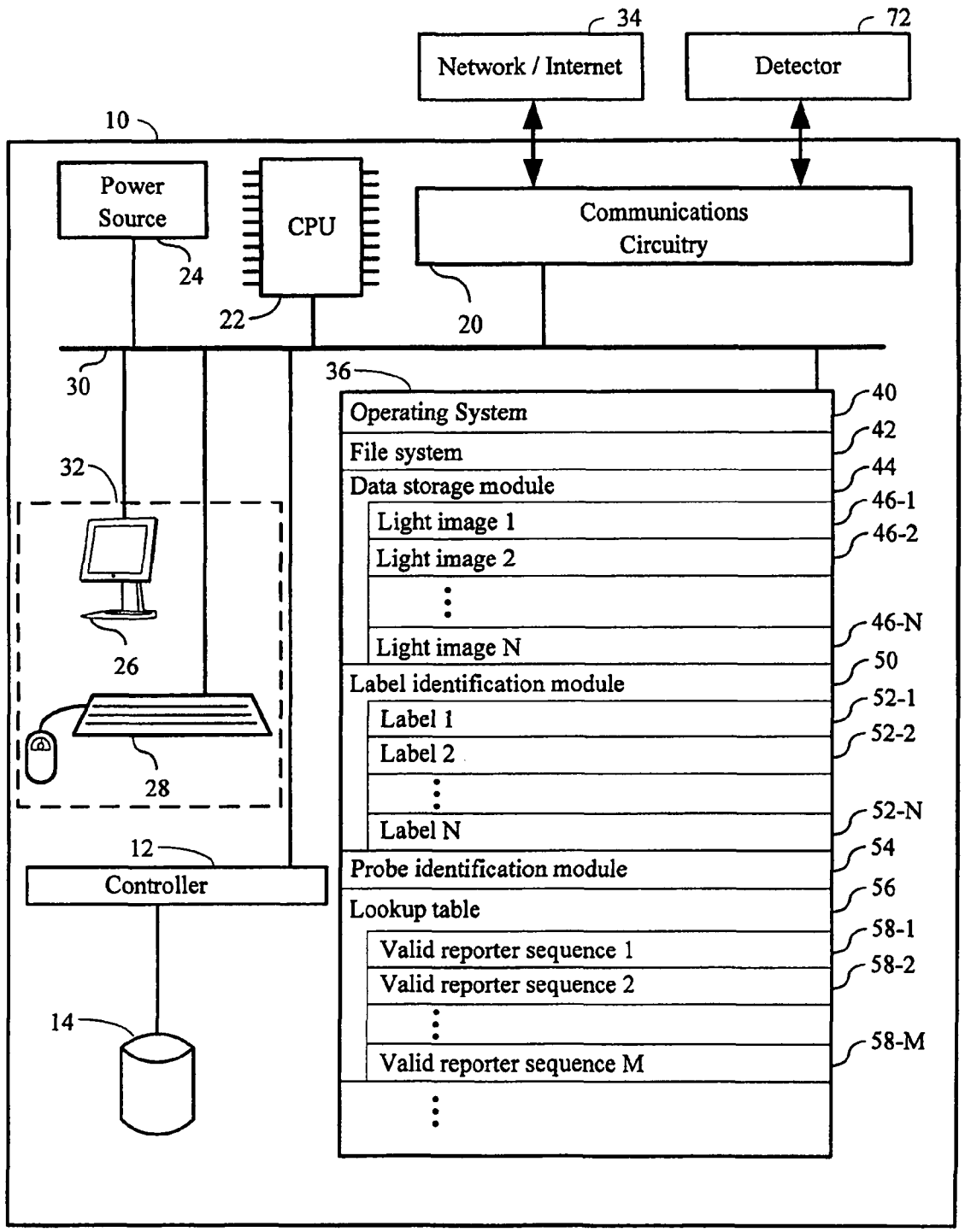

FIG. 9. FIG. 9 illustrates a computer system in accordance with an embodiment of the present invention.

Figure 10A:
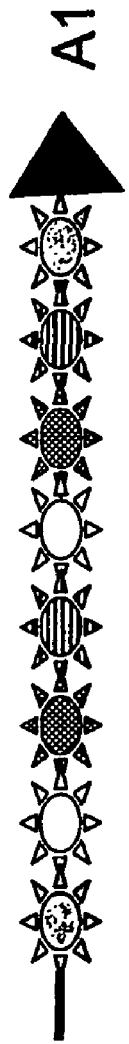
Figure 10B:
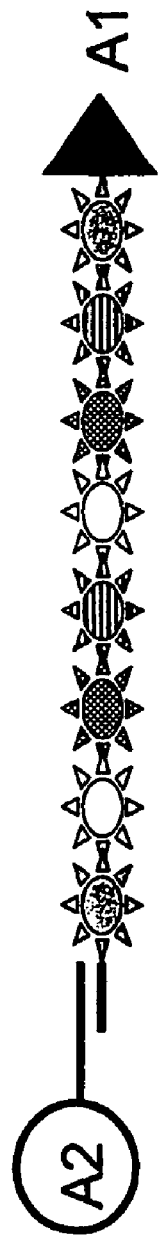
Figure 10C:
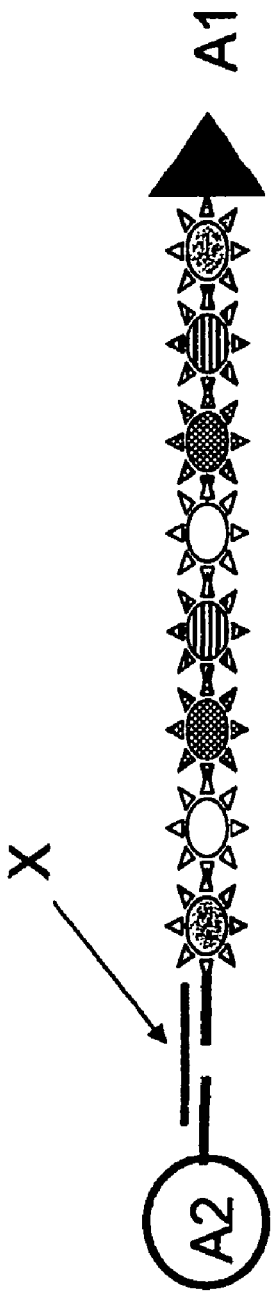

FIGS. 10A-10C. FIG. 10A shows a labeled nanoreporter containing a single affinity tag, A1. Another affinity tag, A2, can be attached to the nanoreporter by direct binding of the nanoreporter to a molecule containing A2 (e.g., if the nanoreporter is or comprises a nucleic acid, it can hybridize directly with another nucleic acid to which A2 is attached), as depicted in FIG. 10B. Alternatively, the second affinity tag, A2, can be attached to the labeled nanoreporter via a bridging molecule, such as the bridging nucleic acid ("X") depicted in FIG. 10C.

Figure 11A:
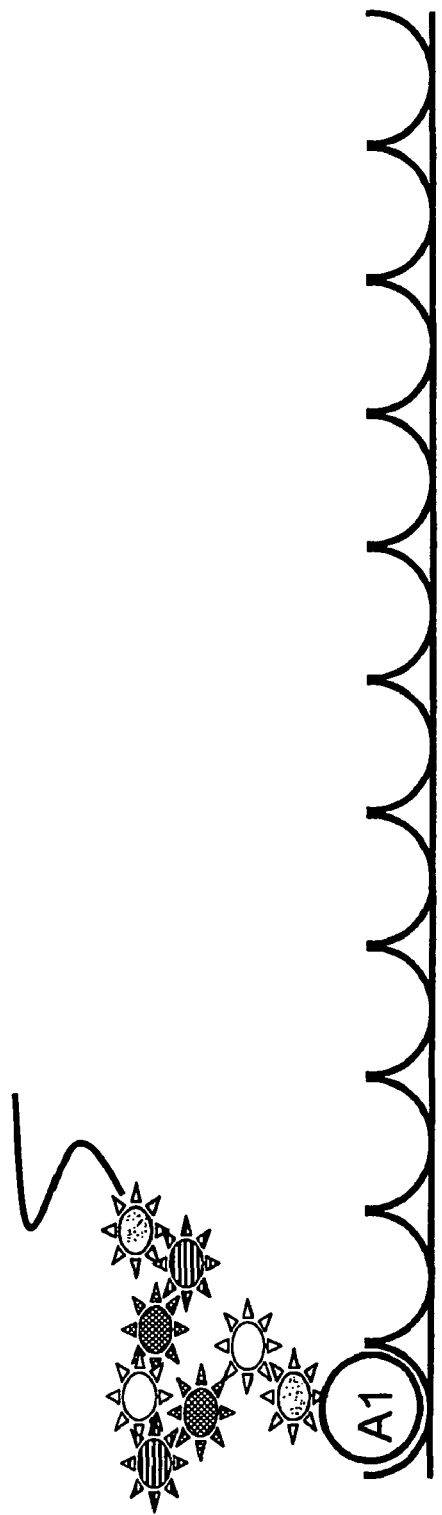
Figure 11B:
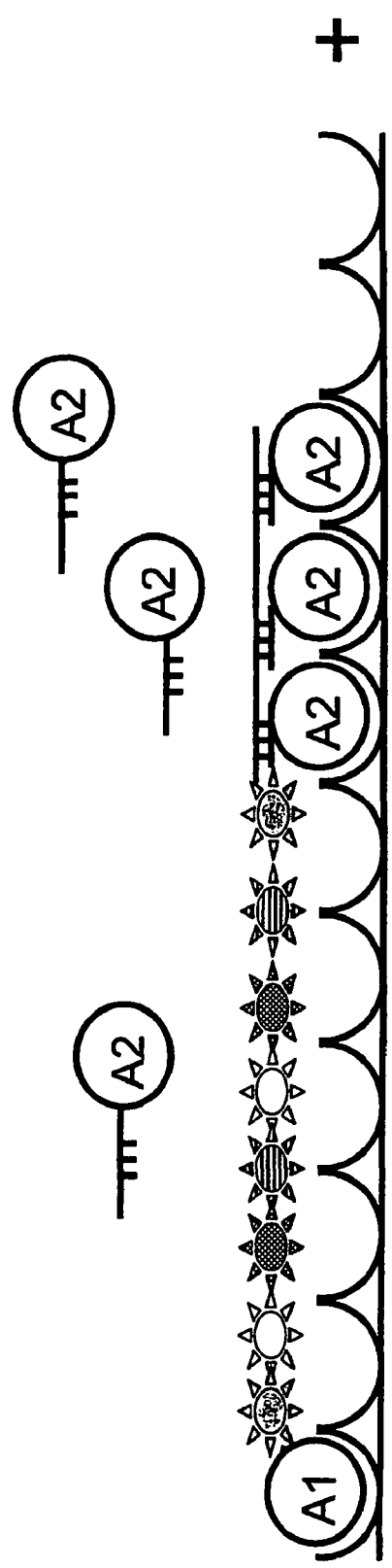

FIGS. 11A-11B depict a labeled (nucleic acid-based) nanoreporter with an affinity tag, A1, at one end. In FIG. 11, the labeled nanoreporter is immobilized through the binding of A1 to an immobilized affinity partner. The other end of the nanoreporter is in solution (FIG. 11A), but can be immobilized by hybridization to a complementary oligonucleotide which contains another affinity tag (A2) used to immobilize the nanoreporter (FIG. 11B). A1 and A2 can be the same, for example biotin, for immobilization on an avidin- or streptavidin-coated surface. Upon immobilization of A1, the nanoreporter can be stretched, or "elongated" as depicted in FIG. 11, for example by electrostretching, for separation of the label attachment regions in a manner that permits detection of the nanoreporter code. Optionally, while the nanoreporter is in an elongated state, A2 is introduced and binds the end of the nanoreporter that is complementary to A2 down to the surface.

FIGS. 12A-12B. FIG. 12A provides an illustration of a nanoreporter comprising an immobilized first portion F1; and FIG. 12B provides an illustration of a nanoreporter extended in an electrical field and comprising immobilized first portion F1 and immobilized second portion F2, wherein F2 is immobilized via a complex with molecule F3.

Figure 13A:
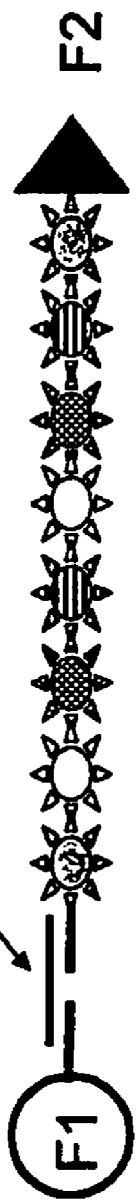
Figure 13B:
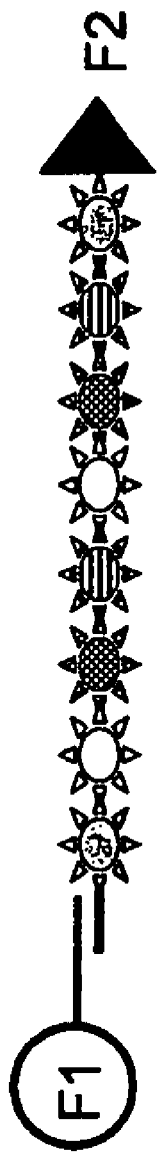
Figure 13C:

FIGS. 13A-13C. FIG. 13A provides an illustration of a three-member complex for immobilization of an extended nanoreporter; FIG. 13B provides an illustration of a two-member complex for immobilization of an extended nanoreporter; and FIG. 13C provides an illustration of an incomplete complex for immobilization of an extended nanoreporter.

Figure 14A:
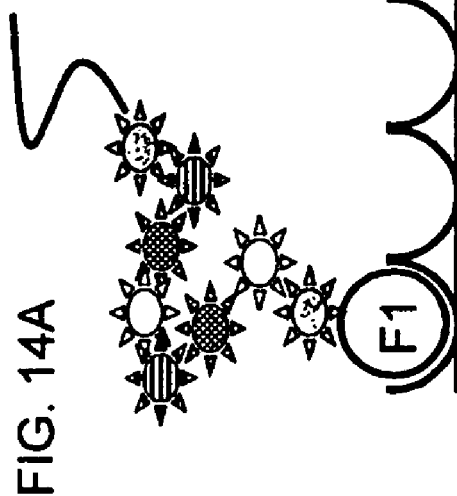
Figure 14B:
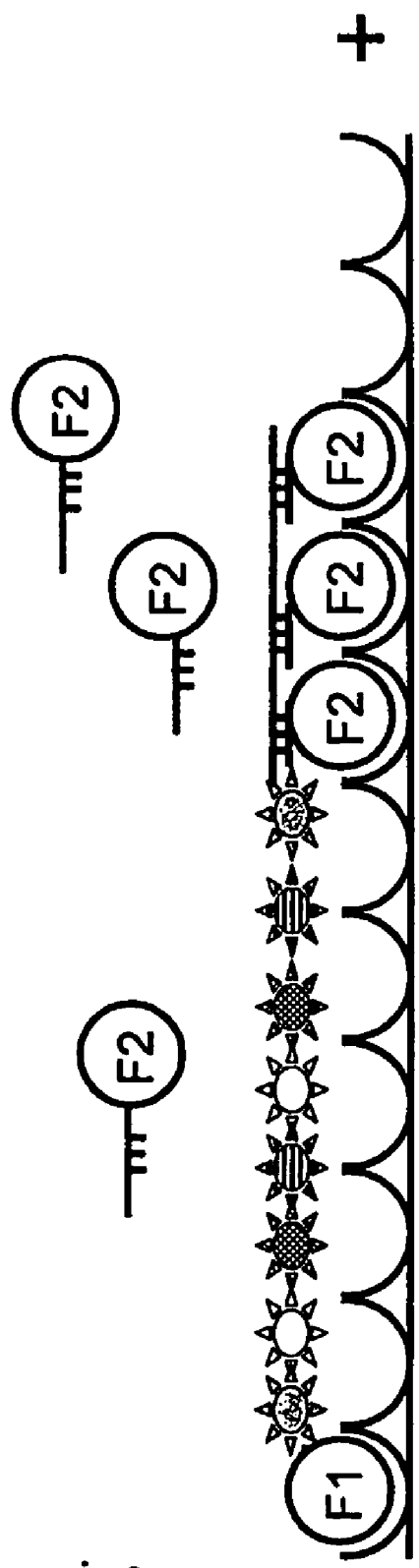
Figure 14C:
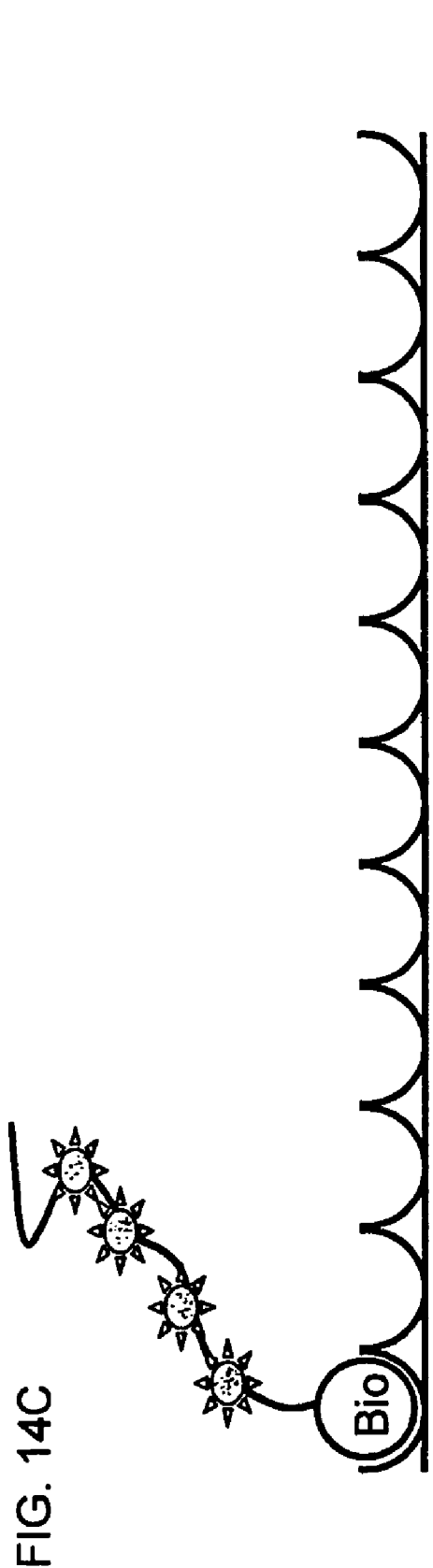
Figure 14D:
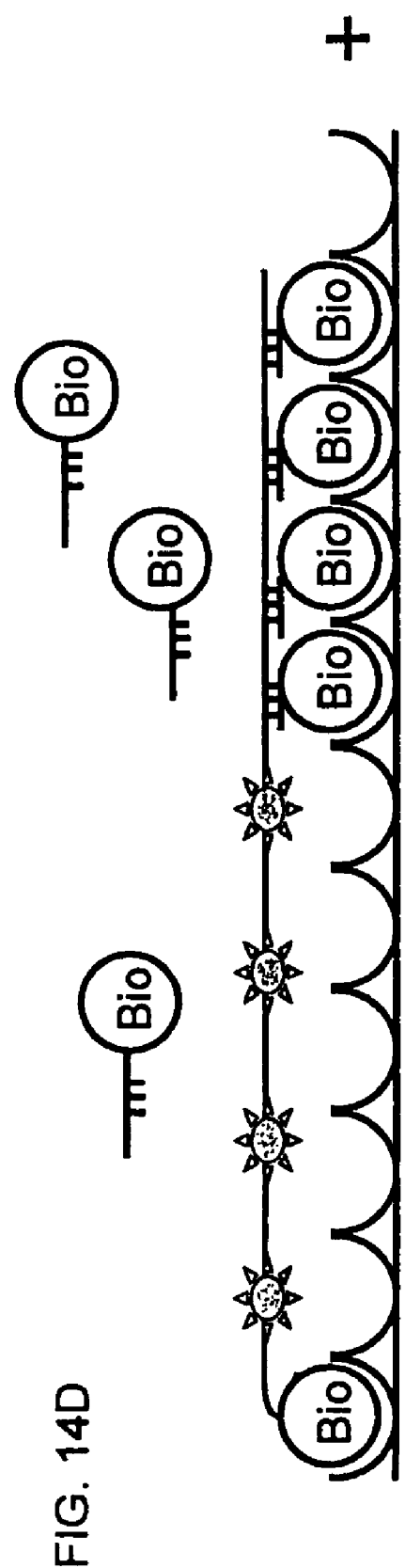

FIGS. 14A-14D. FIG. 14A provides an illustration of a nanoreporter comprising an immobilized first portion F1; FIG. 14B provides an illustration of an extended nanoreporter immobilized at first portion F1 and at a second portion via complexes with F2; FIG. 14C provides an illustration of a nanoreporter comprising a first portion immobilized to an avidin surface via biotin; and FIG. 14D provides an illustration of an extended nanoreporter immobilized at a first portion and at a second portion via selective binding of biotin to an avidin surface.

Figure 15A:
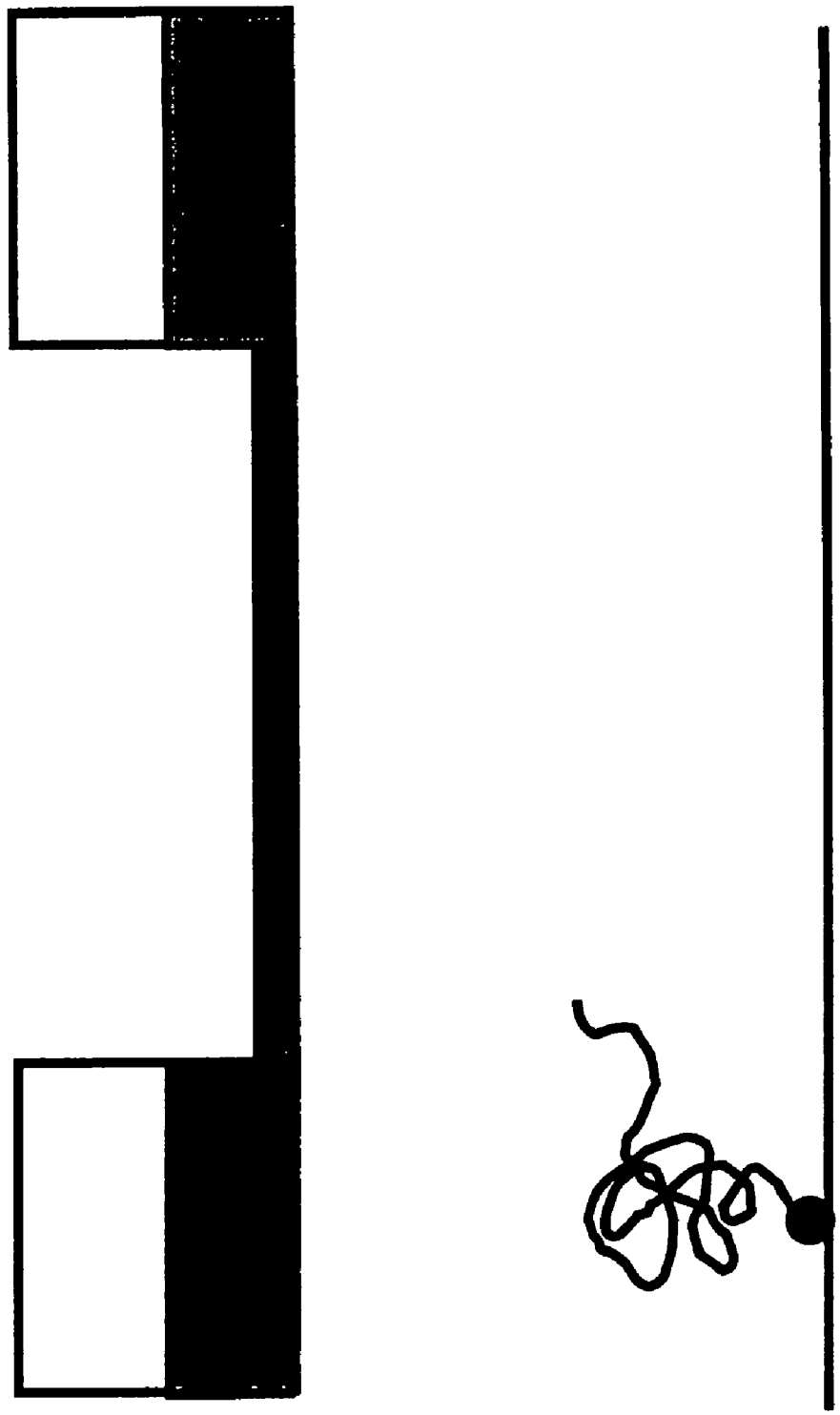
Figure 15B:
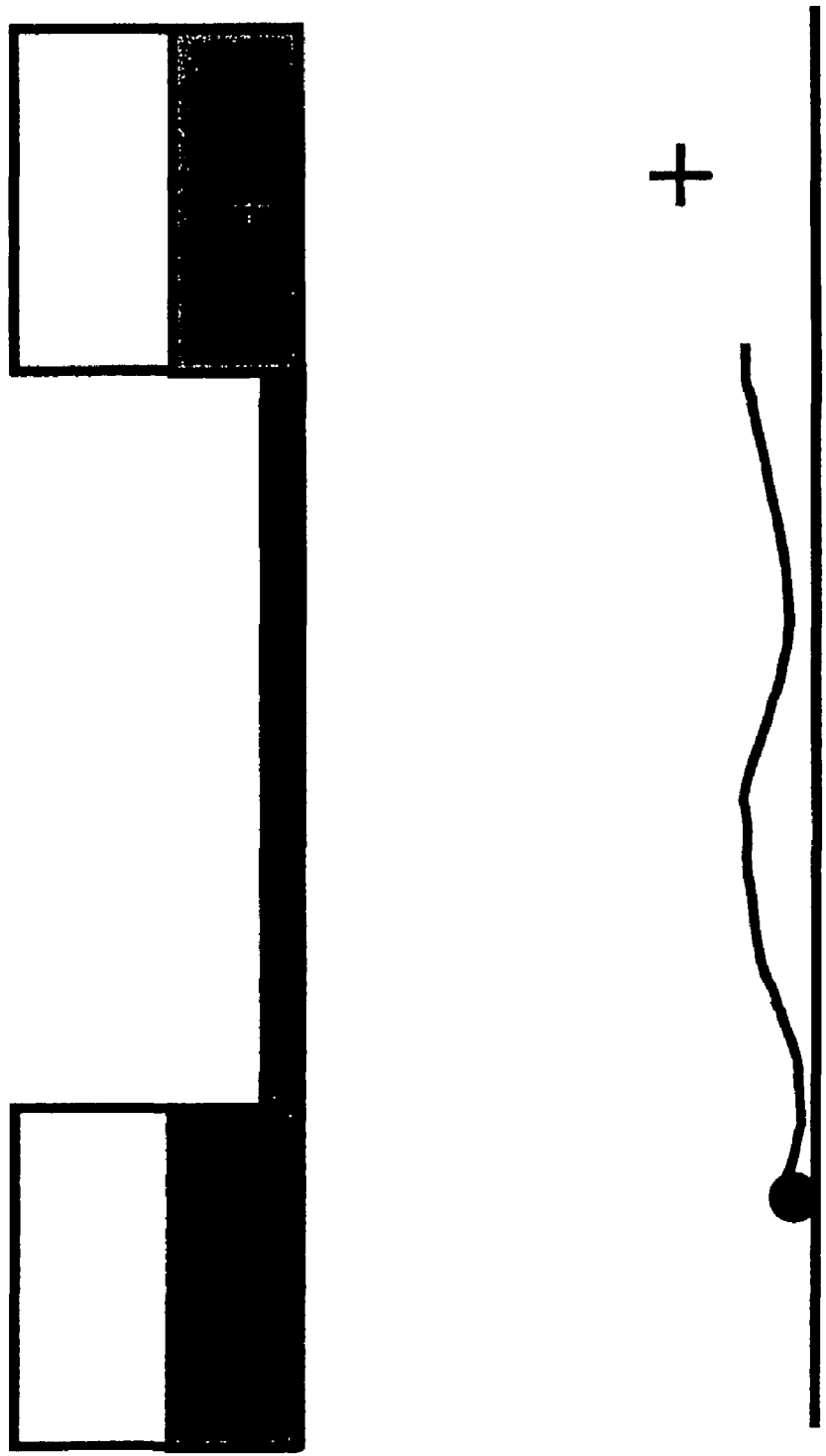
Figure 15C:
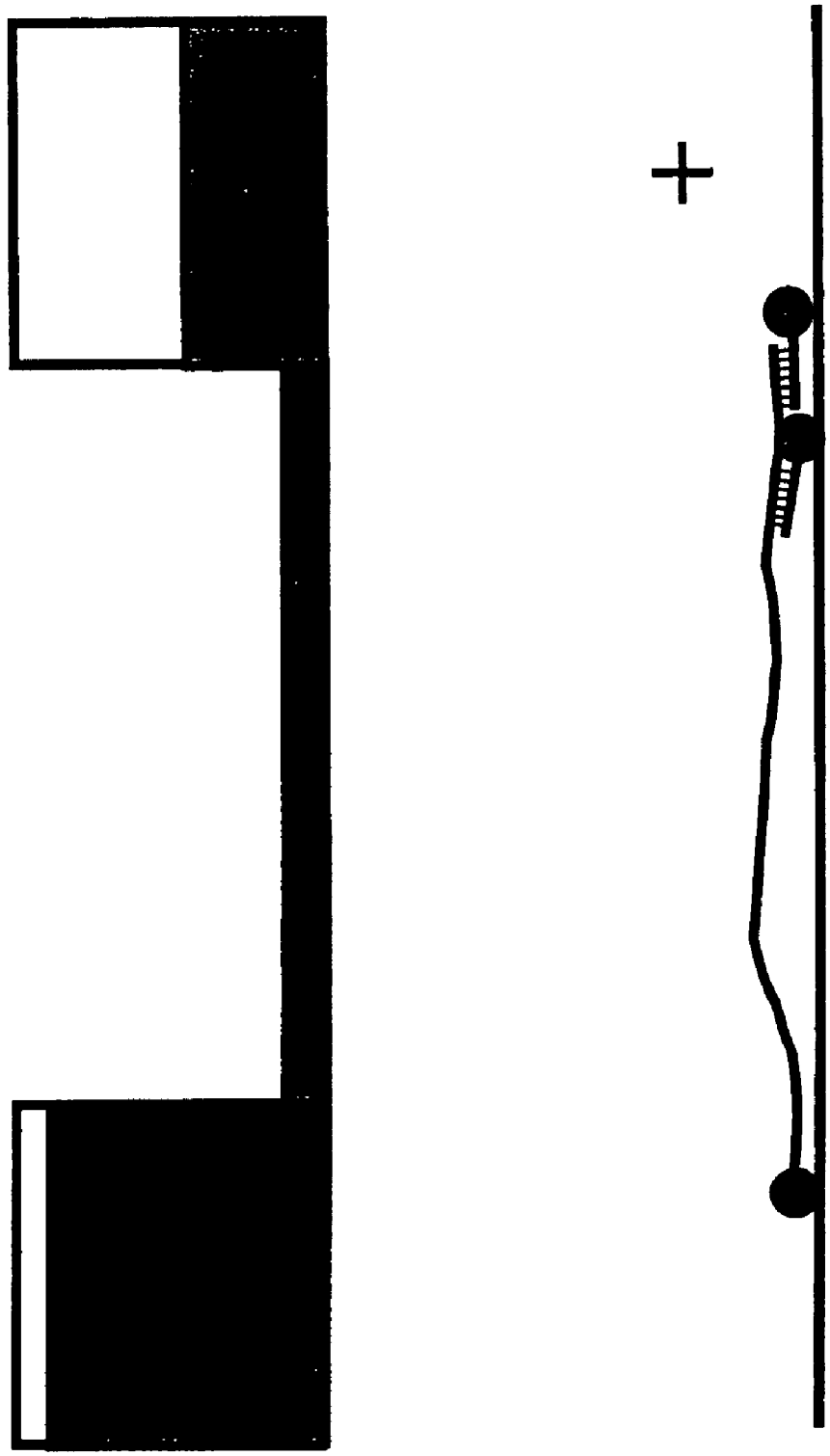

FIGS. 15A-15C. FIG. 15A illustrates immobilization of one terminus of a DNA molecule in a microfluidic device; FIG. 15B illustrates extension of the DNA in an electric field; and FIG. 15C illustrates selective immobilization of a second terminus of the extended DNA molecule.

Figure 16:

FIG. 16 provides an image of extended nanoreporters selectively immobilized by the methods of the present invention.

5. DETAILED DESCRIPTION OF THE INVENTION

The present invention pertains to nanoreporters, and their manufacture and use. A fully assembled and labeled nanoreporter comprises two main portions, a target-specific sequence that is capable of binding to a target molecule, and a labeled region which emits a "code" of signals (the "nanoreporter code") associated with the target-specific sequence. Upon binding of the nanoreporter to the target molecule, the nanoreporter code identifies the target molecule to which the nanoreporter is bound.

Nanoreporters are modular structures. Generally, a nanoreporter is a molecular entity containing three basic elements: a scaffold containing two or more label attachment regions, one or more patches attached to the scaffold, and a target-specific sequence, also attached to the scaffold. The elements of a nanoreporter can be found in a single molecular entity (a "singular" nanoreporter), or two distinct molecular entities (a "dual" nanoreporter). Each molecular entity may be composed of one molecule or more than one molecule attached to one another by covalent or non-covalent means. Generally, each component of a dual nanoreporter has a target-specific sequence that binds to a different site on the same target molecule. This allows for smaller nanoreporter components with more efficient kinetics of binding of the nanoreporter to the target molecule and better signal:noise ratios resulting from the greater binding specificity.

The patches attached to a nanoreporter scaffold serve to attach label monomers to a nanoreporter scaffold. Patches may be directly labeled, for example by covalent incorporation of one or more label monomers into nucleic acid patches. Alternatively, patches may be attached to flaps, which maybe labeled directly, for example by covalent incorporation of one or more label monomers into a nucleic acid flap, or indirectly, for example by hybridization of a nucleic acid flap to an oligonucleotide which is covalently attached to one or more label monomers. Where the label monomers attached to a label attachment region are not directly incorporated into a patch or flap, the patch or flap serves as a "bridge" between the label monomer and the label attachment region, and may be referred to as a "bridging molecule," e.g., a bridging nucleic acid.

Additionally, nanoreporters may have affinity tags for purification and/or for immobilization (for example to a solid surface). Nanoreporters, or nanoreporter-target molecule complexes, are preferably purified in two or more affinity selection steps. For example, in a dual nanoreporter, one probe can comprise a first affinity tag and the other probe can comprise a second (different) affinity tag. The probes are mixed with target molecules, and complexes comprising the two probes of the dual nanoreporter are separated from unbound materials (e.g., the target or the individual probes of the nanoreporter) by affinity purification against one or both individual affinity tags. In the first step, the mixture can be bound to an affinity reagent for the first affinity tag, so that only probes comprising the first affinity tag and the desired complexes are purified. The bound materials are released from the first affinity reagent and optionally bound to an affinity reagent for the second affinity tag, allowing the separation of complexes from probes comprising the first affinity tag. At this point only full complexes would be bound. The complexes are finally released from the affinity reagent for the second affinity tag and then preferably stretched and imaged. The affinity reagent can be any solid surface coated with a binding partner for the affinity tag, such as a column, bead (e.g., latex or magnetic bead) or slide coated with the binding partner. Immobilizing and stretching nanoreporters using affinity reagents is fully described in U.S. provisional application no. 60/753,816 by Sean M. Ferree and Dwayne L. Dunaway, entitled "Compositions Comprising Oriented, Immobilized Macromolecules and Methods for Their Preparation," filed on Dec. 23, 2005, which is incorporated by reference herein in its entirety.

Nanoreporter and nanoreporter-target complexes which are or comprise nucleic acids may be affinity-purified or immobilized using a nucleic acid, such as an oligonucleotide, that is complementary to at least part of the nanoreporter or target. In a specific application where the target includes a poly A or poly dA stretch, the nanoreporter-target complex can be purified or immobilized by an affinity reagent coated with a poly dT oligonucleotide.

The sequence of signals emitted by the label monomers associated with the various label attachment regions of the scaffold of a given nanoreporter allows for the unique identification of the nanoreporter. A nanoreporter having a unique identity or unique spectral signature is associated with a target-specific sequence that recognizes a specific target molecule or a portion thereof. When a nanoreporter is exposed to a mixture containing the target molecule under conditions that permit binding of the target-specific sequence(s) of the nanoreporter to the target molecule, the target-specific sequence(s) preferentially bind(s) to the target molecule. Detection of the spectral code associated with the nanoreporter allows detection of the presence of the target molecule in the mixture (qualitative analysis). Counting all the label monomers associated with a given spectral code or signature allows the counting of all the molecules in the mixture associated with the target-specific sequence coupled to the nanoreporter (quantitative analysis). Nanoreporters are thus useful for the diagnosis or prognosis of different biological states (e.g., disease vs. healthy) by quantitative analysis of known biological markers. Moreover, the exquisite sensitivity of single molecule detection and quantification provided by the nanoreporters of the invention allows for the identification of new diagnostic and prognostic markers, including those whose fluctuations among the different biological states is too slight detect a correlation with a particular biological state using traditional molecular methods. The sensitivity of nanoreporter-based molecular detection permits detailed pharmacokinetic analysis of therapeutic and diagnostic agents in small biological samples.

Many nanoreporters, referred to as singular nanoreporters, are composed of one molecular entity, as depicted in FIG. 1D. However, to increase the specificity of a nanoreporter and/or to improve the kinetics of its binding to a target molecule, a preferred nanoreporter is a dual nanoreporter composed of two molecular entities, each containing a different target-specific sequence that binds to a different region of the same target molecule. Various embodiments of dual nanoreporters are depicted in FIGS. 1A-1C. In a dual nanoreporter, at least one of the two molecular entities is labeled. The other molecular entity is not necessarily labeled. Such unlabeled components of dual nanoreporters are referred to herein as "ghost probes" (see FIG. 1C) and often have affinity tags attached, which are useful to immobilize and/or stretch the complex containing the dual nanoreporter and the target molecule to allow visualization and/or imaging of the complex.

Because of their modular structures, nanoreporters may be assembled and labeled in a variety of different ways. For example, a nanoreporter scaffold can be attached to a target-specific sequence (for example by hybridization and, optionally, ligation), and the structure comprising the scaffold and target-specific sequence attached to one or more patches and, where desired, flaps. Alternatively, the nanoreporter scaffold can first be attached to one or more patches (and, optionally, flaps), and the scaffold/patch structure then attached to a target specific sequence. Thus, unless stated otherwise, a discussion or listing of steps in nanoreporter assembly does not imply that a specific route of assembly must be followed.

Nanoreporter assembly and use is exemplified herein largely by way of description of a variety of nucleic acid-based nanoreporters; however, one of skill in the art would recognize that the methods described herein are applicable to an amino acid-based (or hybrid nucleic acid-/amino acid-based) nanoreporter. Illustrative embodiments of partially and fully assembled nanoreporters are listed below.

At its simplest, a nanoreporter comprises a scaffold having at least two label attachment regions capable of being labeled and resolved. The scaffold can be any molecular entity that allows the formation of label attachment regions on the scaffold that can be separately labeled and resolved. The number of label attachment regions to be formed on a scaffold is based on the length and nature of the scaffold, the means of labeling the nanoreporter, as well as the type of label monomers emitting a signal to be attached to the label attachment regions of the scaffold. A nanoreporter according to the invention may have a scaffold including two or more label attachment regions. Suitable scaffold structures include DNA-based scaffolds.

The invention also provides labeled nanoreporters in which one or more label attachment regions are attached to corresponding label monomers, each label monomer emitting a signal. For example a labeled nanoreporter according to the invention is obtained when at least two label monomers are attached to two corresponding label attachment regions of the scaffold such that these labeled label attachment regions, or "spots," are distinguishable. Label monomers emitting a signal associated with different label attachment regions of the scaffold can emit signals that are spectrally indistinguishable under the detection conditions ("like" signals), or can emit signals that are spectrally distinguishable under the detection conditions.

The invention also provides a nanoreporter in which two or more label monomers are attached to a label attachment region. The signal emitted by the label monomers associated with the label attachment region produces an aggregate signal that is detected. The aggregate signal produced may be made up of like signals or made up of at least two spectrally distinguishable signals.

In one embodiment, the invention provides a nanoreporter in which at least two label monomers emitting like signals are attached to two corresponding label attachment regions of the scaffold and the two label monomers are spatially distinguishable. In another embodiment, the invention provides a nanoreporter in which at least two label monomers emitting two distinguishable signals are attached to two neighboring label attachment regions, for example two adjacent label attachment regions so that at least two label monomers are spectrally distinguishable.

The invention provides a nanoreporter in which two spots emitting like signals are separated by a spacer region. Such a spacer region allows resolution or better resolution of the like signals emitted by label monomers attached to the two spots. In one embodiment, the spacer regions have a length determined by the resolution of an instrument employed in detecting the nanoreporter.

The invention provides a nanoreporter with one or more "double spots." Each double spot contains two or more (e.g., three, four or five) adjacent spots that emit like signals without being separated by a spacer region. Double spots can be identified by their sizes. A label monomer emitting a signal according to the invention may be attached covalently or non-covalently (e.g., via hybridization) to a patch that is attached to the label attachment region. The label monomers may also be attached covalently or non-covalently (e.g., via hybridization) to a flap attached to a patch that is in turn attached to the scaffold. The flap can be formed by one molecule or two or more molecules ("flap pieces") that form a split flap.

The invention also provides a nanoreporter associated with a spectral code determined by the sequence of signals emitted by the label monomers attached (e.g., indirectly via a patch) to label attachment regions on the scaffold of the nanoreporter, whereby detection of the spectral code allows identification of the nanoreporter.

In one embodiment, the invention provides a nanoreporter further comprising an affinity tag attached to the nanoreporter scaffold, such that attachment of the affinity tag to a support allows scaffold stretching and resolution of signals emitted by label monomers corresponding to different label attachment regions on the scaffold. Nanoreporter stretching may involve any stretching means known in the art including but not limited to, means involving physical, hydrodynamic or electrical means.

In yet another embodiment, the invention provides a nanoreporter further comprising flaps attached to label attachment regions of the scaffold, wherein a flap attached to a label attachment region of the scaffold attaches the label monomer corresponding to the label attachment region, thereby indirectly attaching label monomers to corresponding label attachment regions on the scaffold. In a further embodiment, each label monomer comprises a signal emitting portion and an oligonucleotide portion of a predetermined sequence, and the flaps comprise repeats of a flap sequence complementary to the oligonucleotide portion of a corresponding label, whereby one or more label monomers attach to a corresponding label attachment region through hybridization of the oligonucleotide portions of the label monomers to the repeats of the flap sequence thereby producing a labeled nanoreporter.

A nanoreporter according to the invention can further include a target-specific sequence coupled to the scaffold. The target-specific sequence is selected to allow the nanoreporter to recognize, bind or attach to a target molecule. The nanoreporters of the invention are suitable for identification of target molecules of all types. For example, appropriate target-specific sequences can be coupled to the scaffold of the nanoreporter to allow detection of a target molecule. Preferably the target molecule is DNA (including cDNA), RNA (including mRNA and cRNA), a peptide, a polypeptide, or a protein.

One embodiment of the invention provides increased flexibility in target molecule detection with label monomers according to the invention. In this embodiment, a dual nanoreporter comprising two different molecular entities, each with a separate target-specific region, at least one of which is labeled, bind to the same target molecule. Thus, the target-specific sequences of the two components of the dual nanoreporter bind to different portions of a selected target molecule, whereby detection of the spectral code associated with the dual nanoreporter provides detection of the selected target molecule in a biomolecular sample contacted with the dual nanoreporter.

The invention also provides a method of detecting the presence of a specific target molecule in a biomolecular sample comprising: (i) contacting the sample with a dual nanoreporter under conditions that allow binding of the target-specific sequences in the dual nanoreporter to the target molecule and (ii) detecting the spectral code associated with the dual nanoreporter. Depending on the nanoreporter architecture, the dual nanoreporter may be labeled before or after binding to the target molecule.

Structural stability of a nanoreporter can be increased through ligation of the patches and, optionally, ligation of the split flaps and/or the labeled oligonucleotides hybridized to the split flaps.

In addition to the qualitative analytical capabilities provided by the nanoreporters of the invention and the analytical techniques based thereon, the nanoreporters of the invention are uniquely suitable for conducting quantitative analyses. By providing a one to one binding between the nanoreporters (whether singular or dual nanoreporters) of the invention and their target molecules in a biomolecular sample, all or a representative portion of the target molecules present in the sample can be identified and counted. This individual counting of the various molecular species provides an accurate and direct method for determining the absolute or relative concentration of the target molecule in the biomolecular sample. Moreover, the ability to address each molecule in a mixture individually leverages benefits of miniaturization including high sensitivity, minimal sample quantity requirements, high reaction rates which are afforded by solution phase kinetics in a small volume, and ultimately very low reagent costs.

As will be appreciated from the description and examples provided below, the present invention provides numerous advantages. For example, the complex modularity in forming nanoreporters according to the invention allows for systematic creation of libraries of unique nanoreporters having a very high degree of diversity (e.g., millions of uniquely recognizable nanoreporters). This modularity allows flexibility in customizing nanoreporter populations to specific applications which in turn provides significant manufacturing efficiencies. Another advantage that will be appreciated through the following description stems from the flexibility in assembling the nanoreporters of the invention. That is, due to their modular structure, the nanoreporters of the invention can be assembled prior to shipment to a point of use or assembled at the point of use.

5.1 Nanoreporter Nomenclature

All terms used herein have their ordinary meanings to those of skill in the art unless indicated otherwise. The following terms shall have the following meanings.

BINDING PAIR. The term "binding pair" refers to first and second molecules or moieties that are capable of selectively binding to each other, i.e. binding to each other with greater affinity than to other components in a composition. The binding between the members of the binding pair can be covalent or non-covalent. In certain embodiments, the binding is non-covalent. Exemplary binding pairs include immunological binding pairs (e.g., any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone-hormone binding protein, receptor-receptor ligand (e.g., acetylcholine receptor-acetylcholine or an analog thereof), IgG-protein A, lectin-carbohydrate, enzyme-enzyme cofactor, enzyme-enzyme inhibitor, complementary polynucleotide pairs capable of forming nucleic acid duplexes, and the like). For instance, immunoreactive binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other binding members. Other common binding pairs include but are not limited to, biotin and avidin (or derivatives thereof), biotin and streptavidin, carbohydrates and lectins, complementary nucleotide sequences (including probe and capture nucleic acid sequences), complementary peptide sequences including those formed by recombinant methods, effector and receptor molecules, hormone and hormone binding protein, enzyme cofactors and enzymes, enzyme inhibitors and enzymes, and so forth.

DARK SPOT. The term "dark spot" refers to a lack of signal, or "spot," from a label attachment site on a nanoreporter. Dark spots can be incorporated into the nanoreporter code to add more coding permutations and generate greater nanoreporter diversity in a nanoreporter population.

EXTENDED STATE. The term "Extended state" refers to a nanoreporter in a state that would be recognized as extended by one of skill in the art. In certain embodiments, a nanoreporter is in an extended state when it is extended relative to its native conformation in solution. In certain embodiments, a nanoreporter is in an extended state when it is in the field of a force capable of extending the nanoreporter. In certain embodiments, an extended state of a nanoreporter can be determined quantitatively. In such embodiments, those of skill in the art will recognize R as the end-to-end vector of the nanoreporter, i.e. the distance between two termini of the nanoreporter, and $\langle R \rangle$ as the average end-to-end vector such that 95% of R will be within $2\langle R \rangle$ in a solution deemed appropriate to one of skill in the art. Exemplary solutions include, for example, a dilute solution of the nanoreporter in water or in a pH buffer. In particular embodiments, a nanoreporter is in an extended state when R is greater than $2.0\langle R \rangle$.

FLAP. The term "flap" as used herein refers to a molecular entity attached to a patch or patch pair attached to a label attachment region. The flap is one or more molecules containing label monomers or capable of binding one or more molecules containing label monomers. By providing indirect labeling of the regions, the flaps provide more flexibility in controlling the number of signal emitting monomers associated with a region as well as the nature of those monomers. Flaps may be formed by a single molecular piece or several molecular pieces (e.g., two pieces) forming a "split flap" (see, e.g., FIG. 7).

GHOST PROBE. A molecule comprising a target-specific sequence, but which is not labeled with a label monomer that emits a signal that contributes to the nanoreporter code.

LABELED NANOREPORTER. A labeled nanoreporter is a nanoreporter in which at least one patch of the nanoreporter is attached to one or more label monomers that generate(s) a signal that forms at least part of the nanoreporter code.

LABEL UNIT. The term "label unit" refers to the non-target-specific portions of a labeled nanoreporter.

NANOREPORTER. The term "nanoreporter" refers to a molecular entity that has (i) a molecule ("scaffold") containing at least two label attachment regions; (ii) at least one patch attached to at least one label attachment region; and (iii) a target-specific sequence. As described in detail below, nanoreporters can be singular nanoreporters (all components being in a single molecular entity) or dual nanoreporters (all the components being in two separate molecular entities). Nanoreporters are preferably synthetic, i.e., non-naturally-occurring molecules, for example are chimeric molecules made by joining two or more manmade and/or naturally occurring sequences that normally exist on more than one molecule (e.g., plasmid, chromosome, viral genome, protein, etc.).

NANOREPORTER CODE. The order and nature (e.g., primary emission wavelength(s), optionally also length) of spots from a nanoreporter serve as a nanoreporter code that identifies the target molecule capable of being bound by the nanoreporter through the nanoreporter's target specific sequence(s). When the nanoreporter is bound to a target molecule, the nanoreporter code also identifies the target molecule. Optionally, the length of a spot can be a component of the nanoreporter code.

ORIENTED STATE. The term "oriented state" refers to a nanoreporter in a state that would be recognized as oriented by one of skill in the art. In certain embodiments, a nanoreporter is in an oriented state when it is oriented relative to its native conformation in solution. In certain embodiments, the nanoreporter is oriented when it is arranged in parallel with the field of a force capable of orienting the nanoreporter. In certain embodiments, the nanoreporter is oriented when it is one of a plurality of nanoreporters that are arranged in parallel, as recognized by those of skill in the art.

PATCH. The term "patch" refers to a molecular entity attached to the label attachment region of the nanoreporter scaffold, generally for the purpose of labeling the nanoreporter. The patch can have one or more label monomers either directly (covalently or noncovalently) or indirectly attached to it, either prior to or after its attachment to the scaffold.

PROBE. This refers to a molecule that has a target-specific sequence. In the context of a singular nanoreporter, the term "probe" refers to the nanoreporter itself; in the context of a dual nanoreporter, the term "probe" refers to one or both of the two components of the nanoreporter.

PROBE PAIR. The term "probe pair" refers to a dual nanoreporter.

REGISTER. The term "register" refers to a set of alternating label attachment regions.

SELECTIVE BINDING. The term "selective binding" refers to the any preferential binding of a pair of molecules or moieties for each other with respect to other molecules or moieties in a composition that would be recognized by one of skill in the art. In certain embodiments, a pair of molecules or moieties selectively binds when they preferentially bind each other compared to other molecules or moieties. Selective binding can include affinity or avidity, or both, of one molecule or moiety for another molecule or moiety. In particular embodiments, selective binding requires a dissociation constant ($K_D$) of less than about $1\times10^{-5}$ M or less than about $1\times10^{-6}$ M, $1\times10^{-7}$ M, $1\times10^{-8}$ M, $1\times10^{-9}$ M, or $1\times10^{-10}$ M. In contrast, in certain embodiments, non-selective binding has significantly less affinity, for example, a $K_D$ greater than $1\times10^{-3}$ M.

SPOT. A spot, in the context of nanoreporter detection, is the aggregate signal detected from the label monomers attached to a single label attachment site on a nanoreporter, and which, depending on the size of the label attachment region and the nature (e.g., primary emission wavelength) of the label monomer, may appear as a single point source of light when visualized under a microscope. Spots from a nanoreporter may be overlapping or non-overlapping. The nanoreporter code that identifies that target molecule can comprise any permutation of the length of a spot, its position relative to other spots, and/or the nature (e.g., primary emission wavelength(s)) of its signal.

TARGET-SPECIFIC SEQUENCE. The term "target-specific sequence" refers to a molecular entity that is capable of binding a target molecule. In the context of a nanoreporter, the target-specific sequence is attached to the nanoreporter scaffold. The target molecule is preferably (but not necessarily) a naturally occurring molecule or a cDNA of a naturally occurring molecule or the complement of the cDNA.

5.2 The Nanoreporter Scaffold

The nanoreporter scaffold can be any molecular entity, more preferably a nucleic acid molecule, containing label attachment regions to which label monomers can be directly or indirectly attached. In one embodiment, the nanoreporter scaffold is a protein scaffold; in a preferred embodiment, the nanoreporter scaffold is a nucleic acid scaffold in which the label attachment regions are single-stranded regions to which other nucleic acids, such as oligonucleotide patches, RNA patches, or DNA patches, can attach by hybridization. In specific embodiments, the nanoreporter scaffold is a nucleic acid molecule.

There are no particular limitations on the types of scaffolds that are suitable for forming the nanoreporters of the invention. A scaffold according to the invention can essentially have any structure including, for example, single stranded linear scaffold, double stranded linear scaffold, single stranded circular scaffold or double stranded circular scaffold. Examples of scaffold structures include, for example, a scaffold made of one molecular entity such as polypeptides, nucleic acids or carbohydrates. A scaffold may also include a combination of structures, for example, a scaffold may be made of one or more polypeptide stretches coupled to one or more carbohydrate stretches.

Suitable molecular entities for scaffolds according to the invention include polymeric structures particularly nucleic acid based polymeric structures such as DNA. DNA based structures offer numerous advantages in the context of the present invention due at least in part to the vast universe of existing techniques and methodologies that allow manipulation of DNA constructs.

As indicated above, the scaffold may be single stranded or double stranded. Double stranded scaffold can be either conventional double stranded DNA or a double strand that is composed of a linear single stranded stretch of nucleic acid with patch units or flat-patches attached. A scheme for forming a linearized scaffold is depicted in FIG. 8.

A scaffold can have 2, 3, 4, 5, 6, 7, 8, 9, 10, 11, 12, 13, 14, 15, 16, 17, 18, 19, 20, 21-100 label attachment regions or more.

The label attachment regions of a nanoreporter scaffold will vary in size depending on the method of labeling. In various embodiments, a label attachment region has a length anywhere from 10 nm to 10,000 nm, but is more preferably from 50 nm to 5,000 nm, and is more preferably from 100 nm to 1,000 nm. In various embodiments, the label attachment region is from about 100 nm to about 500 nm, from about 150 nm to about 450 nm, from about 200 nm to about 400 nm, or from 250 to about 350 nm. In a preferred embodiment, the label attachment region corresponds closely to the size of a diffraction-limited spot, e.g., the smallest spot that can be detected with standard optics, which is about 300 nm.

Where the scaffold is a nucleic acid, 1 nm corresponds to approximately 3 nucleotides; thus, an approximately 300 nm-label attachment region corresponds to approximately 900 bases. In other preferred embodiments, the label attachment region is from about 300 nucleotides to about 1.5 kb, from about 450 nucleotides to about 1.35 kb, from about 0.6 kb to about 1.2 kb, or from 0.75 kb to about 1.05 kb.

An illustrative example of a molecular entity for a nanoreporter scaffold according to the invention is M13 DNA, which is single-stranded. In one embodiment, the nanoreporter scaffold is circular at least partially single stranded DNA, such as circular M13. In a more preferred embodiment, the nanoreporter scaffold is linear at least partially single stranded DNA, such as linear M13. In a specific embodiment, the M13 single-stranded DNA obtained by operating a cut at the BamH1 site of circular M13 DNA.

It should be noted that within the context of the present invention, linear DNA provides additional advantages compared to circular DNA. One advantage of using linear DNA in forming a scaffold according to the invention relates to the significantly reduced torsional stress associated with linear DNA. The added torsional stress associated with circular DNA may interfere with the structural integrity of the scaffold upon the addition to the scaffold of other components of the nanoreporter, such as patch units. Severe torsional stress may lead to the breaking of the structure of the scaffold. It should be noted however that the nanoreporters where only a few, short label attachment sites are labeled, circular DNA may be suitable.

5.2.1 Novel Synthetic Nanoreporter Scaffold Sequences

The present invention provides nanoreporter scaffold that are artificial nucleic acid molecules (DNA, RNA, or DNA/RNA hybrids) designed to have features that optimize labeling and detection of the nanoreporter. In these aspects of the invention, a nanoreporter scaffold is an artificial nucleic acid comprising one or more synthetic sequences from 50 to 50,000 bases long. Accordingly, the nanoreporter scaffold, which is preferably a DNA, is designed to have one or more regions, useful as label attachment regions, comprising a regular pattern of a particular base (the "regularly-repeated base"). In such regions, the regularly-repeated base occurs with a periodicity of every nth residue, where n is any number, and preferably from 4 to 25.

Preferably, not more than 25% of the regularly-repeated base in a Region appears at other than the regular intervals. For example, if in a Region of 100 nucleotides there are 12 thymidine bases, and thymidine is the regularly-repeated base, in this aspect of the invention not more than 25% of these, i.e., 3 thymidine bases, appear outside the regular pattern of thymidines. In specific embodiments, not more than 20%, not more than 15%, not more than 10%, not more than 9%, not more than 8%, not more than 7%, not more than 6%, not more than 5%, not more than 4%, not more than 3%, not more than 2% or not more than 1% of the base appears at other than the regular intervals in the region.

The regularly-repeated base in the Regions in a nanoreporter scaffold, or its complementary regularly-repeated base in an annealed patch (or segment) can be used to attach label monomers, preferably light emitting label monomers, to the nanoreporter in a regular, evenly spaced pattern for better distribution of the nanoreporter signal. Preferably, where a Region is labeled, at least 50%, at least 60%, at least 70%, at least 80%, at least 90%, at least 95% or at least 98% of occurrences of the regularly-repeated base is attached to at least one light-emitting label monomer, either by covalent attachment of a label monomer to a base, or by hybridization to a nucleic acid in which the complements of the regularly-repeated base are so-labeled.

This percentage of occurrences can be measured by any means known in the art. In one method, the amount of nucleic acid produced in a labeling reaction is purified (for example, RNA can be purified using a Qiagen RNeasy kit) and subjected to UV spectrophotometry. The absorbance ("A") at the appropriate wavelengths is measured for each of the nucleic acid (260 nm) and the label monomer whose occurrence is to be measured (e.g., 495 nm for Alexa Fluor 488; 590 nm for Alexa Fluor 594; 650 for Alexa Fluor 647; and 550 nm for Cy3). The absorbance of the nucleic acid is corrected by adjusting the value of the absorbance at 260 nm ("A260") to remove the "noise" contribution from the label monomer by subtracting the absorbance at the peak wavelength for the label monomer ($A_{LM}$) minus the correction factor for that label monomer. Where the nucleic acid is RNA, the number of label monomers per one thousand nucleotides can be calculated according to the formula:

$$\frac{\text{no. of label monomers}}{1000 \text{ nucleotides}} = \frac{A260}{A_{LM}} \times \frac{9010}{EC_{LM}} \times 1000$$

where $EC_{LM}$ is the extinction coefficient for the label monomer. From this formula, the percentage of occurrences of the regularly-repeated base that are attached to a light-emitting label monomer can be calculated.

Generally, the preferred regularly-repeating base in a label attachment region is thymidine, so that the region can be labeled by hybridization to one or more complementary patches (e.g., RNA segments) in which the regularly-repeated base is uridine. This permits the use of amino-allyl-modified UTPs, which are readily commercially available, as label monomer attachment sites, in an otherwise random sequence. Preferably, in addition to the regular periodicity of the Regions, the regions (and the nucleic acid comprising them) contain minimal secondary structure. The overall GC-content is preferably maintained close to 50%, and is preferably consistent over relatively short stretches to make local Tm's similar.

The artificial nucleic acids of the invention, or at least the Regions therein, preferably do not have direct or inverted repeats that are greater than 12 bases in length. In other embodiments, the artificial nucleic acids and/or Regions do not have direct or inverted repeats that are greater than 11, 10 or 9 bases in length.

In an exemplary Region in which the regularly-repeated nucleotide is a thymidine and a GC content of approximately 50%, excess adenines would make up the loss in abundance of T's. To generate the selected sequence, random sequences with fixed patterns of T's ranging from every $4^{th}$ base to every $25^{th}$ base are created and screened to minimize the presence of inverted and direct repeats.

Sequences are also screened preferably to avoid common six-base-cutter restriction enzyme recognition sites. Selected sequences are additionally subjected to predicted secondary structure analysis, and those with the least secondary structure are chosen for further evaluation. Any program known in the art can be used to predict secondary structure, such as the MFOLD program (Zuker, 2003, Nucleic Acids Res. 31 (13): 3406-15; Mathews et al., 1999, J. Mol. Biol. 288:911-940).

An appropriate sequence is divided into label attachment regions ranging from 50 bases to 2 kilobases long (could be longer). Each label attachment region is a unique sequence, but contains a consistent number and spacing of T's in relation to the other label attachment regions in a given reporter sequence. These label attachment regions can interspersed with other regions whose sequence does not matter. The synthetic label attachment regions in a nanoreporter scaffold can be of different lengths and/or have different regularly-repeated bases. An optimized start sequence for transcription by RNA polymerase T7, T3, or SP6 (beginning at position +1 of the transcript) can be added to the 5' end of each label attachment region. Restriction sites are optionally added at the boundaries of each label attachment region to allow specific addition or deletion of individual label attachment regions to the sequence using conventional cloning techniques. The number of synthetic label attachment regions in a nanoreporter preferably ranges from 1 to 50. In yet other embodiments, the number of synthetic label attachment regions in a nanoreporter ranges from 1, 2, 3, 4, 5, 6, 7, 8, 9, or 10 synthetic label attachment regions to 15, 20, 30, 40, or 50 synthetic label attachment regions, or any range in between.

An example of such a novel synthetic label attachment region is given below. In this sequence, shown 5' to 3', the T's are placed in every $8^{th}$ position and the region is bounded by a 5' Sac I restriction site and a 3' Kpn I restriction site. An optimized transcript start site for T7 polymerase (GGGAGA) is included at the 5' end of the region, downstream of the 5' restriction site. The complement of this sequence, when generated as a single-stranded molecule, forms the scaffold for the RNA molecule transcribed from this label attachment region.

(SEQ ID NO: 1)
GAGCTCGGGAGATGGCGAGCTGGAAGCATCAGAAAGTAGGAAGATGACAA

AATAGGGCCATAGAAGCATGAAGAACTGAACGCATGAGACAATAGGAAGC

TACGCCACTAGGGACCTGAGAAGCTGAGCGGCTCAGCGGGTCCGAGCGTC

AAAAAATAAAAGAGTGAAACAATAGACGAATGACGCGGTAAAACCATCCA

GAAGTAAACGGGTACAAACATACAGAGATAGCCACCTGGACCAATAGGCA

-continued

```
CGTACAAACGTACAAGCCTGGCGCGATGAGGCAATCCACACGTGCAGAGC

TGGAACAATGGAAAGATGCAAGAATAAACCGATACCGGGATCGAGGGCTC

AGCGAATAAAGCAGTCAACAACTGGAAAGATCCACACATACCGGCGTAAC

CGAGTCCAAACATACAGACCTGCAAGACTCGCGACATGGACGGTAAAAC

CATCCGACCGTAAACCGGTAACCAGGTAGCCGGGTAAAAACATAGCAGGG

TGGAGACCTCAGAACGTAAAGACGTCCAAGGGTCGCCGGATAGCGAACTA

CGCGCATCGCCCAATGGGCCAATCAACAGATAAACGAGTAGAAAAGTCAG

AAAATAAGAAACTAACGAAATACGAGGGTCCAAGGATGCAAGACTGAGGC

CCTAAGGAGATAAGGAAATAGGCCGATGCAGACCTGAAACGATGCACCGA

TCCGACGGTAAAAGACTAGACACGTAGCCGGATCAGGGCCTGGGAGGCTG

GAACCGTGAGCACATAGCAAAGTCGCAGCGTCGGCAGATGCGCCGGTAAA

AAAGTAGAGGCATGACCGGATGGGCAAATAGCGACGTACAGCAGTGAAGC

ACTAAAAGCATCCAAGGGTAGGAGACTAGGCGCCTCGACGGGTAGGTACC
```

The synthetic nucleic acids of the present invention can be chemically synthesized using naturally occurring nucleotides or variously modified nucleotides designed to increase the biological stability of the molecules or to increase the physical stability of the duplex formed between the label attachment region and the annealed patches or segments, e.g., phosphorothioate derivatives and acridine substituted nucleotides can be used. Examples of modified nucleotides which can be used to generate the synthetic nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

Alternatively, the synthetic nucleic acid can be produced biologically using a vector into which a nucleic acid has been subcloned.

In various embodiments, the synthetic nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, Bioorganic & Medicinal Chemistry 4(1): 5-23; Perry-O'Keefe et al., 1996, Proc. Natl. Acad. Sci. USA 93: 14670-675.

In an exemplary embodiment, the selected novel synthetic sequence can be constructed synthetically as double-stranded DNA by a commercial gene synthesis company and cloned in an oriented fashion into a "phagemid", a plasmid vector containing an M13 or f1 phage intergenic (IG) region which contains the cis-acting sequences necessary for DNA replication and phage encapsidation, such as pUC119. The appropriate orientation of the cloned insert relative to the phage origin of replication allows for the generation of a single-stranded DNA scaffold which is the reverse complement of the RNA molecules generated by in vitro transcription for each label attachment region.

By way of example, in order to generate the single-stranded DNA scaffold of the novel reporter, the phagemid is transformed into an E. coli strain containing an F' episome. Subsequent infection of the transformed bacteria with a helper phage such as the M13 mutant K07 results in the secretion of the phagemid carrying the novel reporter sequence as a single-stranded, packaged phage from which the circular, single-stranded DNA is prepared using a standard protocol. This DNA is linearized and the vector portion is excised by annealing short, complementary oligonucleotides to either end of the novel reporter sequence to generate double-stranded restriction sites, followed by treatment with the appropriate restriction enzymes.

By way of example, to make the RNA molecules (patches or "segments") for each label attachment region, PCR primers are designed to generate a double-stranded template beginning with an RNA polymerase promoter (T7, T3, or SP6) directly upstream (5') of the transcription start site and ending following the 3' restriction enzyme site. Using this template, in vitro transcription of RNA molecules is performed in the presence of amino-allyl modified regularly-repeated base in the RNA (e.g., UTP) and unmodified other bases (e.g., ATP, CTP and GTP). This leads to an RNA product in which every regularly-repeated base (e.g., U) is modified to allow covalent coupling of a label monomer at that position in the RNA molecule.

Coupling of light-emitting label monomers to the RNA molecules and annealing of the labeled RNA molecules to the scaffold are carried out as described below.

Some design considerations for the de novo sequence are listed in Table 1 below.

TABLE 1

| Feature Of Synthetic Scaffold | Advantages |
|---|---|
| Novel synthetic sequence | Can be of any length and be designed to incorporate any desired sequence feature including but not limited to those listed in this table. |

TABLE 1-continued

| Feature Of Synthetic Scaffold | Advantages |
|---|---|
| Minimal secondary structure (select against inverted repeats) | Allows for consistent transcription of full-length RNA molecules. Allows for consistent annealing of RNA molecules to scaffold at predictable temperatures. Minimizes self-annealing and/or cross-annealing between RNA molecules or scaffolds. |
| Minimal repeated sequences | Avoids mis-annealing between RNA molecules and inappropriate regions of the scaffold. |
| Unique restriction sites at borders of label attachment regions | Allows addition and deletion of individual label attachment regions using standard molecular cloning techniques. |
| Defined, even spacing of T's and transcription with amino-allyl-modified UTP (no unmodified UTP) | Controls number of coupling sites for monomers in each label attachment region, allowing for consistent brightness of individual labeled RNA molecules. Controls distance between monomers: spacing can be optimized to avoid stearic hindrance and fluorescence quenching. |
| Optimized start sequence for transcription by RNA polymerase T7, T3, or SP6 | Promotes efficient in vitro transcription of each label attachment region. |

5.3 Patches

Label monomers that emit signals that constitute all or part of the nanoreporter code are attached to label attachment region(s) of the nanoreporter scaffold through a structure referred to herein as a "patch." The label monomers can be directly (e.g., covalently or noncovalently) attached to a patch, or indirectly attached to a patch (e.g., through hybridization).

Nucleic acid patches can by anywhere from 25 nucleotides to several kilobases (e.g., 5 kb) in length, and are preferably 50 nucleotides to 2 kb in length. In specific embodiments, nucleic acid patches are approximately 25-250, 50-200, 50-150, or 50-100 nucleotides in length. In other embodiments, nucleic acid patches are approximately 500-2,000, 500-1,500, 500-1,000, 750-1,250, or 750-1,000 nucleotides in length. Nucleic acid patches can be RNA patches or DNA patches.

A label monomer can be covalently attached to a patch before or after the patch is attached to the label attachment region of a nanoreporter scaffold. For example, where the patch is a nucleic acid molecule, the label can be covalently attached by incorporation of a nucleotide containing a label monomer into the nucleic acid during its synthesis but before it is attached, e.g., via hybridization, to the label attachment region of the scaffold. Alternatively, during the synthesis of a nucleic acid patch, a nucleotide containing a label monomer acceptor group be included, and the label monomer added to the nucleic acid patch after its synthesis, either before or after it is attached to the label attachment region of the scaffold. Alternatively, the label monomer can be indirectly attached to the patch, for example by hybridization of the patch to a "flap" that serves as a basis for attachment of the label monomer to the nanoreporter.

Thus, where a patch is a nucleic acid, it can range anywhere from 20 nucleotides to more than 5 kb in length, depending on the method of assembly of the nanoreporter.

For example, where a patch has covalently incorporated into it one or more label monomers that emit signals that art part of the nanoreporter code in the context of the labeled nanoreporter, it is preferably about 500-1500 nucleotides in length, and is generally referred to herein as a "segment," a "dark" segment being the patch prior to the incorporation of the label monomer (but, in a preferred embodiment, containing label monomer acceptor sites, such as amino allyl nucleotides), and a "colored" segment being one containing the desired label monomer or label monomers.

Where a patch merely serves as a template for flap attachment to the nanoreporter, then it is preferably smaller in size, for example about 25-250 nucleotides in length, and is most preferably about 50-100 nucleotides in length. Such patches are referred to herein as "oligonucleotide patches." As detailed in Section below, an oligonucleotide is preferably partially complimentary in sequence to a scaffold, such that when it is annealed to the scaffold, an overhang is generated that is complementary to all or portion of a flap.

The terms "segment" and "oligonucleotide patch" are used herein merely for convenience of description; however, there is no size cutoff to distinguish a "segment" from an "oligonucleotide patch." The purpose of both types of structures is to maximize the labeling—and thus signal intensity—from the nanoreporter, thereby allowing for single target molecule detection by a nanoreporter.

In certain aspects, the present invention provides a synthetic molecule, whose configuration is illustrated by reference to FIG. 7A, comprising a strand of a nucleic acid (scaffold) and a plurality of patch pairs hybridized to the strand, where each patch pair comprises an "A" patch and a "B" patch, and, for each patch pair, (a) each "A" patch is an oligonucleotide comprising a first region (1P) and a second region (2P), the first region being (i) at the alpha end of the "A" patch, and (ii) hybridized to a first portion of the strand, the second region being (ii) at the beta end of the "A" patch; (b) each "B" patch is an oligonucleotide comprising a third region (3P) and a fourth region (4P), the third region being (i) at the alpha end of the "B" patch, and (ii) hybridized to the second region of the "A" patch, the fourth region being (i) at the beta end of the "B" patch and (ii) hybridized to a second portion of the strand, the second portion of the strand being to the beta end of the first portion of the strand, where the second region or the third region further comprises at its beta end or alpha end, respectively, a hybridizable region that is not hybridized to the "B" patch or "A" patch, respectively.

Figure 7C:
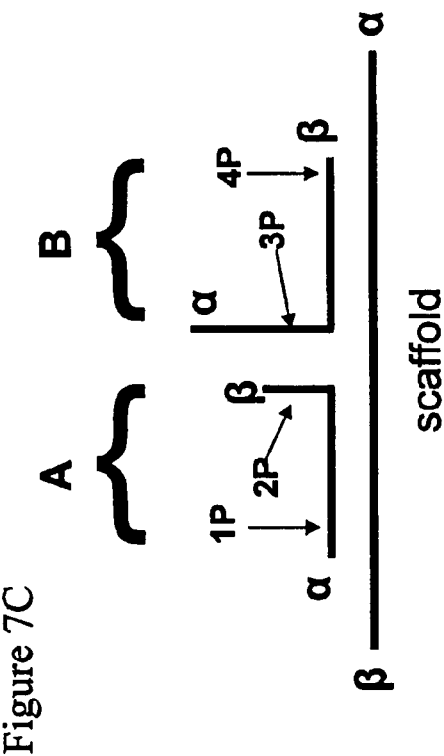
Figure 7D:
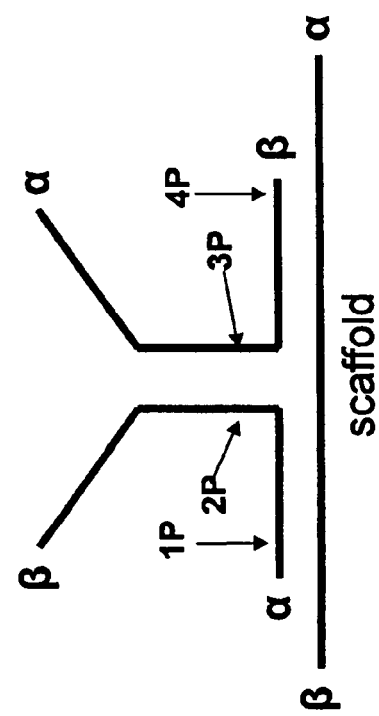
Figure 7A:
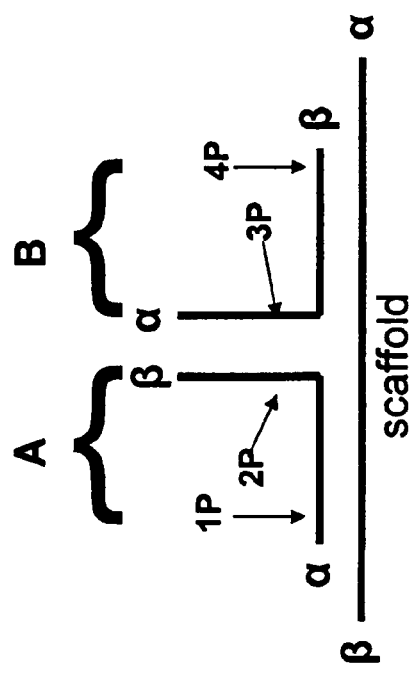
Figure 7B:
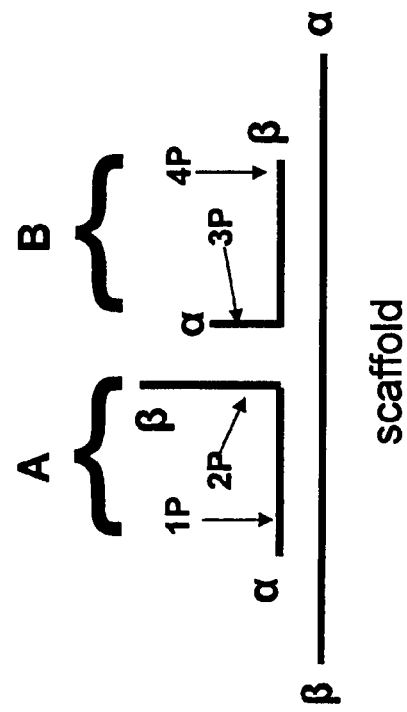

In the synthetic molecule of FIG. 7A, the second region may further comprise at its beta end a hybridizable region that is not hybridized to the "B" patch, as depicted in FIG. 7B, or the third region further comprises at its alpha end a hybridizable region that is not hybridized to the "A" patch, as depicted in FIG. 7C.

The present invention further provides a synthetic molecule, whose configuration is illustrated by reference to FIG.

7D, comprising a strand of a nucleic acid (scaffold) and a plurality of patch pairs hybridized to the strand, where each patch pair comprises an "A" patch and a "B" patch, where, for each patch pair, (a) each "A" patch is an oligonucleotide comprising a first region (1P) and a second region (2P), the first region being (i) at the alpha end of the "A" patch, and (ii) hybridized to a first portion of the strand, the second region being (ii) at the beta end of the "A" patch; (b) each "B" patch is an oligonucleotide comprising a third region (3P) and a fourth region (4P), the third region being (i) at the alpha end of the "B" patch, and (ii) hybridized to the second region of the "A" patch, the fourth region being (i) at the beta end of the "B" patch and (ii) hybridized to a second portion of the strand, the second portion of the strand being to the first of the first portion of the strand, where the second region further comprises at its beta end a first hybridizable region that is not hybridized to the "B" patch, and where the third region further comprises at its alpha end a second hybridizable region that is not hybridized to the "A" patch.

In the synthetic molecule of FIG. 7B, each patch pair can be attached to a flap pair, as depicted in FIG. 7F, where each flap pair comprises an "A" flap and a "B" flap, where, for each flap pair, (a) each "A" flap is an oligonucleotide comprising a first flap region (1F) and a second flap region (2F); the first flap region being at the alpha end of the "A" flap; the second flap region (i) being at the beta end of the "A" flap and (ii) comprising at its beta end a hybridizable region that is not hybridized to the "A" patch, "B" patch or "B" flap; and (b) each "B" flap is an oligonucleotide comprising a third flap region (3F), a fourth flap region (4F), and a fifth flap region (5F); the third flap region being (i) being at the alpha end of the "B" flap and (ii) comprising at its alpha end a hybridizable region that is not hybridized to the "A" patch, "B" patch or "A" flap; the fourth flap region (i) being between the third flap region and the fifth flap region and (ii) hybridized to the first flap region of the "A" flap; the fifth flap region being (i) at the beta end of the "B" flap, and (ii) hybridized to the hybridizable region of the second region of the "A" patch.

In the synthetic molecule of FIG. 7C, each patch pair can be attached to a flap pair, as depicted in FIG. 7E, where each flap pair comprises an "A" flap and a "B" flap, where, for each flap pair, (a) each "A" flap is an oligonucleotide comprising an first flap region (1F), a second flap region (2F), and a third flap region (3F); the "A" flap region being (i) at the alpha end of the "A" flap and (ii) hybridized to the hybridizable region of the third region of the "B" patch; the second flap region being between the first flap region and the third flap region; the third flap region (i) being at the beta end of the "A" flap and (ii) comprising at its beta end a hybridizable region that is not hybridized to the "A" patch, "B" patch or "B" flap, and (b) each "B" flap is an oligonucleotide comprising a fourth flap region (4F) and a fifth flap region (5F); the fourth flap region being (i) being at the alpha end of the "B" flap and (ii) comprising at its alpha end a hybridizable region that is not hybridized to the "A" patch, "B" patch or "A" flap; the fifth flap region being (i) at the beta end of the "B" flap, and (ii) hybridized to the second flap region of the "A" flap.

Figure 7G:
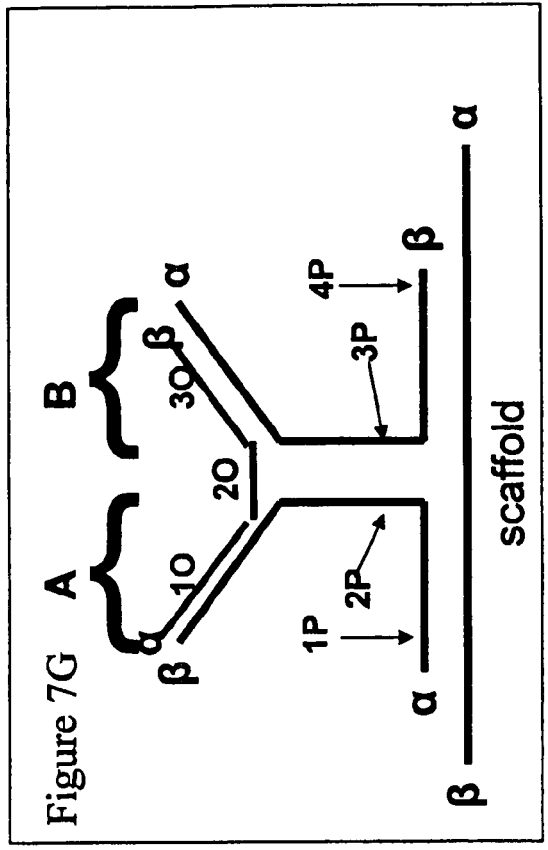
Figure 7E:
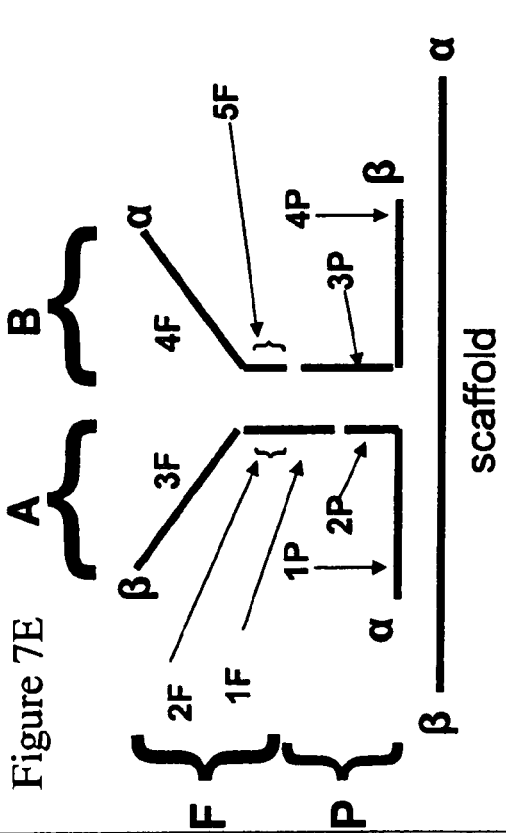
Figure 7F:
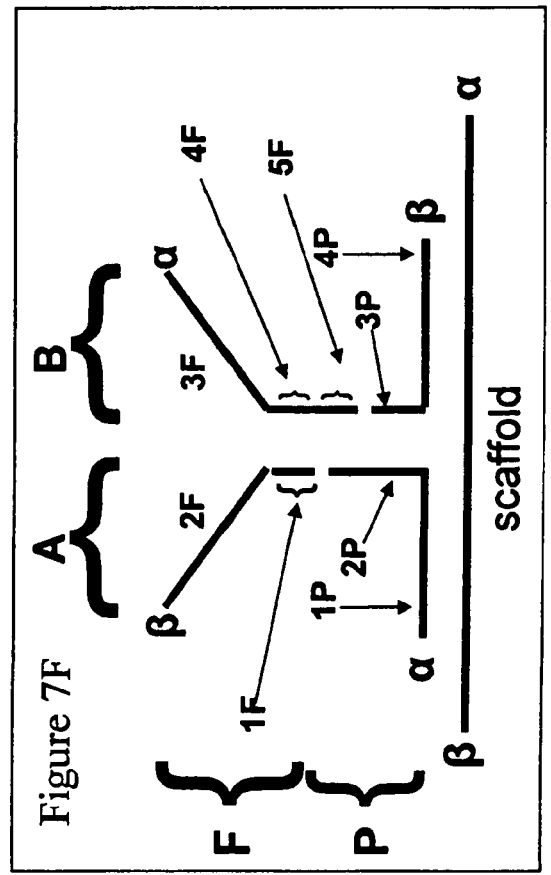

In the synthetic molecule of FIGS. 7D and 7E, the split flaps can be attached one (e.g., (1O)), or more (e.g., (2O) and (3O)) oligonucleotides, as depicted in FIG. 7G. Thus, the one or more oligonucleotides can be attached to the all or a portion of the "A" flap individually (e.g., (1O)), the "B" flap individually (e.g., (3O)), or span all or a portion of each of the "A" flap and "B" flap (e.g., (2O)). Such oligonucleotides are preferably covalently bound to one or more label monomers.

The hybridizable regions of the synthetic molecules may be hybridized to a plurality of oligonucleotides, each bound, preferably covalently bound, to at least one label monomer, more preferably to at least five label monomers. In certain embodiments, all the oligonucleotides attached to a single patch pair comprise the same label monomers, e.g., comprise label monomers that emit light at the same wavelength(s); in specific embodiments, all the oligonucleotides attached to at least two, or at least four, adjacent patch pairs preferably comprise the same label monomers. One or more of the oligonucleotides may be bound to at least one affinity tag.

In certain preferred embodiments, the label monomers are fluorophores or quantum dots.

In the synthetic molecule described above, alpha can refers to either 5' or 3', and the corresponding beta to either 3' or 5', respectively.

The region of complementary in each patch pair, or between a given patch and corresponding flap, is preferably 20-5,000 nucleotides. In certain embodiments, the region of complementary is 20-100 nucleotides, or 5-50 nucleotides.

In the synthetic molecules described above, each flap is preferably 50-5,000 nucleotides in length. In certain embodiments, each flap is 50-150 nucleotides.

The synthetic molecules described above may further comprise a target-specific region which binds to a target molecule. The target-specific region can be attached to the beta or alpha end of the strand.

In certain embodiments, the synthetic molecule described above comprise at least ten patch pairs, or at least fifty patch pairs.

In the synthetic molecules described above, the strand, or scaffold, can be a linearized vector, such as linearized M13.

The synthetic molecule described above may further comprise (a) a first label attachment region to which are attached (directly or indirectly) one or more label monomers that emit light constituting a first signal; (b) a second label attachment region, which is non-overlapping with the first label attachment region, to which is attached one or more label monomers that emit light constituting a second signal; (c) a third label attachment region, which is non-overlapping with the first and second label attachment regions, to which is attached one or more label monomers that emit light constituting a third signal; where each attachment region comprises a plurality of patch pairs; wherein the first and second signals are spectrally distinguishable; wherein the second and third signals are spectrally distinguishable; wherein the first and second signals are not spatially resolvable under conditions that can be used to detect the first, second and third signals; wherein the second and third signals are not spatially resolvable under conditions that can be used to detect the first, second and third signals; wherein the first and third signals are spatially resolvable under conditions that can be used to detect the first, second and third signals; and wherein the identities of the first, second and third signals and the locations of the first and third signal relative to each other constitute at least part of a code that identifies the target molecule.

5.4 Label Monomers

The nanoreporters of the present invention can be labeled with any of a variety of label monomers, such as a radioisotope, fluorochrome, dye, enzyme, nanoparticle, chemiluminescent marker, biotin, or other monomer known in the art that can be detected directly (e.g., by light emission) or indirectly (e.g., by binding of a fluorescently-labeled antibody). Generally, one or more of the label attachments regions in the nanoreporter is labeled with one or more label monomers, and the signals emitted by the label monomers attached to the label attachment regions of a nanoreporter constitute a code that identifies the target to which the target-specific region of the nanoreporter binds. In certain embodiments, the lack of a given signal from the label attachment region (i.e., a "dark" spot) can also constitute part of the nanoreporter code. An example of a dark spot is depicted at position 12 of the nanoreporter in FIG. 1A.

Radioisotopes are an example of label monomers that can be utilized by the invention. Several radioisotopes can be used as label monomers for labeling nucleotides or proteins, including, for example, $^{32}P$, $^{33}P$, $^{35}S$, $^{3}H$, and $^{125}I$. These radioisotopes have different half-lives, types of decay, and levels of energy which can be tailored to match the needs of a particular experiment. For example, $^{3}H$ is a low energy emitter which results in low background levels, however this low energy also results in long time periods for autoradiography. Radioactively labeled ribonucleotides, deoxyribonucleotides and amino acids are commercially available. Nucleotides are available that are radioactively labeled at the first, or a, phosphate group, or the third, or γ, phosphate group. For example, both [$\alpha$-$^{32}P$] dATP and [$\gamma$-$^{32}P$] dATP are commercially available. In addition, different specific activities for radioactively labeled nucleotides are also available commercially and can be tailored for different experiments.

Another example of label monomers that can be utilized by the invention are fluorophores. Several fluorophores can be used as label monomers for labeling nucleotides including, for example, fluorescein, tetramethylrhodamine, and Texas Red. Several different fluorophores are known, and more continue to be produced, that span the entire spectrum. Also, different formulations of the same fluorophore have been produced for different applications. For example, fluorescein, can be used in its isothiocynanate form (FITC), as mixed isomer or single isomer forms of carboxyfluorescein succinimidyl ester (FAM), or as isomeric dichlorotriazine forms of fluorescein (DTAF). These monomers are chemically distinct, but all emit light with a peak between 515-520 nm, thereby generating a similar signal. In addition to the chemical modifications of fluorescein, completely different fluorophores have been synthesized that have the same or very similar emission peaks as fluorescein. For example, the Oregon Green dye has virtually superimposable excitation and emission spectra compared to fluorescein. Other fluorophores such as Rhodol Green and Rhodamine Green are only slightly shifted in their emission peaks and so also serve functionally as substitutes for fluorescein. In addition, different formulations or related dyes have been developed around other fluorophores that emit light in other parts of the spectrum.

Non-radioactive and non-fluorescent label monomers are also available. For example, biotin can be attached directly to nucleotides and detected by specific and high affinity binding to avidin or streptavidin which has been chemically coupled to an enzyme catalyzing a colorimetric reaction (such as phosphatase, luciferase, or peroxidase). Digoxigenin labeled nucleotides can also similarly be used for non-isotopic detection of nucleic acids. Biotinylated and digoxigenin-labeled nucleotides are commercially available.

Very small particles, termed nanoparticles, also can be used as label monomers to label nucleic acids. These particles range from 1-1000 nm in size and include diverse chemical structures such as gold and silver particles and quantum dots.

When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light which when superimposed will give a specific, unique color. The particles are being manufactured by companies such as Genicon Sciences. Derivatized silver or gold particles can be attached to a broad array of molecules including, proteins, antibodies, small molecules, receptor ligands, and nucleic acids. For example, the surface of the particle can be chemically derivatized to allow attachment to a nucleotide.

Another type of nanoparticle that can be used as a label monomer are quantum dots. Quantum dots are fluorescing crystals 1-5 nm in diameter that are excitable by a large range of wavelengths of light. These crystals emit light, such as monochromatic light, with a wavelength dependent on their chemical composition and size. Quantum dots such as CdSe, ZnSe, InP, or InAs possess unique optical properties.

Many dozens of classes of particles can be created according to the number of size classes of the quantum dot crystals. The size classes of the crystals are created either 1) by tight control of crystal formation parameters to create each desired size class of particle, or 2) by creation of batches of crystals under loosely controlled crystal formation parameters, followed by sorting according to desired size and/or emission wavelengths. Use of quantum dots for labeling particles, in the context of the present invention, is new, but is old in the art of semiconductors. Two examples of earlier references in which quantum dots are embedded within intrinsic silicon epitaxial layers of semiconductor light emitting/detecting devices are U.S. Pat. Nos. 5,293,050 and 5,354,707 to Chapple Sokol, et al., which are hereby incorporated by reference herein in their entireties.

In specific embodiments, one or more of the label attachments regions in the nanoreporter is labeled with one or more light-emitting dyes, each label attachment region containing, directly or indirectly, one or more label monomers. The light emitted by the dyes can be visible light or invisible light, such as ultraviolet or infra red light. In exemplary embodiments, the dye is a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-($\epsilon$-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA Fluor™; Cyt; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; Alexa Fluor 350; Alexa Fluor 488; Alexa Fluor 532; Alexa Fluor 546; Alexa Fluor 568; Alexa Fluor 594; or Alexa Fluor 647.

The label monomers can be incorporated into a nanoreporter at different stages of its assembly, or into a component (e.g., a "flap" of the nanoreporter prior to its assembly into the nanoreporter).

A label monomer can be directly attached to a nucleotide using methods well known in the art. Nucleotides can also be chemically modified or derivitized in order to attach a label monomer. For example, a fluorescent monomer such as a fluorescein molecule can be attached to dUTP (deoxyuridinetriphosphate) using a four-atom aminoalkynyl group. Each label monomer is attached to a nucleotide making a label monomer: nucleotide complex.

This label monomer: nucleotide complex can be incorporated into nucleic acids (for example, a DNA patch or a detection oligonucleotide) in a variety of ways. For example, a label monomer: nucleotide complex can be incorporated at only one location within a nucleic acid or at two or more locations within a nucleic acid.

Amine-reactive and thiol-reactive fluorophores are available and used for labeling nucleotides and biomolecules. Generally, nucleotides are fluorescently labeled during chemical synthesis, for example, incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum.

A nucleotide can be attached to a label monomer first and then be incorporated into a nucleic acid. Alternatively, an existing nucleic acid can be labeled by attaching a label monomer to a nucleotide within the nucleic acid. For example aminoallyl- ("AA-") modified UTP nucleotides can be incorporated into the RNA product during transcription. In various embodiments, 20% or more of UTP nucleotides in a transcription reaction to generate RNA patches are AA modified. In various embodiments, about 20%-100%, 20%-80%, 30-80%, 40-60% or 50%-75% of UTPs in a transcription reaction are AA-modified, in a preferred embodiment, approximately 50% of UTPs in a transcription reaction are AA-modified.

In addition, for example, different types of label monomer: nucleotide complexes can be incorporated into a single acid nucleic acid, where one component of the nanoreporter code comprises more than one type of signal.

Fluorescent dyes that can be bound directly to nucleotides can also be utilized as label monomers. For example, FAM, JOE, TAMRA, and ROX are amine reactive fluorescent dyes that have been attached to nucleotides and are used in automated DNA sequencing. These fluorecently labeled nucleotides, for example, ROX-ddATP, ROX-ddCTP, ROX-ddGTP and ROX-ddUTP, are commercially available.

Other types of label monomers that may be used to label a nanoreporter are quantum dots. Due to their very small size the quantum dots can be coupled into oligonucleotides directly without affecting the solubility or use of the oligonucleotide. In a preferred embodiment, only one oligonucleotide molecule is coupled to each nanoparticle. To synthesize an oligonucleotide-nanoparticle complex in a 1:1 ratio by conventional batch chemistry, both the oligonucleotide and the nanoparticle require a single reactive group of different kinds that can be reacted with each other. For example, if an oligonucleotide has an amino group and a nanoparticle has an aldehyde group, these groups can react to form a Schiff base. An oligonucleotide can be derivitized to attach a single amino or other functional group using chemistry well known in the art. However, when a nanoparticle is derivatized, it is covered with a chemical reagent which results in coating the entire surface of the nanoparticle with several functional groups.

The invention provides a method of coupling one oligonucleotide to one nanoparticle by chemically coupling the oligonucleotide on a solid surface such as the glass support used for the oligonucleotide synthesis.

For example, commercially available resins for oligonucleotide synthesis such as long chain alkylamino controlled pore glass (lcaa CPG) can be used.

Alternatively, a flat surface such as a derivitized microscope slide can be used. The surface density of the nascent oligonucleotide chains should be lower than the diameter of the nanoparticle. This can be achieved by either choosing a glass support with low surface density of the reactive groups, or by using diluted reagent for the first step of the oligonucleotide synthesis so that the surface is not saturated. Another point of consideration when using the standard glass matrices for oligonucleotide synthesis is to use a pore diameter higher than the nanoparticle diameter to ensure the flow of the reagents. For example, an oligonucleotide can be synthesized on a diluted basis relative to the solid support, for example one tenth of a normal synthesis, to ensure good spacing of the oligonucleotides on the glass support. After the oligonucleotide is synthesized with a reactive functional group, for example, an amino group, derivitized nanoparticles are passed over the glass support to react with the oligonucleotides. A sufficiently large pore size of the glass support can be chosen to prevent clogging with nanoparticles. For example, a pore size of about 200 nm can be used. After the reaction is complete, un-reacted groups on the nanoparticle can be blocked and the complexes can be uncoupled from the glass support.

5.5 The Nanoreporter Code

5.5.1 Dual Nanoreporters

A nanoreporter whose components exist in two molecular entities is referred to as a dual nanoreporter. In a dual nanoreporter, generally each component contains a target-specific sequence, which improves the specificity of and binding kinetics of the nanoreporter to its target. The two different target-specific sequences are designed or selected such that each recognizes a different portion of a target molecule.

FIGS. 1A-1C illustrates embodiments of the invention involving dual nanoreporters. In FIGS. 1A and 1B, each of the two component of the nanoreporter is labeled, such that the nanoreporter's spectral code is formed only when the two components of the nanoreporter come together upon binding of the dual nanoreporter to its target molecule. However, in a dual nanoreporter, it is not necessary that both components are labeled. For example, as depicted in FIG. 1C, one component of a dual nanoreporter is labeled with the nanoreporter code, and the other component attached to an affinity tag (arrow) that is useful to immobilize the nanoreporter for stretching and visualization.

5.5.2 Registers

The term "register" refers to a set of alternating (every other) label attachment regions. Registers are useful where it is desirable to label adjacent label attachment regions without a spacer region, and where the signal emanating from adjacent label attachment regions cannot be spatially resolved using the desired method of detection. Thus, the signals detected with use of a register is that form by the alternating, rather than adjacent, label attachment regions. Signals detected from a plurality of registers (e.g., that together are all the label attachment regions) can be combined to form a nanoregister code. Generally when using registers, adjacent label attachment regions are labeled with spectrally distinguishable label monomers.

Examples of registers are depicted in FIGS. 3 and 5. For example, in FIGS. 3A-3B, there are eight label attachment regions 1-8. Alternating label attachment regions 1, 3, 5 and 7 form one register, and label attachment regions 2, 4, 6 and 8 form another register. In FIG. 3A, only one of the registers (1, 3, 5 and 7) is labeled; in FIG. 3B, both registers are labeled.

5.6 Affinity Tags

A variety of affinity tags known in the art may be used to purify and/or immobilize nanoreporters. Where an affinity tag is used to immobilize a nanoreporter for the purpose of detection or imaging, it may be referred to herein as an "anchor." In a preferred embodiment, a biotin anchor is attached to the nanoreporter, allowing immobilization of the nanoreporter on a streptavidin coated slide.

Non-limiting examples of suitable affinity tags are provided below. It should be understood that most affinity tags could serve dual purposes: both as anchors for immobilization of the nanoreporters and tags for purification of the nanoreporters (whether fully or only partially assembled) or their components.

In certain embodiments, the affinity tag is a protein monomer. Examples of protein monomers include, but are not limited to, the immunoglobulin constant regions (see Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the E. coli maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Other affinity tags are recognized by specific binding partners and thus facilitate isolation and immobilization by affinity binding to the binding partner, which can be immobilized onto a solid support. For example, the affinity tag can be an epitope, and the binding partner an antibody. Examples of such epitopes include, but are not limited to, the FLAG epitope, the myc epitope at amino acids 408-439, the influenza virus hemagglutinin (HA) epitope, or digoxigenin ("DIG"). In other embodiments, the affinity tag is a protein or amino acid sequence that is recognized by another protein or amino acid, for example the avidin/streptavidin and biotin.

In certain instances, the affinity tag can be used for labeling a nanoreporter in addition to purifying or immobilizing the nanoreporter. As will be appreciated by those skilled in the art, many methods can be used to obtain the coding region of the affinity tags, including but not limited to, DNA cloning, DNA amplification, and synthetic methods. Some of the affinity tags and reagents for their detection and isolation are available commercially.

5.7 Target-Specific Sequences

The term "target-specific sequence" refers to a molecular entity that is capable of binding a target molecule. In the context of a nanoreporter, the target-specific sequence is attached to the nanoreporter scaffold. The target specific sequence is generally an amino acid sequence (i.e., a polypeptide or peptide sequence) or a nucleic acid sequence. In specific embodiments, where the target-specific sequence is an amino acid sequence, the target-specific sequence is an antibody fragment, such as an antibody Fab' fragment, a single chain Fv antibody.

The target-specific sequence is preferably a nucleic acid sequence, and is most preferably within an oligonucleotide that is either covalently attached (e.g., by ligation) or noncovalently attached (e.g., by hybridization) to the nanoreporter scaffold. A target-specific nucleic acid sequence is preferably at least 15 nucleotides in length, and more preferably is at least 20 nucleotides in length. In specific embodiments, the target-specific sequence is approximately 10-500, 20-400, 30-300, 40-200, or 50-100 nucleotides in length. In other embodiments, the target-specific sequence is approximately 30-70, 40-80, 50-90, or 60-100, 30-120, 40-140, or 50-150 nucleotides in length.

5.8 Target Molecules

The term "target molecule" refers to a molecule that is detected or measured by binding of a labeled nanoreporter whose target-specific sequence(s) recognize (are specific binding partners thereto). A target molecule can be, but is not limited to, any of the following: DNA, cDNA, RNA, mRNA, peptide, a polypeptide/protein (e.g., a bacterial or viral protein or an antibody), a lipid, a carbohydrate, a glycoprotein, a glycolipid, a small molecule, an organic monomer, or a drug. Generally, a target molecule is a naturally occurring molecule or a cDNA of a naturally occurring molecule or the complement of said cDNA.

A target molecule can be part of a biomolecular sample that contains other components or can be the sole or major component of the sample. A target molecule can be a component of a whole cell or tissue, a cell or tissue extract, a fractionated lysate thereof or a substantially purified molecule. The target molecule can be attached in solution or solid-phase, including, for example, to a solid surface such as a chip, microarray or bead. Also, the target molecule can have either a known or unknown structure or sequence.

In certain specific embodiments, that target molecule is not a chromosome. In other specific embodiments, the target molecule is no greater than 1,000 kb (or 1 mb) in size, no greater than 500 kb in size, no greater than 250 kb in size, no greater than 175 kb in size, no greater than 100 kb in size, no greater than 50 kb in size, no greater than 20 kb in size, or no greater than 10 kb in size. In yet other specific embodiments, the target molecule is isolated from its cellular milieu.

In specific, non-limiting embodiments, the target molecule is an antigen such as alpha fetoprotein, alpha-1 antitrypsin, α-2 macroglobulin, adiponectin, apolipoprotein-A-1, apolipoprotein-CIII, apolipoprotein-H, BDNF, β-2 microglobulin, C reactive protein, calcitonin, cancer antigen 19-9, cancer antigen 125, CEA, CD 40, CD 40 ligand, complement 3, CK-MB, EGF, ENA-78, endothelin-1, enrage, eotaxin, erythropoietin, Factor VII, FABP, ferritin, FGF-basic, fibrinogen, G-CSF, GST, GM-CSF, growth hormone, haptoglobin, ICAM-1, IFN-gamma, IgA, IgE, IGF-1, IgM, IL-1α, IL-1β, IL-1ra, IL-2, IL-3, IL-4, IL-5, IL-6, IL-7, IL-8, IL-10, IL-12 p40, IL-12 p70, IL-13, IL-15, IL-16, insulin, leptin, lipoprotein (a), lymphotactin, MCP-1, MDC, MIP-1α, MIP-1β, MMP-2, MMP-3, MMP-9, myeloperoxidase, myoglobin, PAI-1, PAP, PAPP-A, SGOT, SHBG, PSA (free), RANTES, serum amyloid P, stem cell factor, TBG, thrombopoietin, TIMP-1, tissue factor, TNF-α, TNF-β, TNF RII, TSH, VCAM-1, VEGF, or vWF.

In some embodiments, the target molecule is an autoimmune related molecule such as ASCA, β-2 glycoprotein, C1q, centromere Prot. B, collagen type 1, collagen type 2, collagen type 4, collagen type 6, Cyto P450, ds DNA, histone, histone H1, histone H2A, histone H2B, histone H3, histone H4, HSC-70, HSP-32, HSP-65, HSP-71, HSP-90α, HSP-90β, insulin, JO-1, mitochondrial, myeloperoxidase, pancreatic islet cells, PCNA, PM-1, PR3, ribosomal P, RNP-A, RNP-C, RNP, Sel-70, Smith, SSA, SSB, T3, T4, thyroglobulin, tTG, (celiac disease), or thyroid microsomal.

In some embodiments, the target molecule is a component isolated from an infectious disease, such as Cholera Toxin, Cholera Toxin β, *Campylobacter jejuni*, cytomegalovirus, Diptheria toxin, Epstein-Barr NA, Epstein-Barr EA, Epstein-Barr VCA, *Heliobacter pylori*, HBV core, HBV envelope, HBV surface (Ad), HBV surface (Ay), HCV core, HCV NS3, HCV NS4, HCV NS5, hepatitis A, hepatitis D, HEV orf2 3KD, HEV orf2 6 KD, HEV orf 3KD, HIV-1 p24, HIV-1 gp41, HIV-1 gp120, HPV, HSV-1/2, HSV-1 gD, HSV-2 gD, HTLV-1/2, influenza A, influenza A H3N2, influenza B, *Leishmania donorani*, Lyme disease, mumps, *M. pneumonia, M tuberculosis*, parainfluenza 1, parainfluenza 2, parainfluenza 3, polio virus, RSV, Rubella, Rubeola, Streptolysin O, Tetanus Toxin, *T. pallidum* 15 kD, *T. pallidum* p47, *T. cruzi*, Toxoplasma, Varicella zoster.

5.9 Nanoreporter Populations

The present invention provides nanoreporter or nanoreporter label unit populations, for example nanoreporter or nanoreporter label unit libraries, that contain at least 10, at least 15, at least 20, at least 25, at least 30, at least 40, at least 50, at least 75, at least 100, at least 200, at least 300, at least 400, at least 500, at least 750, or at least 1,000 unique nanoreporters or nanoreporter label units, respectively. As used herein, "unique" when used in reference to a nanoreporter or nanoreporter label units within a population is intended to mean a nanoreporter or label unit that has a code that distinguishes it from other nanoreporters or label units in the same population.

In specific embodiments, the present invention provides nanoreporter populations with at least 5,000, at least 10,000, at least 20,000 or at least 50,000 unique nanoreporters or nanoreporter label units. The nanoreporters in a population of nanoreporters can be singular nanoreporters, dual nanoreporters, or a combination thereof. The nanoreporters can be labeled or unlabeled.

The size of a nanoreporter population and the nature of the target-specific sequences of the nanoreporters within it will depend on the intended use of the nanoreporter. Nanoreporter populations can be made in which the target-specific sequences correspond to markers of a given cell type, including a diseased cell type. In certain embodiments, nanoreporters populations are generated in which the target-specific sequences represent at least 0.1%, at least 0.25%, at least 0.5%, at least 1%, at least 2%, at least 3%, at least 4%, at least 5%, at least 10%, at least 15%, at least 20%, at least 25%, at least 30%, at least 40%, at least 50%, at least 60%, or at least 70% of the different type of transcripts in a cell. In certain embodiments, nanoreporters populations are generated in which the target-specific sequences represent at least 0.1%, at least 0.25%, at least 0.5%, at least 1%, at least 2%, at least 3%, at least 4%, at least 5%, at least 10%, at least 15%, at least 20%, at least 25%, at least 30%, at least 40%, at least 50%, at least 60%, or at least 70% of the different genes in a cell. In yet other embodiments, nanoreporter populations are generated in which at least some of the target-specific sequences represent rare transcripts in a cell or tissue. Such nanoreporter populations preferably represent at least 5 rare transcripts. In specific embodiments, such nanoreporter populations represent at least 10, at least 20, at least 30, at least 40 or at least 50 rare transcripts. In a specific embodiment, the cell or tissue is a mammalian cell or tissue, and more preferably is a human cell or tissue.

In certain embodiments, the nanoreporter population is a diagnostic or prognostic nanoreporter population. For example, a diagnostic nanoreporter population can be generated that is useful for screening blood products, in which the target-specific sequences bind to the nucleic acids of contaminating viruses such the hepatitis B, hepatitis C, and the human immunodeficiency virus. Alternatively, the diagnostic nanoreporter population may contain target-specific sequences corresponding to cellular disease markers, such as tumor antigens. Prognostic nanoreporter populations generally include target-specific markers that represent different stages of a given disease such as cancer. By selecting appropriate target-specific sequences, a nanoreporter population can be used both to diagnose and prognose disease.

5.10 Biomolecular Samples

The nanoreporter systems of the invention can be used to detect target molecules in any biomolecular sample. As will be appreciated by those skilled in the art, the sample may comprise any number of things, including, but not limited to, cells (including both primary cells and cultured cell lines), tissues and bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen), a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellular fluids, extracellular supernatants from cell cultures, inclusion bodies in bacteria, cellular compartments, cellular periplasm, mitochondria compartment, etc.

The biomolecular samples can be indirectly derived from biological specimens. For example, where the target molecule of interest is a cellular transcript, e.g., a messenger RNA, the biomolecular sample of the invention can be a sample containing cDNA produced by a reverse transcription of messenger RNA. In another example, the biomolecular sample of the invention is generated by subjecting a biological specimen to fractionation, e.g., size fractionation or membrane fractionation.

The biomolecular samples of the invention may be either "native," i.e., not subject to manipulation or treatment, or "treated," which can include any number of treatments, including exposure to candidate agents including drugs, genetic engineering (e.g., the addition or deletion of a gene), etc.

5.11 Separation of Label Monomers

In addition to detecting an overall signal generated from a labeled nanoreporter, the invention provides for the determination of the spatial location of signals emanating from the label monomers (i.e., spots) on a nanoreporter, each spot representing the aggregate signal from label monomers attached to a given label attachment region. A spot may contain signals of the same wavelength or of different wavelengths. Thus, the nature of the spots on a nanoreporter and their location constitutes the nanoreporter code.

Any of a variety of means can be used to "stretch" the nanoreporter to separate the individual spots. For example, a nanoreporter can be stretched using a flowstretch technique (Henegariu et al., 2001, Biotechniques 31:246-250), a receding meniscus technique (Yokota et al., 1997, Nuc. Acids Res. 25:1064-1070) or an electrostretching technique (Matsuura et al., 2001, Nuc. Acids Res. 29: E79).

The use of flow-stretching, receding meniscus, or electro-stretching techniques allows for the separation of the label attachment regions within a nanoreporter so that one can determine spatially where a particular signal is positioned in the nanoreporter. Therefore, unique nanoreporters that have the same combination of label monomers and the same overall signal can be differentiated from one another based on the location of those label monomers within the nanoreporter.

This ability to locate the position of a label attachment region or spot within a nanoreporter allows for the position of the signal(s) emitted by the label monomers in each label attachment region to be used as a distinguishing characteristic when generating a set of unique nanoreporters. Hence, a complex set of nanoreporters can be generated using the same combination of starting label monomers by varying the positions of the label monomers within a nanoreporter.

Prior to stretching a nanoreporter, it is preferable to immobilize the nanoreporter to a solid surface using an affinity tag, as described in Section 5.6 above. In certain aspects of the invention, one end of a nanoreporter is immobilized, either through specific or non-specific binding to a solid surface, the nanoreporter is stretched, and then the other end of the reporter is immobilized, also either through specific or non-specific binding to a solid surface. Accordingly, the nanoreporter is "frozen" in its stretched, or extended, state, to facilitate resolution of the nanoreporters code by detecting and/or imaging the signals emitted by the label monomers attached to a nanoreporter and their locations relative to one another. These aspects of the invention are described below.

5.12 Nanoreporters

In the methods, the nanoreporters are certain types of macromolecules. In certain embodiments, the macromolecule is a macromolecule that is capable of being extended in the methods of the invention. In certain embodiments, the macromolecule is capable of being immobilized in one or two portions as described in the sections below.

In certain embodiments, the nanoreporter is a polysaccharide, a polypeptide or a polynucleotide. Useful polynucleotides include ribonucleic acids, deoxyribonucleic acids and other polynucleotides known to those of skill in the art.

The nanoreporter can be of any size that is sufficient to allow extension and immobilization of the nanoreporter according to the methods of the invention. In certain embodiments when the nanoreporter is a polynucleotide, the nanoreporter can have a length of greater than 500 bp, greater than 750 bp, greater than 1 kb, greater than 1.5 kb, greater than 2.0 kb, greater than 2.5 kb, greater than 3.0 kb, greater than 4.0 kb or greater than 5.0 kb. In certain embodiments, when the nanoreporter is a polypeptide, the nanoreporter can have a size of greater than 50 amino acids, greater than 100 amino acids, greater than 200 amino acids, greater than 300 amino acids, greater than 400 amino acids, greater than 500 amino acids, greater than 750 amino acids, greater than 1000 amino acids, greater than 1500 amino acids, greater than 2000 amino acids, greater than 2500 amino acids, greater than 3000 amino acids, greater than 4000 amino acids or greater than 5000 amino acids. In certain embodiments, when the nanoreporter is a polysaccharide, the nanoreporter can have a size of greater than 50 saccharides, greater than 100 saccharides, greater than 200 saccharides, greater than 300 saccharides, greater than 400 saccharides, greater than 500 saccharides, greater than 750 saccharides, greater than 1000 saccharides, greater than 1500 saccharides, greater than 2000 saccharides, greater than 2500 saccharides, greater than 3000 saccharides, greater than 4000 saccharides or greater than 5000 saccharides.

The nanoreporter can be a native nanoreporter as understood by those of skill in the art, or the nanoreporter can be a non-native nanoreporter. In certain embodiments, when the nanoreporter is a polypeptide, the nanoreporter can comprise only naturally occurring amino acids, or the nanoreporter can comprise naturally occurring amino acids and non-naturally occurring amino acids. The other amino acids can be any amino acids, or derivatives or analogs thereof, known to those of skill in the art. In certain embodiments, when the nanoreporter is a polynucleotide, the polynucleotide can comprise only naturally occurring nucleotides, or the polynucleotide can comprise naturally occurring nucleotides and non-naturally occurring nucleotides. In certain embodiments, when the nanoreporter is a polysaccharide, the polysaccharide can comprise only naturally occurring saccharides, or the polysaccharide can comprise naturally occurring saccharides and non-naturally occurring saccharides. In certain embodiments, the polymers can comprise only non-natural monomers. In further embodiments, the nanoreporter can comprise a plurality of classes of monomers, such as amino acids, nucleotides and/or saccharides.

In certain embodiments, the nanoreporter comprises only one primary, covalently linked chain of monomers. For instance, when the nanoreporter is a polypeptide, in certain embodiments, the nanoreporter-comprises only one primary amino acid chain. When the nanoreporter is a polynucleotide, in certain embodiments, the nanoreporter is single stranded. In further embodiments, the nanoreporter comprises two primary, covalently linked chains of monomers. For instance, when the nanoreporter is a polypeptide, in certain embodiments, the nanoreporter comprises two primary amino acid chains. When the nanoreporter is a polynucleotide, in certain embodiments, the nanoreporter comprises two polynucleotide strands; in certain embodiments, the nanoreporter can be double stranded, in part or in whole. In further embodiments, the nanoreporter comprises three or more primary, covalently linked chains of monomers. For instance, when the nanoreporter is a polypeptide, in certain embodiments, the nanoreporter comprises three primary amino acid chains. When the nanoreporter is a polynucleotide, in certain embodiments, the nanoreporter comprises three polynucleotide strands. For instance, the nanoreporter can comprise three strands F1, X and F2 where a portion of strand X is complementary to strand F1 and a portion of strand X is complementary to strand F2. An example is illustrated in FIG. 13A. In certain embodiments, the nanoreporter comprises more than three primary, covalently linked chains of monomers.

Advantageously, a nanoreporter of the invention can comprise one or more labels that facilitate the detection, imaging or identification of the nanoreporter by techniques known to those of skill in the art. The label can be any detectable moiety known to those of skill in the art. Exemplary labels for nanoreporters include detectable isotopes, radioisotopes, fluors, dyes, enzymes, ligands, receptors, antigens, antibodies, lectins, carbohydrates, nucleotide sequences, and any other detectable label apparent to those of skill in the art. Useful labels, macromolecules comprising labels, and methods of their preparation are described in U.S. provisional patent application No. 60/753,758, entitled "Nanoreporters and Methods of Manufacturing and Use Thereof," filed Dec. 23, 2005, the contents of which are hereby incorporated by reference herein in their entirety.

In certain embodiments, a polynucleotide is a polymer of natural (e.g., A, G, C, T, U) or synthetic nucleobases, or a combination of both. The backbone of the polynucleotide can be composed entirely of "native" phosphodiester linkages, or it may contain one or more modified linkages, such as one or more phosphorothioate, phosphorodithioate, phosphoramidate or other modified linkages. As a specific example, a polynucleotide may be a peptide nucleic acid (PNA), which contains amide interlinkages. Additional examples of synthetic bases and backbones that can be used in conjunction with the invention, as well as methods for their synthesis can be found, for example, in U.S. Pat. No. 6,001,983; Uhlman & Peyman, 1990, *Chemical Review* 90(4):544 584; Goodchild, 1990, *Bioconjugate Chem.* 1(3):165 186; Egholm et al., 1992, *J. Am. Chem. Soc.* 114:1895 1897; Gryaznov et al., *J. Am. Chem. Soc.* 116:3143 3144, as well as the references cited in all of the above. Common synthetic nucleobases of which polynucleotides may be composed include 3-methlyuracil, 5,6-dihydrouracil, 4 thiouracil, 5 bromouracil, 5-thorouracil, 5-iodouracil, 6-dimethyl aminopurine, 6-methyl aminopurine, 2-aminopurine, 2,6-diamino purine, 6-amino-8-bromopurine, inosine, 5-methylcytosine, 7-deazaadenine, and 7-deazaguanosine. Additional non-limiting examples of synthetic nucleobases of which the target nucleic acid may be composed can be found in Fasman, *CRC Practical Handbook of Biochemistry and Molecular Biology,* 1985, pp. 385-392; *Beilstein's Handbuch der Organischen Chemie*, Springer Verlag, Berlin and Chemical Abstracts, all of which provide references to publications describing the structures, properties and preparation of such nucleobases.

The nanoreporter can be prepared according to any technique apparent to those of skill in the art. Advantageously, nanoreporters according to the invention can comprise labels and/or members of binding pairs, as described in the sections below, that can be used to facilitate preparation and/or purification of the nanoreporter. In addition, certain nanoreporters of the invention are capable of forming complexes with molecules that comprise members of binding pairs, as described below. These complexes can be used to facilitate preparation and/or purification of the nanoreporter or complex.

5.13 Immobilization of Stretched Nanoreporters

A macromolecule can be selectively immobilized while fully extended under whatever force is used for the extension. In addition, the methods of the invention facilitate the selective immobilization of extended nanoreporters that are oriented with respect to each other. In other words, according to the methods of the invention, a plurality of nanoreporters can readily be immobilized in the same orientation with respect to each other.

In one aspect, the present invention provides methods for selectively immobilizing a nanoreporter in an extended state. The macromolecule can be any macromolecule known to those of skill in the art such as a polymer, a polysaccharide, a polynucleotide or a polypeptide. For the methods of this aspect of the invention, generally, a first portion of the nanoreporter is immobilized by any technique known to those of skill in the art. Indeed, the technique for immobilizing the first portion of the nanoreporter is not critical to many embodiments of the invention. In certain embodiments, the first portion of the nanoreporter can be immobilized selectively or non-selectively. In certain embodiments the first portion is immobilized by one or more covalent bonds. In certain embodiments, the first portion is immobilized by one or more non-covalent bonds.

With an immobilized first portion, the nanoreporter can be extended by any technique for extending a nanoreporter apparent to those of skill in the art. In certain embodiments, the technique for extending the nanoreporter is not critical for the methods of the invention. In certain embodiments, the technique for extending the nanoreporter appropriate for the class of nanoreporter according to the judgment of one of skill in the art. In certain embodiments, the nanoreporter is extended by application of a force capable of extending the nanoreporter. The force can be any force apparent to one of skill in the art for extending the nanoreporter. Exemplary forces include gravity, hydrodynamic force, electromagnetic force and combinations thereof. Specific techniques for extending the nanoreporter are described in the sections below.

The nanoreporter is in an extended state if it would be recognized as extended by one of skill in the art. In certain embodiments, the nanoreporter is in an extended state when it is in the field of a force capable of extending the nanoreporter. In certain embodiments, the nanoreporter is in an extended state when its average hydrodynamic radius is more than double the average hydrodynamic radius of the nanoreporter in its native state as recognized by those of skill in the art.

In this aspect of the invention, the methods generally comprise the step of selectively immobilizing a second portion of the nanoreporter while it is in an extended state. This can result in an immobilized nanoreporter that is extended between the first and the second portion. Remarkably, since the nanoreporter is selectively immobilized while extended, that extension can be preserved in the immobilized nanoreporter. Generally, the first portion and the second portion of the nanoreporter are not the same.

The selective immobilization can be according to any technique for selective immobilization of a portion of a nanoreporter apparent to those of skill in the art. The selective immobilization can be through, for example, the formation of one or more covalent bonds or one or more non-covalent bonds, or both. Particular examples of selective immobilization techniques are described in the sections below. In particular embodiments, one or more binding pairs are used to immobilize the second portion of the nanoreporter.

The second portion can be immobilized onto any substrate apparent to those of skill in the art. The substrate can be any substrate judged to be useful for immobilization known to those of skill in the art. In certain embodiments, the second portion can be immobilized to another molecule. Further useful substrates include surfaces, membranes, beads, porous materials, electrodes, arrays and any other substrate apparent to those of skill in the art.

In another aspect, the present invention provides compositions comprising a selectively immobilized, extended nanoreporter. The compositions generally comprise a substrate and an extended nanoreporter selectively immobilized onto the substrate. The substrate can be any substrate known to those of skill in the art. Exemplary substrates include those described in the sections below. At least two portions of the nanoreporter are immobilized onto the substrate, and the nanoreporter is in an extended state between the two portions. In certain embodiments, at least one portion of the nanoreporter is selectively immobilized onto the substrate. In certain embodiments, two or more portions of the nanoreporter are selectively immobilized onto the substrate. The nanoreporter can be extended and/or immobilized by any technique apparent to those of skill, including particularly the methods of the present invention.

In another aspect, the present invention provides methods for selectively immobilizing a nanoreporter in an oriented state. The nanoreporter can be any nanoreporter described above. In certain embodiments, the nanoreporter can be flexible, or in certain embodiments the nanoreporter can be rigid or semi-rigid. For the methods of this aspect of the invention, generally, a first portion of the nanoreporter is immobilized as described above. With an immobilized first portion, the nanoreporter can be oriented by any technique for extending a nanoreporter apparent to those of skill in the art. In certain embodiments, the technique for orienting the nanoreporter is not critical for the methods of the invention. In certain embodiments, the technique for orienting the nanoreporter appropriate for the class of nanoreporter according to the judgment of one of skill in the art. In certain embodiments, the nanoreporter is oriented by application of a force capable of orienting the nanoreporter. The force can be any force apparent to one of skill in the art for orienting the nanoreporter. Exemplary forces include gravity, hydrodynamic force, electromagnetic force and combinations thereof.

The nanoreporter is in an oriented state if it would be recognized as oriented by one of skill in the art. In certain embodiments, the nanoreporter is in an oriented state when it is in the field of a force capable of orienting the nanoreporter. In certain embodiments, the nanoreporter is in an oriented state when its termini are arranged in parallel, as recognized by those of skill in the art, with the field of a force capable of orienting the nanoreporter. In certain embodiments, a plurality of nanoreporters is in an oriented state when the termini of the nanoreporters are arranged in parallel, as recognized by those of skill in the art.

In this aspect of the invention, the methods generally comprise the step of selectively immobilizing a second portion of the nanoreporter while it is in an oriented state. This can result in an immobilized nanoreporter that is oriented between the first and the second portion. Remarkably, since the nanoreporter is selectively immobilized while extended, that orientation can be preserved in the immobilized nanoreporter. The selective immobilization can be according to the methods described above.

In another aspect, the present invention provides compositions comprising a selectively immobilized, oriented nanoreporter. The compositions generally comprise a substrate and an oriented nanoreporter selectively immobilized onto the substrate. The substrate can be any substrate known to those of skill in the art. Exemplary substrates include those described in the sections below. At least two portions of the nanoreporter are immobilized onto the substrate, and the nanoreporter is in an oriented state between the two portions. In certain embodiments, at least one portion of the nanoreporter is selectively immobilized onto the substrate. In certain embodiments, both portions of the nanoreporter are selectively immobilized onto the substrate. The nanoreporter can be oriented and/or immobilized by any technique apparent to those of skill, including particularly the methods of the present invention.

The methods and compositions of the present invention can be used for any purpose apparent to those of skill in the art. For instance, the immobilized and extended and/or oriented nanoreporter can be used as a label for a substrate on which the nanoreporter is immobilized. The primary sequence of the immobilized and extended and/or oriented nanoreporter can be identified by any technique apparent to those of skill in the art. Advantageously, immobilization of the extended and/or oriented nanoreporter can facilitate such techniques. In certain embodiments, the immobilized and extended and/or oriented nanoreporter can be used to guide the manufacture of nanopaths, for example to create nanowires or nanocircuits. Further uses for the immobilized and extended and/or oriented nanoreporters are described in the sections below.

5.13.1 Methods of Selective Immobilization

As described above, the present invention provides methods for the selective immobilization of a nanoreporter in an extended state. The nanoreporter, once selectively immobilized, can be used for any purpose apparent to those of skill in the art.

5.13.2 Immobilization of First Portion

In the methods of the invention, a first portion of the nanoreporter is immobilized. Generally, the first portion is immobilized if it would be recognized as immobilized by one of skill in the art. The first portion can be immobilized by any technique apparent to those of skill in the art. In certain embodiments, the technique for immobilization of the first portion of the nanoreporter is not critical for the methods of the invention.

The first portion of the nanoreporter can be at any location in the nanoreporter. In certain embodiments, the first portion is at a terminus of the nanoreporter. For the purposes of the invention, a portion of a nanoreporter can be "at a terminus" when it is less than five, four, three, two, one or zero monomers from a terminus of the nanoreporter. Of course, although many nanoreporters have two termini, the methods of the invention are applicable to nanoreporters that have more than two termini and to nanoreporters having one or zero termini, e.g., circular nanoreporters. In certain embodiments, the first portion is not at a terminus of the nanoreporter.

The nanoreporter can be immobilized onto any substrate apparent to those of skill in the art. The substrate can be any moiety to which the nanoreporter can be immobilized without limitation. In certain embodiments, the substrate is a surface, membrane, bead, porous material, electrode or array.

In certain embodiments, the first portion of the nanoreporter can be immobilized non-selectively. In further embodiments, the first portion of the nanoreporter can be immobilized selectively. In advantageous embodiments, after the first portion of the nanoreporter is immobilized, some portion of the nanoreporter should be free to move sufficiently so that the nanoreporter can be extended and/or oriented in the following steps of the method. In particular, in certain embodiments, when the first portion of the nanoreporter is immobilized non-selectively, it is important that the entire nanoreporter not be immobilized non-selectively to an extent that prevents extension of any portion of the nanoreporter.

The immobilization can be by any interaction with the substrate apparent to those of skill in the art. The immobilization can be via electrostatic or ionic interaction, via one or more covalent bonds, via one or more non-covalent bonds or combinations thereof. In certain embodiments, the immobilization can be via electrostatic interaction with an electrode. In further embodiments, the immobilization is via electrostatic interaction with a substrate other than the electrode.

In certain embodiments, the first portion of the nanoreporter comprises a first member of a binding pair. The first member of the binding pair can be covalently bound to the first portion of the nanoreporter, or they can be non-covalently bound. Useful covalent bonds and non-covalent bonds will be apparent to those of skill in the art. In useful embodiments, the substrate onto which the first portion of the nanoreporter is bound will comprise a second member of the binding pair. The substrate can be covalently bound to the second member, or they can be non-covalently bound. FIG. 12 illustrates a nanoreporter that comprises a moiety F1 that is capable of selectively binding a moiety of the substrate. Moiety F1 can be, for example, biotin, capable of binding, for example, a substrate coated with avidin.

In certain embodiments, the first portion of the nanoreporter can comprise a member of a binding pair that is capable of binding with a member of a binding pair on the substrate to form one or more non-covalent bonds. Exemplary useful substrates include those that comprise a binding moiety selected from the group consisting of ligands, antigens, carbohydrates, nucleic acids, receptors, lectins, and antibodies. The first portion of the nanoreporter would comprise a binding moiety capable of binding with the binding moiety of the substrate. Exemplary useful substrates comprising reactive moieties include, but are not limited to, surfaces comprising epoxy, aldehyde, gold, hydrazide, sulfhydryl, NHS-ester, amine, thiol, carboxylate, maleimide, hydroxymethyl phosphine, imidoester, isocyanate, hydroxyl, pentafluorophenyl-ester, psoralen, pyridyl disulfide or vinyl sulfone, or mixtures thereof. Such surfaces can be obtained from commercial sources or prepared according to standard techniques.

In advantageous embodiments, the first portion of the nanoreporter can be immobilized to the substrate via an avidin-biotin binding pair. In certain embodiments, the nanoreporter can comprise a biotin moiety in its first portion. For instance, a polynucleotide nanoreporter can comprise a biotinylated nucleotide residue. Similarly, a polypeptide nanoreporter can comprise a biotinylated amino acid residue. The substrate comprising avidin can be any substrate comprising avidin known to those of skill in the art. Useful substrates comprising avidin are commercially available including TB0200 (Accelr8), SAD6, SAD20, SAD100, SAD500, SAD2000 (Xantec), SuperAvidin (Array-It), streptavidin slide (catalog #MPC 000, Xenopore) and STREPTAVIDINnslide (catalog #439003, Greiner Bio-one).

In certain embodiments, the first portion of the nanoreporter can comprise a nucleotide sequence that is capable of selectively binding a nucleotide sequence on the substrate. In further embodiments, the first portion of the nanoreporter can comprise avidin, and the substrate can comprise biotin. Useful substrates comprising biotin that are commercially available include, but are not limited to, Optiarray-biotin (Accler8), BD6, BD20, BD100, BD500 and BD2000 (Xantec).

In further embodiments, the first portion of the nanoreporter is capable of forming a complex with one or more other molecules that, in turn, are capable of binding, covalently or non-covalently, a binding moiety of the substrate. For instance, a first portion of the nanoreporter can be capable of selectively binding another molecule that comprises, for instance, a biotin moiety that is capable of selectively binding, for instance, an avidin moiety of the substrate. FIG. 13A illustrates a nanoreporter that is capable of selectively binding a second molecule X that is capable of selectively binding a third molecule that comprises F1. F1 is capable of selectively binding a moiety on a substrate. FIG. 13B illustrates a nanoreporter that is capable of selectively binding a second molecule that comprises F1, and F1 is capable of selectively binding a moiety on a substrate.

In further embodiments, the first portion of the nanoreporter can comprise a member of a binding pair that is capable of reacting with a member of a binding pair on the substrate to form one or more covalent bonds. Useful substrates comprising reactive groups include those that comprise a reactive moiety selected from the group consisting of succinamides, amines, aldehydes, epoxies and thiols. Exemplary useful substrates comprising reactive moieties include, but are not limited to, surfaces comprising epoxy, aldehyde, gold, hydrazide, sulfhydryl, NHS-ester, amine, thiol, carboxylate, maleimide, hydroxymethyl phosphine, imidoester, isocyanate, hydroxyl, pentafluorophenyl-ester, psoralen, pyridyl disulfide or vinyl sulfone, or mixtures thereof. Such surfaces can be obtained from commercial sources or prepared according to standard techniques. The first portion of the nanoreporter would comprise a reactive moiety capable of reacting with the reactive moiety of the substrate. Exemplary useful substrates comprising reactive moieties include, but are not limited to, OptArray-DNA NHS group (Accler8), Nexterion Slide AL (Schott) and Nexterion Slide E (Schott).

In certain embodiments, the first portion of the nanoreporter can comprise a reactive moiety that is capable of being bound to the substrate by photoactivation. The substrate could comprise the photoreactive moiety, or the first portion of the nanoreporter could comprise the photoreactive moiety. Some examples of photoreactive moieties include aryl azides, such as N-((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

In further embodiments, the first portion of the nanoreporter can be immobilized to the substrate via other binding pairs apparent to those of skill in the art.

5.13.3 Extension of the Nanoreporter

In certain methods of the invention, the nanoreporter is in an extended state. Generally, any nanoreporter is in an extended state if it would be recognized as such by one of skill in the art.

In certain embodiments, the nanoreporter is in an extended state when it is in the field of a force capable of extending the nanoreporter under conditions suitable for extending the nanoreporter. Such forces and conditions should be apparent to those of skill in the art. For instance, many nanoreporter can be extended by hydrodynamic force or by gravity, and many charged nanoreporter can be extended by electromagnetic force. In certain embodiments, the force can be applied to the nanoreporter indirectly. For instance, the nanoreporter can comprise or can be linked, covalently or noncovalently, to a moiety capable of being moved by a force. In certain embodiments, the nanoreporter can be linked to a moiety capable of being moved by electromagnetic, hydrodynamic or optical force.

In certain embodiments, the force is an electromagnetic force. For instance, when the nanoreporter is charged, such as a polynucleotide, the nanoreporter can be extended in an electric or magnetic field. The field should be strong enough to extend the nanoreporter according to the judgment of one of skill in the art. Exemplary techniques for extending a nanoreporter in an electric or magnetic field are described in Matsuura et al., 2002, *J Biomol Struct Dyn.* 20(3):429-36; Ferree & Blanch, 2003, *Biophys J.* 85(4):2539-46; Stigter & Bustamante, 1998, *Biophys J.* 1998 75(3):1197-210; Matsuura et al., 2001, *Nucleic Acids Res.* 29(16); Ferree & Blanch, 2004, *Biophys J.* 87(1):468-75; the contents of which are hereby incorporated by reference in their entirety.

In certain embodiments, the force is a hydrodynamic force. For instance, many nanoreporters, including polysaccharides, polypeptides, and polynucleotides, can be extended in the field of a moving fluid. The hydrodynamic force should be strong enough to extend the nanoreporter according to the judgment of one of skill in the art. Exemplary techniques for extending a nanoreporter in hydrodynamic field are described in Bensimon et al., 1994, *Science* 265:2096-2098; Henegariu et al., 2001, *BioTechniques* 31: 246-250; Kraus et al., 1997, *Human Genetics* 99:374-380; Michalet et al., 1997, *Science*

277:1518-1523; Yokota et al., 1997, *Nucleic Acids Res.* 25(5): 1064-70; Otobe et al., 2001, *Nucleic Acids Research* 29:109; Zimmerman & Cox, 1994, *Nucleic Acids Res.* 22(3):492-7, and U.S. Pat. Nos. 6,548,255, 6,344,319, 6,303,296, 6,265, 153, 6,225,055, 6,054,327, 5,840,862, the contents of which are hereby incorporated by reference in their entirety.

In certain embodiments, the force is gravity. In advantageous embodiments, the force of gravity can be combined with, for example, hydrodynamic force to extend the nanoreporter. In certain embodiments, The force should be strong enough to extend the nanoreporter according to the judgment of one of skill in the art. Exemplary techniques for extending a nanoreporter with gravity are described in Michalet et al., 1997, *Science* 277:1518-1523; Yokota et al., 1997, *Nucleic Acids Res.* 25(5):1064-70; Kraus et al., 1997, *Human Genetics* 99:374-380, the contents of which are hereby incorporated by reference in their entirety.

In particular embodiments, the force is applied through a moving meniscus. Those of skill in the art will recognize that a moving meniscus can apply various forces to a nanoreporter including hydrodynamic force, surface tension and/or any other force recognized by those of skill in the art. The meniscus can be moved by any technique apparent to those of skill in the art including evaporation and gravity. Exemplary techniques for extending a nanoreporter with a moving meniscus are described in, for example, U.S. Pat. Nos. 6,548,255, 6,344,319, 6,303,296, 6,265,153, 6,225,055, 6,054,327, 5,840,862, the contents of which are hereby incorporated by reference in their entireties.

In particular embodiments, the nanoreporter can be extended by an optical trap or optical tweezers. For instance, the nanoreporter can comprise or can be linked, covalently or noncovalently, to a particle capable of being trapped or moved by an appropriate source of optical force. Useful techniques for moving particles with optical traps or optical tweezers are described in Ashkin et al., 1986, *Optics Letters* 11:288-290; Ashkin et al., 1987, *Science* 235:1517-1520; Ashkin et al., *Nature* 330:769-771; Perkins et al., 1994, *Science* 264:822-826; Simmons et al., 1996, *Biophysical Journal* 70:1813-1822; Block et al., 1990, *Nature* 348:348-352; and Grier, 2003, *Nature* 424: 810-816; the contents of which are hereby incorporated by reference in their entireties.

In certain embodiments, the nanoreporter can be extended by combinations of the above forces that are apparent to those of skill in the art. In the examples, below, certain nanoreporters are extended by a combination of an electric field and hydrodynamic force.

The nanoreporter is extended when it would be recognized as extended by one of skill in the art according to standard criteria for extension of a nanoreporter. In certain embodiments, the nanoreporter is extended when it loses most of its tertiary structural features as recognized by those of skill in the art. In certain embodiments, the nanoreporter is extended when it loses most of its secondary structural features as recognized by those of skill in the art. In certain embodiments, the nanoreporter is extended when its primary structural features are detectable in sequence when imaged according to standard techniques. Exemplary imaging techniques are described in the examples below.

In certain embodiments, an extended state of a nanoreporter can be recognized by comparing its hydrodynamic radius to its average hydrodynamic radius when free in dilute solution. For instance, in certain embodiments, a nanoreporter, or portion thereof, is extended when its hydrodynamic radius is more than about double its average hydrodynamic radius in dilute solution. More quantitatively, R represents the hydrodynamic radius of the nanoreporter, or portion thereof, and <R> represents the average hydrodynamic radius of the nanoreporter, or portion thereof, in dilute solution. The average <R> should be calculated such that R for the nanoreporter, or portion thereof, when unbound in dilute solution is less than 2<R>95% of the time. In certain embodiments, a nanoreporter, or portion thereof, is in an extended state when R is greater than 1.5<R>, greater than 1.6<R>, greater than 1.7<R>, greater than 1.8<R>, greater than 1.9<R>; greater than 2.0<R>, greater than 2.1 <R>, greater than 2.2<R>, greater than 2.3<R>, greater than 2.4<R>, greater than 2.5<R> or greater than 3.0<R>. In particular embodiments, a nanoreporter, or portion thereof, is in an extended state when R is greater than 2.0<R>.

5.13.4 Orientation of the Nanoreporter

In certain methods of the invention, the nanoreporter is in an oriented state. Generally, any nanoreporter is in an oriented state if it would be recognized as such by one of skill in the art.

In certain embodiments, the nanoreporter is in an oriented state when it is in the field of a force capable of orienting the nanoreporter under conditions suitable for orienting the nanoreporter. Such forces and conditions should be apparent to those of skill in the art.

In certain embodiments, the force is an electromagnetic force. For instance, when the nanoreporter is charged, such as a polynucleotide, the nanoreporter can be oriented in an electric or magnetic field. The field should be strong enough to orient the nanoreporter according to the judgment of one of skill in the art. Exemplary techniques for orienting a nanoreporter in an electric or magnetic field are described above.

In certain embodiments, the force is a hydrodynamic force. For instance, many nanoreporters, including polysaccharides, polypeptides, and polynucleotides, can be oriented in the field of a moving fluid. The hydrodynamic force should be strong enough to orient the nanoreporter according to the judgment of one of skill in the art. Exemplary techniques for orienting a nanoreporter in hydrodynamic field are described above.

In certain embodiments, the force is gravity. In advantageous embodiments, the force of gravity can be combined with, for example, hydrodynamic force or surface tension to orient the nanoreporter. In certain embodiments, The force should be strong enough to orient the nanoreporter according to the judgment of one of skill in the art. Exemplary techniques for orienting a nanoreporter with gravity are described above.

In certain embodiments, the force in an optical force. For instance, the macromolecule can comprise or can be linked, covalently or noncovalently, to a particle capable of being trapped or moved by an appropriate source of optical force as described above.

In certain embodiments, the nanoreporter can be oriented by combinations of the above forces that are apparent to those of skill in the art. In the examples, below, certain nanoreporters are oriented by a combination of an electric field and hydrodynamic force.

The nanoreporter is oriented when it would be recognized as oriented by one of skill in the art according to standard criteria for orientation of a nanoreporter. In certain embodiments, the nanoreporter is oriented when it is arranged in parallel, as recognized by those of skill in the art, with the field of a force capable of orienting the nanoreporter. In certain embodiments, the nanoreporter is oriented when it is one of a plurality of nanoreporter that are arranged in parallel, as recognized by those of skill in the art. For instance, a plurality of nanoreporters can be oriented when the vector from a first terminus to a second terminus of a nanoreporter is parallel, as recognized by those of skill in the art, to the vectors between corresponding termini of other nanoreporters in the plurality.

5.13.5 Selective Immobilization of Second Portion of Nanoreporter

As discussed above, in the methods of the invention, a second portion of the nanoreporter is selectively immobilized. The second portion of the nanoreporter can be any portion of the nanoreporter that is not identical to the first portion of the nanoreporter. In some embodiments, the second portion of the nanoreporter does not overlap any part of the first portion of the nanoreporter.

In certain embodiments, the present invention provides methods that comprise the single step of selectively immobilizing a second portion of a nanoreporter while the nanoreporter is in an extended or oriented state, and while a first portion of the nanoreporter is immobilized. Exemplary methods for immobilization of the first portion of the nanoreporter, and for extension or orientation of the nanoreporter are described in detail in the sections above.

In certain embodiments, the present invention provides methods that comprise the step of extending a nanoreporter, while a first portion of the nanoreporter is immobilized, and the step of selectively immobilizing a second portion of a nanoreporter while the nanoreporter is in an extended state. Exemplary methods for immobilization of the first portion of the nanoreporter, and for extension of the nanoreporter are described in detail in the sections above.

In certain embodiments, the present invention provides methods that comprise the step of immobilizing a first portion of a nanoreporter, the step of extending the nanoreporter while the first portion is immobilized and the step of selectively immobilizing a second portion of a nanoreporter while the nanoreporter is in an extended state. Exemplary methods for immobilization of the first portion of the nanoreporter, and for extension of the nanoreporter are described in detail above.

In certain embodiments, the present invention provides methods that comprise the step of orienting a nanoreporter, while a first portion of the nanoreporter is immobilized, and the step of selectively immobilizing a second portion of a nanoreporter while the nanoreporter is in an oriented state. Exemplary methods for immobilization of the first portion of the nanoreporter, and for orienting the nanoreporter are described in detail in the sections above.

In certain embodiments, the present invention provides methods that comprise the step of immobilizing a first portion of a nanoreporter, the step of orienting the nanoreporter while the first portion is immobilized and the step of selectively immobilizing a second portion of a nanoreporter while the nanoreporter is in an oriented state. Exemplary methods for immobilization of the first portion of the nanoreporter, and for orienting the nanoreporter are described in detail above.

The selective immobilization of the second portion of the nanoreporter can follow any technique for selective immobilization of a nanoreporter apparent to those of skill in the art. Significantly, in advantageous embodiments of the invention, the second portion of the nanoreporter is not immobilized non-selectively. Selective immobilization can allow the nanoreporter to be immobilized while in a fully extended state or nearly fully extended state. Selective immobilization can also allow the nanoreporter to be immobilized in an oriented manner. In other words, the first portion and second portion of the nanoreporter can be immobilized along the direction of the field or fields used to extend the nanoreporter, with the first portion preceding the second portion in the field. When a plurality of nanoreporters are immobilized, the can be uniformly oriented along the field.

The second portion of the nanoreporter can be at any location in the nanoreporter. In certain embodiments, the second portion is at a terminus of the nanoreporter. In certain embodiments, the second portion is not at a terminus of the nanoreporter. In certain embodiments, the first portion, described in the sections above, is at one terminus of the nanoreporter, and the second portion is at another terminus of the nanoreporter.

As discussed above, the second portion of the nanoreporter is immobilized selectively. The immobilization can be by any selective interaction with the substrate apparent to those of skill in the art. The immobilization can be via electrostatic or ionic interaction, via one or more covalent bonds, via one or more non-covalent bonds or combinations thereof. In certain embodiments, the immobilization can be via electrostatic interaction with an electrode. In further embodiments, the immobilization is via electrostatic interaction with a substrate other than the electrode.

If the first portion and the second portion of the nanoreporter are selectively immobilized to the same substrate, the techniques of selective immobilization should of course be compatible with the substrate. In particular embodiments, the techniques of immobilization are the same. For instance, on a substrate coated with avidin, both the first and second portion of the nanoreporter can be immobilized selectively via biotin-avidin interactions. However, as will be apparent to those of skill in the art, the same interaction need not be used at both the first and second portions for immobilization on the same substrate. For instance, the substrate can comprise multiple moieties capable of selective binding, or the first portion can be immobilized non-selectively, or other techniques apparent to those of skill in the art.

In certain embodiments, the second portion of the nanoreporter comprises a first member of a binding pair. The second member of the binding pair can be covalently bound to the second portion of the nanoreporter, or they can be non-covalently bound. Useful covalent bonds and non-covalent bonds will be apparent to those of skill in the art. In useful embodiments, the substrate onto which the second portion of the nanoreporter is bound will comprise a second member of the binding pair. The substrate can be covalently bound to the second member, or they can be non-covalently bound.

In certain embodiments, the second portion of the nanoreporter can comprise a member of a binding pair that is capable of binding with a member of a binding pair on the substrate to form one or more non-covalent bonds. Exemplary useful substrates include those that comprise a binding moiety selected from the group consisting of ligands, antigens, carbohydrates, nucleic acids, receptors, lectins, and antibodies such as those described in the sections above.

In advantageous embodiments, the second portion of the nanoreporter can be immobilized to the substrate via an avidin-biotin binding pair. In certain embodiments, the nanoreporter can comprise a biotin moiety in its first portion. For instance, a polynucleotide nanoreporter can comprise a biotinylated nucleotide residue. Similarly, a polypeptide nanoreporter can comprise a biotinylated amino acid residue. Useful substrates comprising avidin are described in the sections above.

In further embodiments, the second portion of the nanoreporter can comprise avidin, and the substrate can comprise biotin. Useful substrates comprising biotin are described in the sections above.

In further embodiments, the second portion of the nanoreporter can comprise a member of a binding pair that is capable of reacting with a member of a binding pair on the substrate to form one or more covalent bonds. Exemplary useful substrates comprising reactive groups are described in the sections above.

In certain embodiments, the second portion of the nanoreporter can comprise a reactive moiety that is capable of being bound to the substrate by photoactivation. The substrate could comprise the photoreactive moiety, or the second portion of the nanoreporter could comprise the photoreactive moiety. Some examples of photoreactive moieties include aryl azides, such as N-((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-bromodeoxyuridine.

In further embodiments, the second portion of the nanoreporter can be immobilized to the substrate via other binding pairs described in the sections above.

In further embodiments, the second portion of the nanoreporter is capable of forming a complex with one or more other molecules that, in turn, are capable of binding, covalently or non-covalently, a binding moiety of the substrate. For instance, the second portion of the nanoreporter can be capable of selectively binding another molecule that comprises, for instance, a biotin moiety that is capable of selectively binding, for instance, an avidin moiety of the substrate. FIG. 12B illustrates a method of selectively binding a second molecule that comprises F3 that is, in turn, capable of selectively binding a moiety on a substrate. The interaction between the second portion of the nanoreporter and the molecule that comprises F3 can be mediated, for example, by an antigen-antibody interaction.

FIGS. 14A and 14B illustrate the selective immobilization of a nanoreporter according to methods of the present invention. In FIG. 14A, a first portion of the nanoreporter comprises binding moiety F1 that is capable of selectively binding a moiety on the illustrated substrate S. Binding moiety F1 can be, for instance, biotin, and substrate S can be coated with, for instance, avidin. The nanoreporter of FIG. 14 is extended by a force as described in the sections above. In FIG. 14B, the force is an electrical potential. While extended, the nanoreporter is contacted with molecules comprising binding moiety F2 that is capable of selectively binding a moiety on the illustrated substrate S. Binding moiety F2 can be, for instance, biotin, and substrate S can be coated with, for instance, avidin. Significantly, up to three molecules comprising F2 are capable of selectively binding to a second portion of the nanoreporter to selectively immobilize it in its extended state. As illustrated, the molecules comprise a second binding moiety that selectively binds a repeated binding moiety of the nanoreporter. The binding moieties can be, for instance, complementary nucleic acid sequences, as illustrated in FIG. 14B. The resulting nanoreporter is selectively immobilized in an extended state and should remain extended even when the force is removed. The selectively immobilized, extended nanoreporter can be used for any purpose apparent to those of skill in the art.

5.13.6 Immobilization of Two Portions of an Extended or Oriented Nanoreporter In certain embodiments, the present invention provides methods for selective immobilization of a first portion and a second portion of a nanoreporter that is in an extended or oriented state. Significantly, according to these methods of the invention, the nanoreporter need not be immobilized prior to application of a force capable of extending or orienting the nanoreporter.

In these methods, the nanoreporter is extended or oriented, or both, by a force capable of extending or orienting the nanoreporter. Such forces are described in detail in the sections above. In particular embodiments, the force is a force capable of extending or orienting the nanoreporter while maintaining the nanoreporter in one location, i.e. a force capable of extending or orienting without substantially moving the nanoreporter. Exemplary forces include oscillating electromagnetic fields and oscillating hydrodynamic fields. In a particular embodiment, the force is an oscillating electrical field. Exemplary techniques for extending or orienting a nanoreporter in an oscillating electric field are described in Asbury et al., 2002, *Electrophoresis* 23(16):2658-66; Kabata et al., 1993, *Science* 262(5139):1561-3; and Asbury and van den Engh, 1998, *Biophys J.* 74:1024-30, the contents of which are hereby incorporated by reference in their entirety.

In the methods, the nanoreporter is immobilized at a first portion and at a second portion while extended or oriented. Both the first portion and the second portion can be immobilized non-selectively, both can be immobilized selectively, or one can be immobilized selectively and the other non-selectively. Techniques for immobilization of the first portion and second portion are described in detail in the sections above.

5.13.7 Substrate for Immobilization

In the methods of the invention, the substrate for immobilization can be any substrate capable of selectively binding the nanoreporter apparent to those of skill in the art. Further, in certain aspects, the present invention provides compositions comprising a selectively immobilized nanoreporter in an extended state. The compositions comprise a substrate, as described herein, having immobilized thereto a nanoreporter in an extended state. The nanoreporter can be, of course, immobilized according to a method of the invention.

The only requirement of the substrate is that it be capable of selectively binding the second portion of the nanoreporter as described above. Thus, the substrate can be a filter or a membrane, such as a nitrocellulose or nylon, glass, a polymer such as polyacrylamide, a gel such as agarose, dextran, cellulose, polystyrene, latex, or any other material known to those of skill in the art to which capture compounds can be immobilized. The substrate can be composed of a porous material such as acrylic, styrene methyl methacrylate copolymer and ethylene/acrylic acid.

The substrate can take on any form so long as the form does not prevent selective immobilization of the second portion of the nanoreporter. For instance, the substrate can have the form of a disk, slab, strip, bead, submicron particle, coated magnetic bead, gel pad, microtiter well, slide, membrane, fit or other form known to those of skill in the art. The substrate is optionally disposed within a housing, such as a chromatography column, spin column, syringe barrel, pipette, pipette tip, 96 or 384 well plate, microchannel, capillary, etc., that aids the flow of liquid over or through the substrate.

The nanoreporter can be immobilized on a single substrate or on a plurality of substrates. For instance, in certain embodiments, the first and second portions are immobilized on the same substrate, as recognized by those of skill in the art. In certain embodiments, the first portion of the nanoreporter can be immobilized on a first substrate while the second portion of the nanoreporter can be immobilized on a second substrate, distinct from the first.

The substrate can be prepared according to any method apparent to those of skill in the art. For a review of the myriad techniques that can be used to activate exemplary substrates of the invention with a sufficient density of reactive groups, see, the *Wiley Encyclopedia of Packaging Technology*, 2d Ed., Brody & Marsh, Ed., "Surface Treatment," pp. 867 874, John Wiley & Sons (1997), and the references cited therein. Chemical methods suitable for generating amino groups on silicon oxide substrates are described in Atkinson & Smith, "Solid Phase Synthesis of Oligodeoxyribonucleotides by the Phosphite Triester Method," In: *Oligonucleotide Synthesis: A Practical Approach*, M J Gait, Ed., 1984, IRL Press, Oxford, particularly at pp. 45 49 (and the references cited therein); chemical methods suitable for generating hydroxyl groups on silicon oxide substrates are described in Pease et al., 1994, *Proc. Natl. Acad. Sci. USA* 91:5022 5026 (and the references cited therein); chemical methods for generating functional groups on polymers such as polystyrene, polyamides and grafted polystyrenes are described in Lloyd Williams et al., 1997, Chemical Approaches to the Synthesis of Peptides and Proteins, Chapter 2, CRC Press, Boca Raton, Fla. (and the references cited therein).

Exemplary useful substrates include surfaces coated with streptavidin, e.g., Accelr8 TB0200. Further useful substrates include surfaces coated with N-hydroxysuccinamide that are capable of reacting with a portion of a nanoreporter that comprises an amine. One such surface is OptArray-DNA (Accelr8). Additional useful surfaces are coated with aldehyde (e.g., Nexterion Slide AL, Schott) and surfaces coated with epoxy (e.g., Nexterion Slide E, Schott). Another useful surface is a biotinylated BSA coated surface useful for selective immobilization of a portion of a nanoreporter that comprises avidin or streptavidin.

5.13.8 Methods of Using Selectively Immobilized Extended or Oriented Nanoreporters The selectively immobilized, extended and/or oriented nanoreporters can be used for any purpose apparent to those of skill in the art. For instance, the selectively immobilized, extended and/or oriented nanoreporters are useful for mapping, nanoassembly and surface plasmon resonance. In certain embodiments, the selectively immobilized, extended and/or oriented nanoreporters can be used for macromoleculars with a variety of techniques, e.g., atomic force microscopy or electron microscopy.

In certain embodiments, the selectively immobilized, extended and/or oriented nanoreporters can be used for macromolecular mapping. For instance, they can be used to determine the location of binding or hybridization along a macromolecule by, for example, fluorescent molecules or DNA binding proteins.

In certain embodiments, the selectively immobilized, extended and/or oriented nanoreporters can be used for nanoassembly. For instance, they can be used to facilitate crystal growth on extended and/or oriented nanoreporters, or crystal growth on polypeptides linked or bound to extended and/or oriented macromolecules. In certain embodiments, the selectively immobilized, extended and/or oriented macromolecules can be used for the construction of nanopaths. In certain embodiments, the selectively immobilized, extended and/or oriented nanoreporters can be used for directed transport using molecular motors, such as kinesin or myosin. In certain embodiments, the selectively immobilized, extended and/or oriented nanoreporters can be used for molecular computing or for the assembly of circuits comprising macromolecules, e.g., DNA computing. In certain embodiments, the selectively immobilized, extended and/or oriented nanoreporters can be used to manipulate carbon nanotubes.

In certain embodiments, the selectively immobilized, extended and/or oriented nanoreporters can be used for the study of polynucleotide binding proteins. They can be used, for instance, to determine the presence or location of protein bound to a polynucleotide. Useful techniques include surface plasmon resonance. In certain embodiments, the selectively immobilized, extended and/or oriented nanoreporters can be used for the study of protein fibers, such as amyloid, titin, and fibronectin.

In certain embodiments, the-selectively immobilized, extended and/or oriented nanoreporters can be used to create macromolecular barcodes for the purposes of separation and sequential detection of labels. These labels spaced along the molecule provide a unique code that can be read when the nanoreporter is immobilized and extended and/or oriented. Extension and/or orientation with selective immobilization can facilitate the decoding of the macromolecular barcode.

The selectively immobilized, extended and/or oriented nanoreporters can further be used for can be used in any context where detection or imaging of a nanoreporters might be useful. They can be used for diagnostic, prognostic therapeutic and screening purposes. For instance, they can be applied to the analysis of biomolecular samples obtained or derived from a patient so as to determine whether a diseased cell type is present in the sample and/or to stage the disease. They can be used to diagnose pathogen infections, for example infections by intracellular bacteria and viruses, by determining the presence and/or quantity of markers of bacterium or virus, respectively, in the sample. The compositions and methods of the invention can be used to quantify target molecules whose abundance is indicative of a biological state or disease condition, for example, blood markers that are upregulated or downregulated as a result of a disease state. In addition, the compositions and methods of the invention can be used to provide prognostic information that assists in determining a course of treatment for a patient.

5.13.9 Kits Comprising Selectively Immobilized, Extended or Oriented Nanoreporters The invention further provides kits comprising one or more components of the invention. The kits can comprise, for example, a substrate according to the invention and one or more extended and/or oriented, or both, nanoreporters selectively immobilized on the substrate. The kits can be used for any purpose apparent to those of skill in the art, including, those described above.

In certain embodiments, the present invention also provides kits useful for the extension and/or orientation and selective immobilization of nanoreporters. The kits can comprise a substrate for immobilization and one or more binding partners to facilitate extension and/or orientation or immobilization of a nanoreporter. The binding partners could, in certain embodiments, comprise a moiety useful for extension and/or orientation of the nanoreporter in an appropriate force. In certain embodiments, the binding partners could facilitate immobilization or selective immobilization of the nanoreporter to the surface. In further embodiments, the kit could comprise a nanoreporter for extension and/or orientation and immobilization. In further embodiments, the kit could comprise a device capable of extending the nanoreporter.

5.14 Detection of Nanoreporters

Nanoreporters are detected by any means available in the art that are capable of detecting the specific signals on a given nanoreporter. Where the nanoreporter is fluorescently labeled, suitable consideration of appropriate excitation sources may be investigated. Possible sources may include but are not limited to arc lamp, xenon lamp, lasers, light emitting diodes or some combination thereof. The appropriate excitation source is used in conjunction with an appropriate optical detection system, for example an inverted fluorescent microscope, an epi-fluorescent microscope or a confocal microscope. Preferably, a microscope is used that can allow for detection with enough spatial resolution to determine the sequence of the spots on the nanoreporter.

5.14.1 Microscope and Objective Lens Selection

The major consideration regarding the microscope objective lens is with the optical resolution, which is determined by its numerical aperture (NA). Generally, the larger the NA, the better the optical resolution. The required NA is preferably at least 1.07 based on the relationship of $\delta=0.61\lambda/NA$ ($\delta$=optical resolution and $\lambda$=wavelength). The amount of light that is collected by an objective is determined by $NA^4/Mag^2$ (Mag=magnification of the objective). Therefore, in order to collect as much light as possible, objectives with high NA and low magnifications should be selected.

5.14.2 CCD Camera Selection and Image Capture Techniques

When selecting a CCD camera, the first consideration is the pixel size, which partially determines the final resolution of the imaging system. Optimally the optical resolution should not be compromised by the CCD camera. For example, if the optical resolution is 210-300 nm, which corresponds to 12.6-18 μm on a CCD chip after a 60× magnification, in order to resolve and maintain the optical resolution there should be at least two pixels to sample each spot. Or the pixel size of the CCD chip should be at most 6.3-9 μm.

The second consideration is detection sensitivity which can be determined by many factors that include but are not limited to pixel size, quantum efficiency, readout noise and dark noise. To achieve high sensitivity, select a qualitative camera with big pixel size (which can give big collection area), high quantum efficiency and low noise. An exemplary camera with these criteria is the Orca-Ag camera from Hamamatsu Inc.

5.15 Computer Systems

The invention provides computer systems that may be used to automate nanoreporter image collection, perform nanoreporter identification and/or decode nanoreporter codes. Specifically, the invention provides various computer systems which run one or more programs described below (e.g., data storage module 44, label identification module 50, probe identification module 54). The computer systems can control a camera that takes light images of nanoreporters bound on substrates. These light images are then used by the computers of the present invention to identify and decode nanoreporters.

FIG. 9 details an exemplary system that supports the functionality described herein. The system is preferably a computer system 10 having:

- a central processing unit 22;
- a main non-volatile storage unit 14, for example, a hard disk drive, for storing software and data, the storage unit 14 controlled by controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 or other output device;
- a network interface card 20 or other communication circuitry for connecting to detector 72 and, optionally, any wired or wireless communication network 34 (e.g., the Internet or any other wide area network);
- an internal bus 30 for interconnecting the aforementioned elements of the system; and
- a power source 24 to power the aforementioned elements.

Operation of computer system 10 is controlled primarily by operating system 40, which is executed by central processing unit 22. Operating system 40 can be stored in system memory 36. In addition to operating system 40, in a typical implementation, system memory 36 can include one or more of the following:

- file system 42 for controlling access to the various files and data structures used by the present invention;
- a data storage module 44 comprising instructions for storing a plurality of light images 46;
- a label identification module 50 for identifying a plurality of labels 52 in the plurality of light images that are proximate to each other on a substrate, where a spatial order of the plurality of labels determines a string sequence of the plurality of labels;
- a probe identification module 54 for determining for determining whether the string sequence of a plurality of labels comprises a valid reporter sequence; and
- a lookup table 56 that includes a plurality of valid reporter sequences 58.

As illustrated in FIG. 9, computer system 10 comprises software program modules and data structures. The data structures stored in computer system 10 include, for example, images 46, labels 52, and lookup table 56. Each of these data structures can comprise any form of data storage including, but not limited to, a flat ASCII or binary file, an Excel spreadsheet, a relational database (SQL), an on-line analytical processing (OLAP) database (MDX and/or variants thereof), or a comma separated value file. In some embodiments, the data structures and software modules depicted in FIG. 9 are not housed on computer system 10, but rather are housed on a computer or other type of storage device that is in electrical communication with computer system 10 across network 34.

One aspect of the present invention provides a computer program product comprising a computer readable storage medium (e.g., memory 36, storage unit 14, and/or other computer readable storage media) and a computer program mechanism embedded therein. The computer program mechanism is for detecting the presence of a probe within a sample overlayed on a substrate. As described above, the probe comprises a plurality of spatially arranged label monomers in one or more label attachment regions of a given nanoreporter. The sequence of signals emitted by the label monomers associated with the various label attachment regions of the scaffold of a given nanoreporter allows for the unique identification of the nanoreporter. The computer program mechanism comprises data storage module 44, label identification module 50, and probe identification module 54.

Data storage module 44. Data storage module 44 comprises instructions for storing a plurality of light images 46. Each light image in the plurality of light images is from light emitted from a sample overlayed on a substrate. Representative biological samples are described in Section 5.10, above.

Representative substrates are described in Section 5.13.7. In typical embodiments, each light image in the plurality of light images is a scan, taken by detector 72, of a portion of a substrate. Exemplary detectors 72 are described in Section 5.14.2. A nonlimiting exemplary detector 72 is the Orca-Ag camera from Hamamatsu Inc. Each light image is a picture of the substrate onto which the sample containing a nanoreporter is overlayed that is taken by detector 72. Each light image records light from the sample at a corresponding wavelength range in a plurality of different wavelength ranges. In other words, each light image measures light in a select wavelength range. In some embodiments, the wavelength range of a light image is determined by the specifications of a light filter that filters light received by detector 72. The filter effectively blocks out light that is not within a specified wavelength range. In practice, a plurality of light images is taken, and each light image in the plurality of light images is taken using a filter selected from a plurality of different filters. In some embodiments, 2 or more light images, 3 or more light images, 4 or more light images, 5 or more light images, 6 or more light images, 7 or more light images, 8 or more light images, 9 or more light images, or 10 or more light images, between 2 and 20 light images, between 2 and 100 light images, or less than 30 light images are taken. Filters for limiting light to predetermined wavelength ranges are commercially available. Nonlimiting examples of commercially available filters are HQ480/40, Q505LP, HQ535/50, HQ545/30x, 570LP, HQ587/30m, HQ630/20, Q649LP, and HQ655LP by Chroma Inc. Exemplary wavelength ranges in the plurality of different wavelength ranges could be, for example, the wavelength range between 485 nm and 585 nm, the wavelength range between 557 nm and 617 nm, the wavelength range between 637 nm and 697 nm, the wavelength range between 510 nm and 650 nm, the wavelength range between 586 nm and 658 nm, the wavelength range between 515 nm and 575 nm, and the wavelength range between 440 nm and 520 nm. Many other wavelength ranges can be used in addition to or instead of some or all of the aforementioned wavelength ranges.

In some embodiments, the plurality of different wavelength ranges consists of between two and six different wavelength ranges, between two and twenty different wavelength ranges, more than ten different wavelength ranges, more than twenty different wavelength ranges, more than thirty different wavelength ranges, more than forty different wavelength ranges, more than 100 different wavelength ranges, or less than fifty different wavelength ranges. In some embodiments each wavelength range represents a different color. In some embodiments there is some degree of overlap between different wavelength ranges. In some embodiments there is no overlap between different wavelength ranges.

An advantage of the present invention is that there is no requirement that the nanoreporters of the present invention be overlayed at a predetermined position on the substrate as is the case in the microarray arts. While specialized substrates can be prepared such that the nanoreporters of the present invention will adhere to predetermined positions on a substrate, in preferred embodiments, the location where a nanostring adheres to a substrate is totally random. Furthermore, in preferred embodiments, all that needs to be determined is the identity of a nanoreporter on the substrate. Thus, signals are measured from the substrate for the purpose of nanoreporter identification. As such, signals are processed in a binary fashion (e.g., absence or presence of at a given wavelength) in preferred embodiments using the software modules described below. In some embodiments, not only is the position of nanoreporters on the substrate random, so is the orientation.

Even in instances where the orientation of the nanoreporter on the substrate is random, the software modules described below can identify the nanoreporters. Another advantage of the present invention is that there is no requirement that multiple regions of the substrate be stitched together into a composite light image. Multiple light images of the substrate are taken, but each of these light images is from the same region of the substrate, just at different wavelengths.

In some embodiments, a label will fluoresce at multiple wavelengths (e.g., red and blue). In such embodiments the label identification module described below detects such a label by measuring a spot in the same position on the substrate in multiple light images. Intensity criteria can be used in such instances. For example, a requirement could be imposed that (i) a minimum blue intensity be observed in a light image that stores blue light emitted by the sample and (ii) that a minimum red intensity be observed in the same spot in the light image that stores red light emitted by the sample.

Label identification module 50. Label identification module 50 comprises instructions for identifying a plurality of labels (label monomers), in the plurality of light images 46, that are proximate to each other on the substrate. In typical embodiments, each label in a nanoreporter will emit light that causes a corresponding bright spot to appear in one or more light images 46. Each light image 46 may have dozens, hundreds, or even thousands of spots, where each spot potentially represents a label in a nanoreporter. Label identification module 50 deems these spots in the light images to be labels when specific criteria, described in detail below, are satisfied.

Label identification module 50 is capable of identifying labels that are proximate to each other on the substrate even when these labels appear in different light images. For example, consider the case in which label 1 (light monomer 1) and label 2 (light monomer 2) are in the same nanoreporter and are spatially proximate on the substrate. Further consider that label 1 and label 2 emit light within different wavelength ranges. Thus, in this example, light emitted by label 1 and by label 2 are recorded in different light images, say light image A and light image B, respectively. In some embodiments, the light emission of label 1 is recorded as a bright intensity spot in light image A whereas the light emission of label 2 is recorded as a bright intensity spot in light image B. In this example, label identification module 50 superimposes light image A and light image B. Light image A and light image B both cover the same region of the substrate. This region of the substrate may encompass several nanoreporters. In fact, this the region of the substrate covered by light image A and light image B may encompass hundreds or even thousands of nanoreporters. Therefore, light image A and light image B can each potentially record dozens, hundreds, or even thousands of labels, where each such label appears, for example, as a bright spot within light image A, light image B, or some other light image that is taken by detector 72. Light image A and light image B only differ by the wavelength range recorded. Because light image A and light image B are spatially superimposed on each other, label identification module 50 can identify the spatial proximity of label 1 and label 2 even though label 1 and label 2 originate in different light images, based on the spatial proximity of label 1 and label 2 in the superimposed light images.

Each wavelength range represented by a light image 46 is intended to measure a particular color emitted by one or more label monomers in a nanostring. In some embodiments, a wavelength range encompasses a contiguous set of wavelengths having a spectral width of up to 10 nm, up to 20 nm, up to 30 nm, up to 40 nm, up to 50 nm, up to 60 nm, up to 70 nm, up to 80 nm, up to 90 nm, or up to 100 nm.

In some embodiments, label identification module 50 aligns the light images using fiducials. A nonlimiting example of a fiducial is a latex bead that is impregnated with many different types of dye. One example of a fiducial is the MultiSpeck™ Multispectral Fluorescence Microscopy Kit (Molecular Probes, Inc., Eugene, Oreg.). The MultiSpeck™ Multispectral Fluorescence Microscopy Standards Kit is marketed as an external reference for comparing images collected with different optics, on different instruments and in different laboratories, as well as for monitoring routine day-to-day variations in instrumental performance. The kit includes two suspensions of submicron-diameter microspheres. The first suspension, the MultiSpeck suspension, is comprised of multispectral fluorescent microspheres that exhibit three relatively distinct excitation and emission bands, red, green and blue, all in the same particle. When excited with ultraviolet light, each sphere emits blue fluorescence, whereas when fluorescein or rhodamine/Texas Red® excitation filters are used, the spheres fluoresce at wavelengths similar to fluorescein or rhodamine/Texas Red emissions, respectively. Furthermore, because a single multispectral microsphere will appear different colors depending on the filters used for observation, these microspheres can be used for image registration across multiple wavelengths, thus allowing for the accurate determination of the spatial relationships of multiple labels in a multiparameter experiment. The second suspension, the RGB Mix suspension, is comprised of a mixture of "single-band" microspheres that exhibit the same three excitation/emission bands, red, green and blue, (RGB) as the multispectral microspheres, but in separate particles. Thus, a fiducial will emit light across several different wavelengths. Fiducials are randomly arranged on the substrate along with the sample. Because the fiducials emit light across a wide range of spectral frequencies, they are present in several if not all of the plurality of light images. Thus, label identification module 50 can align most if not all of the light images in a plurality of images to each other using the fiducial spots present in the light images provided that the light images are of the same region of the substrate (e.g., the same field of view).

A spatial order of the plurality of labels determines a string sequence of the plurality of labels. For example, consider the case in which the following string of label monomers are detected on the substrate: red-red-green-blue. The spatial order of these label monomers on the substrate dictates the string sequence of a possible probe. Thus, if serially arranged label monomers are detected on the substrate with the serial arrangement: red-red-green-blue, the serially arranged label monomers form the string sequence: RRGB, where R stands for red, G stands for green, and B stands for blue. The string sequence RRGB is potentially a string sequence of a valid probe.

The present invention encompasses a broad range of different labels that may be used in a probe. In some embodiments, each label in a plurality of spatially arranged labels can emit light in one of four different wavelength ranges: a red wavelength range, a green wavelength range, a blue wavelength range, or blank (no emission). In some embodiments, each label in a plurality of spatially arranged labels can emit light in one of five different wavelength ranges, six different wavelength ranges, seven different wavelength ranges, eight different wavelength ranges, nine different wavelength ranges, ten different wavelength ranges, between five and fifteen different wavelength ranges, between four and twenty different wavelength ranges, between three and forty different wavelength ranges, more than 30 different wavelength ranges, or less than 100 different wavelength ranges. Furthermore, the present invention imposes no limitation on the number of labels (label monomers) that are present in a given probe. In some embodiments, there are between two and 100 labels in a probe, between two and 1000 labels in a probe, between two and 20 labels in a probe, between three and 40 labels in a probe, more than five labels in a probe, more than six labels in a probe, more than seven labels in a probe, more than ten labels in a probe, or less than fifty labels in a probe.

Label identification module 50 determines the spatial order of the labels on a substrate. To accomplish this, a plurality of labels in the images is identified. In typical embodiments, there is more than one probe on the portion of the substrate that is imaged, and each such probe has a plurality of spatially arranged labels that generate corresponding spots in the light images. In some embodiments, there are between two and 10,000 probes in the portion of the substrate being imaged. Thus, label identification module 50 has to determine which spots in images are labels as well as identify sets of labels that each belong to a single probe. This task is made more complex in preferred embodiments where probes randomly bind to the substrate.

In some embodiments, label identification module 50 first validates labels in light images. Then, label identification module 50 proceeds to determine which of the labels in the plurality of labels belong to the same probe using one or more rules. In some embodiments label identification module 50 first identifies a plurality of candidate labels giving rise to spots in the plurality of light images. Each candidate label in the plurality of candidate labels comprises a position on the substrate that emits more than a threshold amount of light in one or more light images in the plurality of light images. In some embodiments, the plurality of labels comprises a first candidate label that emits light in a first wavelength in the plurality of different wavelengths and a second candidate label in the plurality of labels that emits light in a second wavelength in the plurality of different wavelengths. In some embodiments, a candidate label is deemed to be a valid label when it emits more than a threshold amount of light in any one light image in the plurality of light images. In some embodiments label identification module 50 verifies that a candidate label is a valid label when the label satisfies a spot shape criterion (e.g., a match between an observed spot shape of the candidate label and the theoretical point spread of the diffraction limited point source light determined by a magnification of the candidate label). In some embodiments, label identification module 50 verifies that a candidate label is a valid label using point spread function modeling. In some embodiments, label identification module 50 validates a candidate label using a spot segmentation algorithm (e.g., a watershed transformation). Watershed transformations are described in Vincent and Soille, 1991, *IEEE Transactions on Pattern Analysis and Machine Intelligence* 13, pp. 583-598, which is hereby incorporated by reference herein, in its entirety.

In some embodiments, label identification module 50 verifies that a candidate label is a valid label when the label satisfies a spot shape criterion (e.g., a match between an observed spot shape of the label and the theoretical point spread of the diffraction limited point source light determined by a magnification of the label in an image in which the label was observed). In some embodiments, the spot shape criterion is evaluated using point spread function modeling. In some embodiments, the spot shape criterion is evaluated using a spot segmentation algorithm (e.g., a watershed transformation). An exemplary application of a watershed transformation is described in Park et al., 2004, "Automatic Microarray Image Segmentation Based on Watershed Transformation," Proceedings of the $17^{th}$ International Conference on Pattern Recognition, volume 3, pages 786-789, which is hereby incorporated by reference herein in its entirety.

In some embodiments, an image segmentation step is performed by label identification module 50 on a candidate label in a light image in the plurality of light images to determine which pixels form the spot in the light image generated by the label, which pixels form the background, and which pixels are just noise or artifacts and should be eliminated. In some embodiments, a pure spatial-based signal segmentation approach is used by label identification module 50, in which a circle is placed over the spot generated by the label. In this approach, all pixels within this circle are counted as part of the spot and all pixels outside the circle are used to calculate background. The pixels between the two circles correspond to the transition area between the spot and its background and are discarded in order to improve the quality of the data. In this approach, all the pixels outside the circle within the boundary of a predetermined square are considered as background.

In some embodiments, intensity based segmentation is used by label identification module 50 to validate candidate labels. Methods in this category use exclusively intensity information to segment out signal pixels from background. Such approaches assume that the signal pixels are brighter on average than the background pixels. As an example, suppose that the target region around the spot taken from the light image consists of 40×40 pixels. The spot is about twenty pixels in diameter. Thus, from the total of 1600 (40×40) pixels in the region, about 314 ($\pi \times 10^2$, since the area of a circle is $\pi r^2$, where r stand for radius and is half the diameter) pixels, or 20%, are signal pixels and they are expected to have their intensity values higher than that of the background pixels. To identify these signal pixels, all the pixels from the target region are ordered in a one dimensional array from the lowest intensity pixel to the highest one $\{p_1, p_2, p_3, \ldots, p_{2500}\}$, in which $p_i$ is the intensity value of the pixel of the $i^{th}$ lowest intensity among all the pixels. If there is no contamination in the target region, the top 20% pixels in the intensity rank may be classified as the signal pixels. In some embodiments, a spot is only considered valid if the intensity measured by the intensity based segmentation approach exceeds a threshold value. However, in the present invention, spot size is typically substantially less than twenty pixels in diameter but the described method is still applicable.

In some embodiments, Mann-Whitney segmentation is used by label identification module 50 in order to validate candidate labels. Mann-Whitney segmentation is described in Draghici, 2003, *Data Analysis Tools for DNA Microarrays*, Chapman & Hall/CRC, New York, p. 47, which is hereby incorporated by reference herein in its entirety. The Mann-Whitney segmentation approach combines the use of spatial information with some intensity based analysis. Based on the result of the spot finding operation performed by label identification module 50, a circle is placed in the target region to include the region in which the spot is expected to be found. Since the pixels outside of the circle are assumed to be the background, the statistical properties of these background pixels can be used to determine which pixels inside the circles are signal pixels. A Mann-Whitney test is used to obtain a threshold intensity level that will separate the signal pixels from other pixels (e.g., background) even if they are inside the expected area of the spot. The Mann-Whitney test is described in Smith, 1991, *Statistical Reasoning*, Third Edition, Allyn and Bacon, Boston, pp. 724-730, which is hereby incorporated by reference herein in its entirety. Pixels inside of the circle having a higher intensity than the threshold intensity are treated as signal. In some embodiments, a spot is only considered valid if the intensity measured by the Mann-Whitney segmentation approach exceeds a threshold value.

In some embodiments, a combined intensity-spatial segmentation (trimmed measurements approach) is used by label identification module 50 in order to validate candidate labels. This approach combines both spatial and intensity information in segmenting the signal pixels from the background in a manner similar to the Mann-Whitney approach. In this approach, the assumption is that once the spot for a label is localized by label identification module 50 and a target circle placed in the target region, most of the pixels inside of the circle will be signal pixels and most of the pixels outside of the circle will be background. However, due to spot shape irregularity, some signal pixels may leak out of the circle and some background pixels may get into the circle. Background pixels within the circle may be considered as outliers in the intensity distribution of the signal pixels. Similarly, signal pixels that fall outside the circle will also appear as outliers with respect to the intensity distribution of the background pixels. Contamination pixels anywhere will appear as outliers in the intensity domain for both signal and background. These outliers would severely change the measurement of the mean and total signal intensity if they are not eliminated. To remove the effect of outliers on these measurements, some embodiments of label identification module 50 can simply "trim-off" a fixed percentage of pixels from the intensity distribution of the pixels for both signal and background regions. The Mann-Whitney approach performs a statistical analysis on the pixels outside the presumed spot area and then uses the threshold calculated there to segment the pixels inside the target area. The trimmed measurements approach performs a statistical analysis of both distributions (outside as well as inside the presumed spot) and eliminates the outliers from each such distribution independently without making the leap of faith that the characteristics of the distribution outside will also reflect the properties of the distribution inside. Eliminating approximately 5-10% of each distribution allows this approach to cope with artifacts such as dust particles and other impurities. In preferred embodiments, label identification module 50 does not have to quantify the intensity of the spots corresponding to labels in the images. However, in some embodiments, label intensity is quantified using any quantification technique known in the art including, but not limited to, total signal intensity, mean signal intensity, and median signal intensity. Exemplary quantification techniques are described in Draghici, 2003, *Data Analysis Tools for DNA Microarrays*, Chapman & Hall/CRC, New York, Section 3.4.3, which is hereby incorporated by reference herein in its entirety.

The above-identified techniques identifies a plurality of candidate labels and validates all or some of these candidate labels. These are referred to as spot level rules. In some embodiments, to be valid, the spot for a label needs to match the theoretical point spread function of the diffraction limited point source light. Spots can be identified, for example, by a watershed transformation. In some embodiments, spots that exceed the diffraction limit are recorded. Next, because there can be more than one probe in the light images, label identification module 50 applies a priori knowledge about probe architecture to determine which validated labels belong to the same probe. In essence, this a priori knowledge is used to form a model of what a probe should look like in the light images. This model can then be reduced to a set of reporter level rules that can be used to verify that a given set of labels belongs to a given probe. Examples of such rules include applying a distance criterion between the centroid of one spot to another and requiring that spots considered to belong to the same probe do not form angles greater than a threshold amount. In essence, the expected model is fitted to observed validated labels. In some embodiments, a set of labels that gives the least amount of error when fitted to an expected model for a probe is deemed to belong to the same probe.

In some embodiments a priori knowledge used to formulate a model is the expectation that the labels belonging to the same probe will be linearly arranged. In some embodiments, a set of labels is subjected to linear regression in order to determine if the set of labels is linearly arranged. If the linear regression is satisfied, other rules may be applied to further validate that the set of labels belongs to the same probe. In some embodiments, a set of labels is considered linear if they fit a linear regression model criterion. In some embodiments, the set of labels is considered to fit a linear regression model criterion when an R-value for the regression model is 0.9 or greater. In some embodiments, as described herein, experimental conditions are imposed (e.g., an electric field) to guarantee that the probes are linearly arranged. In some embodiments, probes are not linearly arranged and more complex models that incorporate expected probe curvature are invoked. In some embodiments, the linear direction of probes on the substrate is not known (e.g., is not predetermined). In some embodiments, the linear direction of probes on the substrates is known (e.g., is predetermined). In each such embodiment, this a priori knowledge is used to form the model. In addition to rules concerning the shape of the probe (e.g., linear, curved, linear in a predetermined orientation), there are rules for label spacing. A spacing rule imposes constraints on the distance between labels in the set of labels. Additional types of rules concern the shape of spots that constitute the reporter. Spot shape has been discussed above in conjunction with algorithms that are designed to localize spots and measure spot intensity (e.g., a match between an observed spot shape and the theoretical point spread of the diffraction limited point source light determined by a magnification of the label, point spread function modeling, a spot segmentation algorithm such as a watershed transformation).

In some embodiments the model used to identify labels belonging to the same probe requires that the spacing between each label in a probe be equal or within a defined range. In one example, the model comprises the rules that (i) the labels for the probe are linearly arranged and (ii) the labels are spaced between 450 nm and 550 nm apart from each other. In some embodiments the model used to identify labels belonging to the same probe imposes no requirement that the labels be equally spaced. In fact, in some embodiments, information about a probe identity is encoded in the form of unequal spacing between probe spots. Further, in some embodiments, the string sequence encoded by a probe includes spacer label monomers that do not emit light in any of the wavelengths measured in the plurality of light images. The present invention imposes no constraints on the spacing between label monomers. However, once the nanoreporters are synthesized, the a priori knowledge about the nanoreporters can be used to construct the model. Accordingly, in some embodiments, a model imposes the constraint that labels belonging to the same probe are spaced between 100 nm and 150 nm of each other, between 150 nm and 200 nm of each other, between 200 nm and 250 nm of each other, between 250 nm and 300 nm of each other, between 350 nm and 400 nm of each other, between 400 nm and 450 nm of each other, between 450 nm and 500 nm of each other, between 500 nm and 550 nm of each other, or between 550 nm and 600 nm of each other. In some embodiments, the spacing between label monomers is unequal but is known. For example, in one four-label nanostring, the spacing between the first label and the second label is 400 nm, the spacing between the second label and the third label is 750 nm, and the spacing between the third label and the fourth label is 625 nm. This spacing information would be taken into account in constructing a model for this class of nanostring.

In models in which labels are equally spaced, the model is fit to observed labels and the model is satisfied if the observed labels fall within predetermined tolerances. In some embodiments, the models used to identify labels belonging to the same probe include angle rules. For example, consider the case of a four label nanostring. In some embodiments, a model for this nanostring will impose a largest tolerable angle constraint, such that no three labels in the nanostring form an angle larger than the largest tolerable angle constraint.

In some embodiments, a label identification module applies a first distance criterion between a centroid of a first label and a centroid of a second label in a plurality of labels. In some embodiments, the first distance criterion is determined by a calculated distance between a first label and a second label in the probe. In some embodiments, the label identification module applies a second distance criterion between a centroid of the second label and a centroid of a third label in the plurality of labels. The second distance criterion can be determined by, for example, a calculated distance between a second label and a third label in the probe. In some embodiments, the first distance criterion is the same as the second distance criterion. In some embodiments, the first distance criterion is different from the second distance criterion. In some embodiments, a value of the first distance criterion and a value of the second distance criterion contribute to determining whether the plurality of labels is the probe.

In some embodiments, the instructions for identifying the plurality of labels comprises instructions for identifying a buffer zone around a portion of the substrate that has select labels. A buffer zone is a region of the substrate that contains no labels. A buffer zone surrounds a portion of the substrate that has a set of labels. Identification of a buffer zone around a set of labels ensures that the set of labels surrounded by the buffer zone is in fact a set of labels that potentially corresponds to a probe. If a buffer zone around a given set of labels cannot be identified, the given set of labels could potentially be from two or more probes that are proximate to each other on the substrate. This is not a desirable result because it does not lead to proper probe identification. Therefore, the use of a buffer zone criterion can help to ensure that a given set of labels belongs to a single probe. In fact, in some embodiments, a set of labels identified on the substrate are not considered to be validated labels unless there is a buffer zone around the set of labels. Thus, in some embodiments, a set of labels may still be considered "candidate" labels unless and until the buffer zone criterion is satisfied. In some embodiments, the buffer zone is elongated in shape so that it will fit around a linear array of spots that represent a possible probe.

Probe identification module 54. Once label identification module 50 identifies a candidate probe on the substrate, probe identification module 54 determines whether the string sequence defined by the labels of the identified candidate probe constitutes a valid reporter sequence. When the string sequence of the plurality of labels is confirmed as a valid reporter sequence, the plurality of labels is deemed to be the probe. When the string sequence of the plurality of labels is not confirmed as a valid reporter sequence, the plurality of labels is deemed to not be the probe. In such embodiments, probe identification module 54 compares the string sequence of the plurality of labels to valid reporter sequences in a lookup table. In preferred embodiments, the lookup table includes a list of all possible valid string sequences. The premise behind the lookup table is that only some of the possible set of string sequences are actually used. For example, consider the case where nanostrings (probes) are constructed with four label monomers and each label monomer can adopt one of four different colors (e.g., red, green, blue, and blank). In this case, there are $4^4=64$ possible string sequences. Say that only twenty of these string sequences are actually used in the sample exposed to the substrate. In such embodiments, the lookup table would be populated with these twenty string sequences. If label identification module 50 identifies a probe on the substrate that has a string sequence that matches one of these twenty string sequences, the probe would be validated. If label identification module 50 identifies a probe on the substrate that has a string sequence that does not match one of these twenty string sequences, the probe would be discarded as an artifact. In many embodiments, the number of string sequences in the lookup table is a small fraction of the possible number of string sequences. This condition helps to ensure that only valid probes are identified on the substrate. In some embodiments, the probe has seven labels, each label adopting one of four different colors for a total of $7^4$ different string sequence, a small fraction of which are used to construct actual nanoreporters. In some embodiments, a probe has twenty labels, each label adopting one of twenty different colors for a total of $20^{20}$ different valid reporter sequences, a small fraction of which are used to construct actual nanoreporters. These exemplary embodiments merely serve to illustrate the dimensions of some embodiments of the present invention. As indicated above, a larger range of labels can be used in a given nanoreporter and each such label can adopt many different colors. In some embodiments, there are 2, 3, 4, 5, 6, 7, 8, 9, 10, 11, 12, 13, 14, 15, 16, 17, 18, 19, 20 or more labels in a probe and each label can adopt any one of 2, 3, 4, 5, 6, 7, 8, 9, 10, 11, 12, 13, 14, 15, 16, 17, 18, 19, 20 or more different colors. In some embodiments, there are 2, 3, 4, 5, 6, 7, 8, 9, 10, 11, 12, 13, 14, 15, 16, 17, 18, 19, 20 or more labels in a probe and each label can adopt any two of 2, 3, 4, 5, 6, 7, 8, 9, 10, 11, 12, 13, 14, 15, 16, 17, 18, 19, 20 or more different colors. In some embodiments, there are 2, 3, 4, 5, 6, 7, 8, 9, 10, 11, 12, 13, 14, 15, 16, 17, 18, 19, 20 or more labels in a probe and each label can adopt any three of 3, 4, 5, 6, 7, 8, 9, 10, 11, 12, 13, 14, 15, 16, 17, 18, 19, 20 or more different colors. In some embodiments, there are 2, 3, 4, 5, 6, 7, 8, 9, 10, 11, 12, 13, 14, 15, 16, 17, 18, 19, 20 or more labels in a probe and each label can adopt multiple colors (e.g., 2 colors, 3 colors, 4 colors) in a plurality of colors. In some embodiments, this plurality of colors consists of five or more colors, six or more colors, seven or more colors, between seven and one hundred colors, or more than twenty colors. In some embodiments, a color is a discrete wavelength range (e.g., 340 nm to 350 nm, 355 nm to 365 nm, etc.).

In some embodiments, a first subset of the labels in the string sequence defined by a probe serves to error check the identities of the labels in a second subset of the labels in the string sequence. For example, consider the case in which there are eight labels in a probe. The last two labels may serve to error check the identity of the first six labels. For instance, the last two labels in the string sequence may serve as a checksum for the first six labels in the string sequence. In some embodiments, the checksum values can actually be used to error correct a string sequence that has been misread by label identification module 50. Thus, in some embodiments, it is possible to validate a string sequence that is not present in the look-up table by applying error correction techniques to the string sequence using the checksum or other form of error correcting code present in the string sequence.

In some embodiments, where distance information encodes string identity in part, the lookup table comprises valid reporter sequences, where each such valid reporter sequence comprises distance information between labels in addition to a string sequence. In such embodiments, there must be a match between both the distance information and the string sequence in order to identify a valid probe. For example, consider the case in which the string sequence identified by label identification module 50 consist of three labels, where the distance between the first and second labels is $d_1$ and the distance between the second and third labels is $d_2$. In this example, probe identification module must find a string sequence in the lookup table 56 that encodes the same string sequence and has matching $d_1$ and $d_2$ distances between the first and second labels and the second and third labels, respectively.

In some embodiments, label identification module 50 comprises instructions for repeating the instructions for identifying a plurality of labels a plurality of times. Each time the instructions for identifying a plurality of labels is repeated, a different plurality of labels is identified, in the plurality of light images 46, that are proximate to each other on the substrate. In such embodiments, probe identification module 54 determines whether each such different plurality of labels identified by label identification module 50 comprises a valid reporter sequence. For each such different plurality of labels, probe identification module 54 deems the different plurality of labels to be a probe when the string sequence of the different plurality of labels is confirmed as a valid reporter sequence. Further, probe identification module 54 deems the different plurality of labels to not be a probe when the string sequence of the different plurality of labels is not confirmed as a valid reporter sequence. In some embodiments, a plurality of probes is identified. In some embodiments, the plurality of probes consists of three or more probes. two or more probes, three or more probes, ten or more probes, at least 5, 10, 15, 20, 50, 75, 100, 150, 200, 300, or 400 probes or more. In some embodiments, probe identification module 54 stores each type of probe identified. A probe "type" is identified by the string sequence of the probe. In some embodiments, probe identification model 54 stores each string sequence of each different plurality of labels that is not confirmed as a valid reporter sequence. In some embodiments, probe identification model 54 stores each string sequence of each different plurality of labels that is confirmed as a valid reporter sequence.

5.16 Applications of Nanoreporter Technology

The compositions and methods of the invention can be used for diagnostic, prognostic therapeutic and screening purposes. The present invention provides the advantage that many different target molecules can be analyzed at one time from a single biomolecular sample using the methods of the invention. This allows, for example, for several diagnostic tests to be performed on one sample.

5.16.1 Diagnostic/Prognostic Methods

The present methods can be applied to the analysis of biomolecular samples obtained or derived from a patient so as to determine whether a diseased cell type is present in the sample and/or to stage the disease. For example, a blood sample can be assayed according to any of the methods described herein to determine the presence and/or quantity of markers of a cancerous cell type in the sample, thereby diagnosing or staging the cancer. Alternatively, the methods described herein can be used to diagnose pathogen infections, for example infections by intracellular bacteria and viruses, by determining the presence and/or quantity of markers of bacterium or virus, respectively, in the sample. Thus, the target molecules detected using the compositions and methods of the invention can be either patient markers (such as a cancer marker) or markers of infection with a foreign agent, such as bacterial or viral markers. Because of the quantitative nature of nanoreporters, the compositions and methods of the invention can be used to quantitate target molecules whose abundance is indicative of a biological state or disease condition, for example, blood markers that are upregulated or downregulated as a result of a disease state.

In addition, the compositions and methods of the invention can be used to provide prognostic information that assists in determining a course of treatment for a patient. For example, the amount of a particular marker for a tumor can be accurately quantified from even a small sample from a patient. For certain diseases like breast cancer, overexpression of certain genes, such as Her2-neu, indicate a more aggressive course of treatment will be needed.

5.16.2 Screening Methods

The methods of the present invention can be used, inter alia, for determining the effect of a perturbation, including chemical compounds, mutations, temperature changes, growth hormones, growth factors, disease, or a change in culture conditions, on various target molecules, thereby identifying target molecules whose presence, absence or levels are indicative of a particular biological states. In a preferred embodiment, the present invention is used to elucidate and discover components and pathways of disease states. For example, the comparison of quantities of target molecules present in a disease tissue with "normal" tissue allows the elucidation of important target molecules involved in the disease, thereby identifying targets for the discovery/screening of new drug candidates that can be used to treat disease.

5.17 Methods for Identifying Probes

One aspect of the invention provides methods for detecting the presence of a probe within a sample overlayed on a substrate. In this aspect of the invention, the probe comprises a plurality of spatially arranged labels. In one such method, a plurality of labels, in a plurality of light images, that are proximate to each other on the substrate is identified. The spatial order of the plurality of labels determines a string sequence of the plurality of labels. Each light image in the plurality of light images is for light received from the sample at a wavelength range in a plurality of different wavelength ranges. In the method, a determination is made as to whether the string sequence of the plurality of labels comprises a valid reporter sequence. When the string sequence of the plurality of labels is confirmed as a valid reporter sequence, the plurality of labels is deemed to be the probe. When the string sequence of the plurality of labels is not confirmed as a valid reporter sequence, the plurality of labels is deemed to not be the probe.

In some embodiments, the determining step comprises comparing the string sequence of the plurality of labels to valid reporter sequences in a lookup table. In some embodiments, the method further comprises storing the string sequence of the plurality of labels that is not confirmed as a valid reporter sequence. For instance, the string sequence can be stored in an electronic memory. In some embodiments, the method further comprises aligning a first light image to a second light image in the plurality of light images using a plurality of fiducials present on the substrate.

In some embodiments, the step of identifying a plurality of labels is repeated a plurality of times. Each time the step of identifying a plurality of labels is repeated, a different plurality of labels is identified, in the plurality of light images, that are proximate to each other on the substrate. In some embodiments, the method further comprises determining whether each of the different plurality of labels comprises a valid reporter sequence. Each different plurality of labels is deemed to be a probe when the string sequence of the different plurality of labels is confirmed as a valid reporter sequence. Furthermore, each different plurality of labels is deemed to not be a probe when the string sequence of the different plurality of labels is not confirmed as a valid reporter sequence. In some instances according to this embodiment of the present invention, a plurality of probes is identified. For instance, in some embodiments, two or more probes, three or more probes, ten or more probes, at least 5, 10, 15, 20, 50, 75, 100, 150, 200, 300, or 400 probes or more are identified.

In some embodiments where a plurality of probes are identified, each type of probe identified is recorded. A probe "type" is identified by the string sequence of the probe. Each unique valid string sequence represents a different probe type. In some embodiments, each string sequence of each different plurality of labels that is not confirmed as a valid reporter sequence is stored. In this way, it is possible to determine common errors that arising in the probes on the substrate. One type of error that can be identified by tracking pluralities of labels that do not form valid string sequences is the condition where there are too many probes on the substrate. When there are too many probes on the substrate, the labels of neighboring probes become proximate to each other, making it difficult to determine which probe each label belongs to. Another type of error that can be identified is the condition in which an excessive number of probes get ripped apart, leaving truncated probes on the substrate. In some embodiments, all species of labels, strings, invalid reporter sequences, valid reporter sequences, probe types is tracked in the methods of the present invention.

6. EXAMPLES

The following examples are offered to illustrate this invention and are not to be construed in any way as limiting the scope of this invention.

6.1 Example 1

Selective Immobilization or Extended DNA

A double stranded RNA-DNA hybrid 7.2 Kb in length is functionalized at one terminus with biotin. At the other terminus, the DNA comprises a single stranded sequence of 15 bases repeated 4 times (5'-GTC TAT CAT CAC AGC GTC TAT CAT CAC AGC GTC TAT CAT CAC AGC GTC TAT CAT CAC AGC-3'; SEQ ID NO:2). Thus, the DNA comprises four binding sites at one terminus for selective immobilization. The hybrid also has four regions with Cy3 fluorophores incorporated into the RNA.

A small sample of the DNA (3 µL, 0.01 fmol/µL in 1×TAE, or 40 mM Tris acetate, 1 mM EDTA, pH 8.0) is transferred into a microfluidic device comprising a channel molded into polydimethylsiloxane that is passively adhered to a streptavadin coated coverslip (Accelr8, TB0200). The channel dimensions are 50 µm×1 mm×10 mm. See FIG. 15A. The sample is contacted with the coverslip at room temperature for 15 minutes allowing the DNA to selectively bind the streptavadin surface via the biotin at the terminus of the DNA. Unbound DNA is washed away by fluid flow. The 1×TAE buffer in the wells are exchanged for fresh buffer and fluid levels are evened out at 30 µL each well. See FIG. 4A.

An electric field of 200 V/cm is applied to extend the long negatively charged DNA (see FIG. 15B) toward the positive electrode.

An immobilization agent, a biotinylated oligonucleotide (5'-Biotin GCTGTGATGATAGAC-3', SEQ ID NO:3, 50 µL @ 100 nM, 1×TAE) complementary to the second terminus of the DNA, is added to the negative well. The additional volume raises the fluid level in the well and induces hydrostatic flow to introduce the immobilization reagent into the channel (see FIG. 15C). The flow also acts to further stretch the DNA in addition to the electric field.

The biotinylated oligonucleotide hybridizes with the second terminus of the DNA while it is extended and selectively binds the streptavidin of the coverslip. The sample can be effectively immobilized in an extended state in less than 5 minutes.

Imaging of selectively immobilized, extended macromolecules. A macromolecule comprising fluorophore labels and biotin affinity tags is prepared and purified according to examples provided below. The macromolecule is bound to a coverslip surface comprising biotin and stretched with an electric field. Finally macromolecule is illuminated with an Arc lamp and imaged with a camera. An exemplary image is provided in FIG. 16. Individual dyes and, significantly, the order of those dyes on individual macromolecules can be detected in the image.

Preparation and Imaging of Selectively Immobilized, Extended Macromolecules. Herein is a step-by-step example of the construction of a nanoreporter from various components. It can be appreciated that various components can be constructed or added either at the same time, before or after other components. For example, annealing patch units or flaps to a scaffold can be done simultaneously or one after the other.

In this example the starting material is a circular M13mp18 viral vector. Using a single linear strand M13mp18, patch units are annealed to it to form a double stranded scaffold. Next, flaps are added and then a target-specific sequence is ligated. Meanwhile purification steps aid to filter out excess, unattached patch units and flaps. Constructions of labeled nucleic acids (patches and/or flaps and/or other labeled oligonucleotides) that bind the nanoreporter are also described.

Upon attachment (e.g., via hybridization) of a target molecule, the nanoreporter is attached to a surface and stretched. Finally the nanoreporters are imaged by a camera. Nanoreporters were generated and successfully employed to detect target molecules using methods substantially as described in this example.

Scaffold construction. The oligonucleotide scaffold sequence selected was analyzed using Vector NTI® software. First, a single stranded nucleic acid was made from linearizing a circular M13mp18 single stranded DNA, which was commercially purchased from New England Biolabs. The circular M13mp18 was digested with BamH1 enzyme to linearize it. Materials used consisted of M13mp18 vector (250 ng/µl), Patch_1L_BamH1.02 (10 µM dilution of a 100 µM stock), 10× BamH1 Buffer, BamH1 enzyme. The protocol for making 0.8 pmol total of linear M13mp18 involves the following steps. 1) preheat heating block to 37° C.; 2) in a 0.65 ml ependorff tube combine 40 µl of 250 ng/µl M13mp18 vector, 2 µl of 10 µM Patch_1L_BamH1.02, and 5 µl of 10× BamH1 Buffer; 3) place the ependorff tube in the 37° C. heating block with foil over the top. Incubate the tube at 37° C. for 15 minutes to allow the patch unit to hybridize to the M13mp18 scaffold; 4) after 15 minutes add 2 µl of BamH1 enzyme and let the reaction digest at 37° C. for 30 minutes, after which add an additional 2 µl of BamH1 enzyme and let the reaction continue to digest for another 30 minutes at 37° C. (final volume of BamH1 enzyme is 8%); and 5) aliquot 10 µl into 0.65 ml ependorff tubes and store in freezer (final concentration of linear M13mp18 is 200 ng/µl).

Patch unit preparation of the base patch pools (BPP). Second, patch units are prepared in pools. Patch oligonucleotide sequences were selected for optimal length and desired homology/non-homology to M13mp18 strand and the human genomic sequence. Patches were commercially manufactured oligonucleotides (purchased from Integrated DNA technologies) either 60 or 65 nucleotide bases in length. Fifty nucleotide bases of each patch oligonucleotide are complementary to the M13mp18 single stranded DNA, 10 nucleotide bases are complementary to an adjacent patch, and 5 nucleotides base pairs are complementary to a corresponding flap. The 10 nucleotide base match between patches forms a stem structure which stabilizes the structure and helps lift the flaps off the covered scaffold so they are more available to bind labeled oligonucleotides. Synthetic binding sites, the five nucleotide bases, on the patches for binding to the flaps make leveraging the power of a modular system possible.

The base patch pools contain nine patch units all corresponding to a specific letter grouping and position on the nanoreporter. For this example, there are four different fluorescent dyes (color) labeled A, B, C, and D and 8 different positions or regions where labeled nucleic acids can bind on a nanoreporter. For example, BPP A3 corresponds to all of the A patch units at position 3 (patch units 19-27) on the nanoreporter.

The nanoreporter positions are as follows:
Position 1: Patch units 1-9 (A or C)
Position 2: Patch units 10-18 (B or D)
Position 3: Patch units 19-27 (A or C)
Position 4: Patch units 28-36 (B or D)
Position 5: Patch units 37-45 (A or C)
Position 6: Patch units 46-54 (B or D)
Position 7: Patch units 55-63 (A or C)
Position 8: Patch units 64-72 (B or D)

Materials: right and left patches, pre-annealed to each other (each oligonucleotide is at a concentration of 10 µM). Materials for making 100 pmol of BPP 1: (In position 1, patch coordinate 1 L is used for the BamH1 digest—this patch is not included in BPP 1): 10 µl each pre-annealed (10 µM/each) patch unit (coordinates 2-9), 5 µl [20 µM] Patch_1R (A or C). Final concentration of each patch is 1.18 pmol/µl. Materials for making 100 pmol of BPP 2-8: 10 µl each pre-annealed (10 µM/each) appropriate patch unit. There are 9 patch units added to each, or 90 µl total. Final concentration of each patch is 1.11 pmol/µl.

Below is a table of all the patch unit pools made for this example, with eight positions or regions for dye-labeled nucleic acids to bind on the nanoreporter. Positions 1, 3, 5, and 7 can bind to nucleic acid labeled with dye A or dye C, and a positions 2, 4, 6, and 8 can bind to nucleic acid labeled with dye B or dye D.

Table of resulting Basic Patch Pools (correspond to labels on tubes)

BPP-A1 [Pre-Paired, Color = A, Coordinates 1-9]
Patch_(1-9)R.A
Patch_(2-9)L
BPP-B2 [Pre-Paired, Color = B, Coordinates 10-18]
Patch_(10-18)R.B
Patch_(10-18)L
BPP-A3 [Pre-Paired, Color = A, Coordinates 19-27]
Patch_(19-27)R.A
Patch_(19-27)L -continued BPP-B4 [Pre-Paired, Color = B, Coordinates 28-36]
Patch_(28-36)R.B
Patch_(28-36)L
BPP-A5 [Pre-Paired, Color = A, Coordinates 37-45]
Patch_(37-45)R.A
Patch_(37-45)L
BPP-B6 [Pre-Paired, Color = B, Coordinates 46-54]
Patch_(46-54)R.B
Patch_(46-54)L
BPP-A7 [Pre-Paired, Color = A, Coordinates 55-63]
Patch_(55-63)R.A
Patch_(55-63)L
BPP-B8 [Pre-Paired, Color = B, Coordinates 64-72]
Patch_(64-72)R.B
Patch_(64-72)L
BPP-C1 [Pre-Paired, Color = C, Coordinates 1-9]
Patch_(1-9)R.C
Patch_(2-9)L
BPP-D2 [Pre-Paired, Color = D, Coordinates 10-18]
Patch_(10-18)R.D
Patch_(10-18)L
BPP-C3 [Pre-Paired, Color = C, Coordinates 19-27]
Patch_(19-27)R.C
Patch_(19-27)L
BPP-D4 [Pre-Paired, Color = D, Coordinates 28-36]
Patch_(28-36)R.D
Patch_(28-36)L
BPP-C5 [Pre-Paired, Color = C, Coordinates 37-45]
Patch_(37-45)R.C
Patch_(37-45)L
BPP-D6 [Pre-Paired, Color = D, Coordinates 46-54]
Patch_(46-54)R.D
Patch_(46-54)L
BPP-C7 [Pre-Paired, Color = C, Coordinates 55-63]
Patch_(55-63)R.C
Patch_(55-63)L
BPP-D8 [Pre-Paired, Color = D, Coordinates 64-72]
Patch_(64-72)R.D
Patch_(64-72)L Materials and preparation for annealing the single stranded oligonucleotide with patch units for a double stranded scaffold. Third, patch units are prepared to be annealed to the single stranded linear M13mp18, covering the strand in order to make a double stranded oligonucleotide scaffold. Conditions for annealing 60 and 65 nucleotide base patches to the M13mp18 need to occur at high salt concentrations so that binding will be very specific and patches will not anneal to an incorrect coordinate on the M13mp18 strand. For the annealing step, each patch unit is added at a 2:1 to 4:1 ratio with the single stranded M13mp18 sequence at 0.5 pmol total volume. Excess patches are removed before annealing flaps.

Materials used consisted of 20×SSC, linear M13mp18 (BamH1 digested at 0.08 pmol/µl or 200 ng/µl), appropriate base patch pools (BPP) (need 8 total at 1.11 pmol/µl—see above) and digital heat block set at 45° C. Annealing reaction make up is as follows. General guidelines: 2× each patch unit per M13mp18 molecule, pre-ligated flaps/patches (in position 1 or 8) added for purification later, and 5×SSC. Example (0.5 pmol of scaffold with F8 hook flaps) reaction consists of: 7.1 µl BamH1 Digested M13mp18 strand at 0.071 µM, 0.9 µl each new Base Patch Pools at 1.11 µM for first 7 positions: A1, B2, A3, B4, C5, B6 and A7:

1.7 µl A1 BPP (Pre-Annealed, 12/15; at 1.18 µM/each patch)
1.8 µl B2 BPP (Pre-Annealed, 12/15; at 1.11 µM/each patch)
1.8 µl A3 BPP (Pre-Annealed, 12/15; at 1.11 µM/each patch)
1.8 µl B4 BPP (Pre-Annealed, 12/15; at 1.11 µM/each patch)
1.8 µl C5 BPP (Pre-Annealed, 12/15; at 1.11 µM/each patch)
1.8 µl B6 BPP (Pre-Annealed, 12/15; at 1.11 µM/each patch)
1.8 µl A7 BPP (Pre-Annealed, 12/15; at 1.11 µM/each patch),
2.4 µl BPP-D8 (pool of the first seven patch units—coordinates 64, 65, 66, 67, 68, 69, and 70 at position 8—"D" specificity) with purification tags—F8 (FHF, which anneal to patch coordinates 71L, 71R, 72L, 72R, 73L making full split-flap/patch units that have "F" specificity for use as biotin linkers, at position F8) at 0.83 µM, and 7.3 µl 20×SSC. The final reaction volume will be 29.3 plat 0.027 pmol/µl.

Anti-Barn oligonucleotide is also added to anneal to region in M13 that is complementary to the (missing) 1 L patch unit and to prevent recircularization of the M13 scaffold during ligation.

Annealing patch units to single stranded m13mp18 to form a double stranded scaffold. The fourth step involves the protocol to anneal the patch units to the single stranded linear M13mp18, covering the strand in order to make a double stranded oligonucleotide scaffold, is performed in the following steps: 1) preheat heating block to 42° C., heat above reaction solution to 45° C. in small PCR (or strip) tube(s) with foil over top for 15 minutes, turn heat block to 65° C. and incubate for an additional 1 hour and 45 minutes and remove tubes, place on ice or freeze.

Purification of nanoreporter scaffold using biotin and magnetic beads with streptavidin. The fifth step occurs before attaching the flaps, where excess patch units that have not annealed to the M13mp18 strand are separated from the double stranded oligonucleotide scaffold. A purification tag with a five nucleotide base homologous region to some of the patch units' complementary five nucleotide base overhang is annealed to 'hook' the scaffold. Biotinylated oligonucleotides are annealed to the 'purification tag' and magnetic beads with streptavidin are used to capture the scaffold using the biotinylated oligonucleotides. Excess patch units are removed with the supernatant. The scaffold melts off of the magnetic beads into solution for recovery.

Anneal the d-biotin catchers to the purification tags. Anneal the D-Biotin catchers to the purification tags on the nanoreporter (making 2× to amount of D8-flap positions available in solution, which is 2> to M13, or 4× final): 0.5pmol×25 hook oligonucleotide positions (5 multiplied by 5), 4× makes 50 pmols translates to 0.50 µl of 100 pmol/µl D-biotin, add 0.5 µl (D, E, F)—Biotin (at 100 µM) to sample, mix and incubate at room temperature for 30 minutes.

Purification protocol to wash off unattached patch units from double stranded scaffold. Anneal F-hook oligonucleotides in a 25 fold excess to nanoreporters in 5×SSC for 30 min at room temperature. Pipet 200 µl DynaBead MyOne Streptavidin™ bead solution into 1.5 ml tubes, place on magnet and remove supernatant. Wash twice with 5×SSC by resuspending and clearing with magnet as in step above. Add 80 µl of sample in 5×SSC (80 fmoles of sample in this example). Resuspend well, by placing on vortex for 15 minutes. Clear solution with magnet and transfer supernatant to fresh tubes for later gel analysis. While on magnet, wash pellets (do not resuspend) with 80 µl TE by pipeting over pellet three times with the same 80 µl volume originally added. Remove wash, place in freshly "wash" tubes for analysis. Heat up TE buffer to 45° C., add 80 µl to each pellet and resuspend. Place tubes on 45° C. heat block for 15 minutes, pipetting up/down once to insure beads remain suspended.

Immediately clear product with magnet while warm and save. The majority of purified nanoreporters should be present in this product eluted at 45° C.

Annealing and ligation of flaps to scaffold. The sixth step involves split flap oligonucleotides which are annealed to the scaffold to make a 'covered scaffold.' Purification with magnetic beads is performed afterwards to remove excess split flaps. Ligation of the covered scaffold is done using T4 ligase to increase the stability of the structure. Only one type of flap is needed per fluorescent dye. Flaps are either 95 or 100 bases in length and have regions complementary to the patches, to labeled oligonucleotides and to each other. Each flap has 15 base repeating sequences for binding to labeled oligonucleotides. The repeat sequences are based on Lambda sequences that have been analyzed to remove any palindromes and hairpin structures.

Conditions for annealing the flaps are as follows. The sequence on the flaps that corresponds to the patch is 5 nucleotide base pairs long, and therefore the flaps anneal specifically to the patches even at high salt concentrations. The ratio of flaps to patches is 2:1. In order to increase stability at high temperatures, ligation of patches to each other and the flap to the patches may be carried out in the same reaction.

1) Quantify the purified scaffold using a spectrometer at A260 nm. Calculate the volume needed for appropriate amount of nanoreporter to prepare. For this example we used 110 ng or 0.023 pmol, reading at A260 nm shows 7.7 ng/µl, or 14.3 µl for 110 ng. 2) Setup ligation reaction as follows (volume will vary, depending on the purification and scale). Currently using 1.5× flaps to patches, calculate accordingly. For this example, there are four different fluorescent dyes (color) labeled A, B, C, and D and 8 different positions or regions where dye-labeled nucleic acids can bind on a nanoreporter. The number of positions for each color (in this case 1-4) multiply by 9 multiply by 1.5 moles of scaffold=moles of flaps to use.

For the nanoreporter with fluorescent dye in the sequence/positions [ABABCBAD]:

ABABCBAD=
A:40.5×0.023=0.93 pmol; vol: 0.93 ul of SF (split flap)-AL @1 µM
  0.93 µl of SF-AR at 1 µM
B:40.5×0.023=0.93 pmol; vol: 0.93 ul of SF-BL @1 µM
  0.93 µl of SF-BR at 1 µM
C:13.5×0.023=0.31 pmol; vol: 0.31 ul of SF-CL @1 µM
  0.31 µl of SF-CR at 1 µM
D:13.5×0.023=0.31 pmol; vol: 0.31 ul of SF-DL @1 µM
  0.31 µl of SF-DR at 1 µM Ligation reaction (25 µl total) consists of: Split Flaps (see above; 4.96 µl, or ~5 µl total), 14.3 µl of MODB-Scaffold at 0.0016 pmol/µl, 2.5 µl 10× T4 ligation Buffer, 2.2 µl NanoPure H2O and 1 µl T4 ligase. Incubate tubes 5 minutes at 45° C. Move to 37° C. water bath, inc. for 5 min. Add 1 µl T4 ligase to samples. Incubate for additional 1 hour at 37° C. Freeze immediately, or heat at 75° C. for 5 minutes to kill T4 ligase.

Ligation of target-specific sequences to nanoreporters. The seventh step involves ligation of a target-specific sequence to the nanoreporter. A DNA target-specific sequence is designed to be complementary to the target molecule, which can be RNA (e.g., mRNA) or DNA (e.g., cDNA or genomic DNA). The target-specific sequence can be from 35, 60 or 70 nucleotide bases in length. The target-specific sequence can be ligated to the scaffold using a single stranded overhanging region on the covered scaffold. The scaffold with a single type of target-specific sequence can be manufactured separately and then mixed to form libraries.

Nanoreporter construction. Addition of oligonucleotides to a nanoreporter can be done at any point during the construction of a nanoreporter. In certain aspects of the present invention, a labeled oligonucleotide is 15 nucleotide bases long. On the 5' end, a single fluorophore dye is attached. Oligonucleotides with a particular fluorophore dye will generally have the same sequence. These labeled oligonucleotides bind to the repeat sequences of the split flaps. Fluorophores best suited for this example include but are not limited to Alexa 488, cy3, Alexa 594, and Alexa 647. The 15 nucleotide base length holds the fluorophores far enough apart so that they cannot quench each other and ensure that the labeled nucleic acids will be stable (will not melt off complementary strand) at conditions in the visualization process. Labeled oligonucleotides are stable at 40° C. This short length also allows for packing a large number of fluorescent dyes onto the flaps. In certain aspects of the invention, labeled oligonucleotides are introduced during the target sample processing.

Attachment of nanoreporters to target molecules. Nanoreporters can be attached to target molecules using any means known to one of skill in the art. In an exemplary embodiment, dual nanoreporters are hybridized to target molecules by mixing 250 pmols each of both the first probe and the second probe with 125 pmols of target. The total volume is adjusted to 4 µl and a final concentration of buffer of 5×SSC. This mixture is incubated in a covered PCR tube overnight at 42 degrees to allow hybridization to occur.

Surface attachment. Once the nanoreporters are attached to both target molecule and corresponding labeled nucleic acids, i.e., nucleic acids attached to label monomers, they are attached to a surface and stretched in resolve the order of signals emitted by the label monomers and thus identify the target molecule. In this example, the nanoreporters are stretched to spatially resolve their fluorescent dye codes which correspond to a particular target molecule. The nanoreporters are stretched by attaching one end to a surface (in this example—a coverslip, see preparations below). Two methods for surface attachment may be used: A) streptavidin coated slides from Accelr8 Corporation with the nanoreporters being biotinylated and B) biotin coated slides with the nanoreporters having streptavidin. In buffer, the nanoreporters are brought into contact with the active surface and allowed to incubate for a period of time. The reaction is performed in flow cells which were made from PDMS molded in etched silicon wafers to make the channels. Metal tubing is used to core wells at the ends of the channels for buffer and sample insertion. Channel dimensions are 0.5 mm or 1 mm wide and 54 µm high. Once the sample has been loaded into the flow cell lane and incubated, the nanoreporters should be attached. Nanoreporters can be stretched either by applying a voltage or by removing the liquid with a receding meniscus leaving the strings stretched and dry.

Preparation of surface and assembly of device. The binding surfaces (Accelr8 brand Streptavidin-OptiChem, coated coverslips) are shipped in units of 5 surfaces per slide container, and each container is enclosed with a package of silica dessicant in a foil pouch. The pouches are stored at −20° C. until use. To prepare the surface for binding, a pouch is first pulled from the freezer and allowed to come to room temperature over several minutes. If previously unopened, the pouch is then sliced along one edge to form a slit, and the container of surfaces is removed. Upon removal of the required surface, the container is replaced in the pouch with its dessicant, the slit is sealed closed with a strip of packaging tape, and the pouch is replaced in the freezer.

The surface is then lightly rinsed with a stream of Nanopure water (Barnstead Nanopure Diamond) and soaked for 10 minutes in 0.2 m-filtered 1×PBS in a clean, slotted Coplin jar. After soaking, the surface is dipped in Nanopure water and dried by blowing filtered nitrogen across the surface edge.

The PDMS device used to mate with the surface and provide localization of the sample is cleaned just before use by applying cellophane tape to the PDMS surface and then peeling away dust or other particles which may have become attached during storage. The binding side of the Accelr8 surface is laid face-up, and the clean PDMS structure is centered, channel side down, on the surface. PDMS adheres readily to coated glass, and no further attachment mechanism is necessary.

Sample binding and washing. The sample is bound to the surface by first applying a five μL drop of the sample (currently diluted in 100 mM sodium borate buffer, pH 9.8) in one well of the chosen lane. The drop should just touch the point at which the channel joins the well (some sample may wick into the channel at this point). The channel is filled, and binding is equalized throughout the channel, by pulling the droplet through the channel to the opposite well using a very weak vacuum (<2 kPa). The process is repeated for the other samples in their respective lanes. Excess fluid is then removed from the wells, the wells are taped to reduce evaporation, and the device is incubated at room temperature in the dark for 20 minutes.

After binding, the tape is removed, and the top well of each lane is filled with 100 μL of the borate buffer described above. About 20 μL of that buffer is pulled through the channels to the other wells using the vacuum, and the process is repeated once. All borate buffer is then removed from all wells, and the top well is filled with 1×TAE, pH 8.3. About 50 μL TAE is pulled through the channel, then all TAE is removed and the well is refilled. The process is repeated three times, for a total of about 150 μL of TAE rinse. Finally, all wells are filled with 100 μL 1×TAE.

Electrostretching. The bottom of the coverslip/PDMS device is spotted with immersion oil and placed on the microscope. Electrodes are inserted into the wells on opposite ends of the first PDMS channel (negative electrode in top well, positive in bottom). The first image of the channel will be taken close to the bottom well; the microscope stage is adjusted so that the area of interest is in focus. Voltage (200 V) is then applied across the channel. Voltage is supplied by a DC power supply (Agilent E3630A) and amplified 100× through a home-built amplifier. After the current is applied, focus is readjusted, and the imaging process begins. The electrostretching and imaging process is then repeated with the remaining channels. Image the bindings.

Light source for the fluorescent dyes on the nanoreporter. In using an arc lamp as a light source, the best fluorophore selection is the brightest types without leading to fluorescent overlap such as Alexa 488, Cy3, and Alexa 594. Weaker fluorescent dyes such as Alexa 647 and Cy5.5 may also be used.

Filters to image the fluorescent dyes on the nanoreporter. For the selected fluorophores Alexa 488, Cy3, Alexa 594 and Alexa 647 there maybe an overlap between the Cy3 and Alexa 594. However, custom ordering an emission filter with a bandwidth of 572-600 nm minimizes the overlap.

Microscope and objective lens to image the nanoreporters. The microscope model used was the Nikon Eclipse TE2000E from Nikon Incorporation using the inverted fluorescence imaging station which has 6 filter cassettes that allow the selection of fluorescent emission from multiple fluorescent dye candidates. For the selected dyes, the optical resolution required is about 400 nm for all the wavelengths (500-700 nm). The selected objective lens is the Nikon Plan Apo TIRF lens which has a NA of 1.45 and magnification of 60. The optical resolution is ~210-300 nm for different wavelengths.

6.2 Example 2

Patch/Flap Nanoreporter Manufacturing Protocol

This example demonstrates another way of making a nanoreporter which consists of a single stranded linear M13mp18 viral DNA, oligonucleotide patch units and long flaps. Nanoreporter label units were successfully generated using methods substantially as described in this example. Pre-phosphorylated patch units and flaps are added together with the M13mp18 DNA vector and ligated together. After the ligation of the flaps to the patch units which are ligated to the M13mp18 DNA, the BamH1 enzyme is introduced to linearize the vector. Prepare a batch of nanoreporters starting with 5 μg of M13mp18 as a scaffold. The hybridization may be scaled up accordingly to the desired amount. This process will take about 1-2 days to complete.

Materials:

| Qty | Item | Vendor |
|---|---|---|
| 20 | 250 ug/ul M13mp18 viral ssDNA | New England Biolabs |
| 27 ul | 0.74 pmol/ul Oligonucleotide Patch Unit Mix | IDT |
| 8 ul | Long Flap Oligonucleotide A 100 pmol/ul | IDT |
| 8 ul | Long Flap Oligonucleotide B 100 pmol/ul | IDT |
| 0.5 ul | Flap patch Oligos @ 100 pmol/ul from plates #529916 and #610591 | IDT |
| 31 ul | T4 Ligase 10x buffer | Fermentas |
| 19 ul | T4 Ligase | Fermentas |
| 15 ul | Optikinase 10x buffer | USB |
| 4.2 ul | 100 mM ATP | ANY |
| 5 ul | Optikinase Enzyme 10 units/ul | USB |
| 1 ul | BamH1 oligonucleotide 10 pmol/ul | IDT |
| 20 ul | BamH1 10x buffer | Fermentas |
| 3 ul | BamH1 Enzyme 10 units/ul | Fermentas |

Preheat water bath to 37° C. and 55° C. before beginning protocol. Make sure buffers are all well mixed and thawed before using. A work plate should be available and labeled with the ordered oligos from IDT in plates #529916 and #610591. Take these two plates out and thaw at room temperature for 0.5-1 hours and spin down contents before removing the tape that covers the wells. Four separate reactions will be set up in 1.5 ml eppendorf tubes using specific oligonucleotides from these plates. To begin label these four separate tubes with roman numerals on their caps. Columns 5 and 6 A through H are for reaction I, Columns 7 and 8 A through H are for reaction ii are all found in plate #529916. Columns 1 and 2 are for reaction iv, and Columns 3 and 4 are for reaction iii.

Flap Ligations (Step A): Label four separate 1.5 ml tubes with roman numerals i through iv (mentioned above). Add the reagents below accordingly to each 50 μl reaction containing: 5 μl 10× ligase buffer, 0.5 μl/oligonucleotide from designated wells from plates #529916 and #610591, 4 μl Long Flap Oligo/reaction (A or B) for reactions I, ii and iv. 3 ul of LF for area iii, 29 H20 for reactions I, ii and iv. 32 μl H20 for reaction iii, and 4 μl T4 ligase. Preanneal oligos in this mix without the ligase at 37° C. for half an hour. Add ligase as last reagent and allow to ligate at room temperature for at least four hours. Product concentration is 1 pmol/flap/μl.

Flap Ligation Phosphorylation (Step B): Label four separate 1.5 ml tubes with roman numerals again, one through four with a P inside a circle to designate that the products are phosphorylated. Add the following reagents to the corresponding tube: 10 µl/Flap ligation. reaction (take 10 µl/flap ligation reaction above), 2.5 µl Optikinase buffer, 0.5 µl 100 mM ATP, 11.5 µl H20, and 0.5 µl Optikinase enzyme. Incubate at 37° C. for 1 hour. Product concentration 0.4 pmol/flap/µl.

Oligonucleotide Patch Unit Phosphorylation (Step C): 27 µl Oligonucleotide Patch Unit mix 0.74 pmol/µl, 5 µl 10× buffer, 1 µl 100 mM ATP, 3 µl Optikinase enzyme, and 14 µl H20. Once reagents are all together gently mix the solution by flicking the tube a few times and spin down. Incubate at 37° C. for 1 hour.

Hybridization to M13mp18 scaffold (Step D): In a new 1.5 ml tube add the following reagents: 20 µl M13mp18 at 250 ng/µl, 27 µl Phosphorylated Oligonucleotide Patch Units 0.4 pmol/µl (Step C), 12.5 µl/Phosph. Flap Ligation (Step B) preheat at 55° C. for 5 minutes and put on ice, 11 µl 10× ligase buffer and heat entire mixture at 55° C. for 1 minute. Hybridize mixture at 37° C. for at least 4 hours.

Ligation (Step E): Spin down eppendorf contents. Add 1.2 µl 100 mM ATP and 3 µl T4 ligase. Gently mix contents by flicking the tube, then spin down.

BamH1 Digest (Step F): 1 µl of 10 pmol BamH1 oligo, 20 µl 10× BamH1 buffer and hybride at 37~1 hour. Adjust volume to 200 µl. Add 3 µl BamH1 enzyme. Incubate at 37° C. for 1 hour.

First step: start by adding 20 µl of M13mp18 (NEB 250 µg/ml) to a clean 1.7 ml eppendorf tube. Take 5 µl of Phosphorylated Flap ligation reaction and preheat it at 70 for 2 minutes and immediately put on ice. Add the 5 µl of each Phosphorylated Flap Ligation reaction (1 pmol/flap/µl) to the tube and gently mix by pipetting a few times. Incubate the eppendorf tube at 37° C. for 1 hour.

Second step: put 13.5 µl Oligonucleotide Patch Unit Mix (0.74 pmol/pµl) and 1 µl of Acrydite Mix (10 pmol/µl) in a new eppendorf 1.7 ml eppendorf tube. Add 5 µl 10× Optikinase buffer, 1 µl 100 mM ATP and 27.5 µl H20. Mix gently by pipetting the solution. Add 2 µl Optikinase enzyme, gently mix by pipetting and incubate at 37° C. for 1 hr.

Third step: take the phosporylated oligos rxn and add it entirely to the contents of the M13mp18+Flaps Hybridization. The reaction is mixed gently by pipetting and it is allowed to incubate at 30° C. for 1 hour. After the hybridization is complete adjust the ATP by adding 1 µl (100 ATP) to the reaction.

Fourth step: spin down contents in eppendorf tube and add 4 µl T4 Ligase enzyme (5 units/µl), mix gently by pipetting. Incubate at room temperature for at least four hours. Add 1 µl BamHI oligonucleotide (10 pmol/µl) to hybridize at room temperature while ligation is taking place.

Fifth step: digest ligation reaction by adding 4 µl BamH1 enzyme (5 units/µl), mix gently by pipetting and incubate at 37° C. for 1 hour. Once the incubation period is over. Take an aliquot of 500 ng for QC.

Sixth step: treat with Psoralen, UV or DMPA light for 15 minutes.

Calculations include:

5 µg of M13=20 µl stock from New England Biolabs=2 pmols

Oligonucleotide mix: 180-34 flap areas-10 Acrydite modified Oligos=0.74 pmol/oligo 10 pmols/oligonucleotide=13.5 µl=1350 pmols Optikinase 1 unit converts 1 nmol of phosphate to ends—use excess. 4 µl of Optikinase was used.

6.3 Example 3

Protocol for Production of RNA Nanoreporters

Nanoreporters were generated and successfully employed to detect target molecules using methods substantially as described in this example. An example of target detection using such this method is shown in FIG. 6.

Scaffold Production. Single-stranded circular M13mp18 DNA (USB) was annealed to a 5-fold molar excess of an oligonucleotide complementary to the Bam HI recognition site (Bam Cutter oligo) and cut with Bam HI restriction enzyme to yield a linear single-stranded DNA backbone. An oligonucleotide complementary to the Barn Cutter oligonucleotide (anti-Bam oligonucleotide) was subsequently added in 50-fold excess to sequester free Bam Cutter oligonucleotide and thus prevent recircularization of the M13 during later steps. The linear M13 molecule serves as a scaffold onto which RNA patches, or RNA segments, with incorporated fluorophores can be annealed.

PCR to form double-stranded positions on the M13 scaffold. Ten sets of oligonucleotide primer pairs were designed to create 10 different regions along the M13 scaffold. Each pair contains one primer which has a T7 RNA polymerase promoter at the 5' end. Regions 2-7 are designed to be 900 bases (approximately 300 nm) long, as this is the approximate size of a diffraction-limited spot (the smallest spot that can be achieved with standard optics). Regions 1 and 8 have both long and short versions: the long versions cover the whole 900-base region, while the short versions cover only a portion of the 900-base region to allow a target-specific sequence to be ligated. Thus a target-specific sequence can be attached to either end. The ends can also be used for attachment of anchors or tags.

PCR is performed using Taq polymerase and 0.5 ng of double-stranded M13mp18 (USB) as a template. Reactions are cleaned up using a Qiaquick purification kit from Qiagen. Each PCR reaction yields a double-stranded fragment corresponding to one specific segment as illustrated below. These fragments are used as templates for the in vitro transcription of the RNA segments.

In vitro Transcription to Produce Dark RNA Segments. Using the PCR products described above as double-stranded templates, RNA segments are generated using an in vitro transcription kit from Ambion (Megascript T7 kit). The products of the transcription reactions are purified (including treatment with DNAse I to remove template) using a RNeasy Kit from Qiagen.

In vitro Transcription to Produce RNA Segments Modified With Aminoallyl Groups. Using the PCR products described above as double-stranded templates, RNA segments for later dye-coupling are generated using an in vitro transcription kit from Ambion (MessageAmp aRNA kit). Aminoallyl-modified UTP nucleotides are incorporated into the RNA segments during transcription. The products of the transcription reactions are purified (including treatment with DNAse I to remove template) using a RNeasy Kit from Qiagen.

Dye Coupling of Aminoallyl RNA Segments to Produce Colored RNA Segments. 20-100 µg of aminoallyl-modified RNA segment is coupled with NHS-ester dyes using Ambion Aminoallyl Labeling Kit. Dyes used include Alexa 488, Alexa 594 and Alexa 647 (Invitrogen/Molecular Probes) as well as Cy3 (Amersham).

Each segment is made separately in four colors so that each position on the scaffold can be filled with a segment in any of the four colors; thus different colors can be added at different positions to create many unique color combinations.

In this particular embodiment, adjacent segments must be of different colors or there may be dark segments interspersed so that each segment is detected as an individual 'spot'. Dark segments may be used as part of the nanoreporter code.

Assembly of the Label Molecule. Segments for each position are annealed in a 2:1 ratio of segment to M13 scaffold in 1×SSPE buffer at 70° C. for 2 hours. An assembled nanoreporter with labeled RNA segments is depicted in FIGS. 3A and 3B. FIG. 3A depicts a nanoreporter in which only alternate "spots" (1, 3, 5 and 7) are labeled, and FIG. 3B depicts a nanoreporter in which every spot is labeled.

6.4 Example 4

Detection of Target (S2) RNA AND DNA Molecules Using an RNA Nanoreporter/Ghost Probe Combination Synthesis of Probe and Target Oligonucleotides. S2 DNA target oligonucleotide was synthesized and purified by polyacrylamide gel electrophoresis (Integrated DNA Technologies). S2 RNA target molecules were generated by in vitro transcription of PCR products corresponding to region of cloned SARS coronavirus gene (Invitrogen) using an Ambion Megascript™ kit per manufacturer's instructions. The S2 ghost probe (FIG. 6A (i) was complementary to a specific 50-base region of the S2 target sequence (S2-a) and was synthesized with a biotin-TEG monomer at the 5' end and purified by high performance liquid chromatography (Integrated DNA Technologies). A second oligonucleotide with 50 bps complementary to the S2 target (S2-b) plus 9 by of a additional sequence used for ligation to the M13 scaffold (59 bp total) was synthesized and purified by HPLC (Integrated DNA Technologies). Note that S2-a and S2-b target regions were not overlapping.

Nanoreporter synthesis. Oligonucleotide S2-b was ligated to the 5' end of linearized M13 [FIG. 6A (iii)], and the resulting product was purified away from residual unligated oligonucleotide by size-exclusion filtration through a YM100 filter (Millipore) per manufacturer's instructions. Amino-allyl-modified RNA segments complementary to M13 is positions 2, 4, 6, and 8 (FIG. 1C) were generated from in vitro-transcription of DNA templates (PCR products) via the Ambion Megascript™ kit per manufacturer's instructions. The segments were then coupled to NHS-ester-modified Alexa 647 dye (Invitrogen) per Ambion's instructions (amino allyl MessageAmp™ II aRNA kit). RNA segments corresponding to positions 1, 3, 5, and 7 of the M13 scaffold (FIG. 1C) were generated as unmodified in vitro-transcribed RNAs from DNA templates as described above. Assembly of the nanoreporter was carried out by annealing 10 fmol/μl of each of the eight segments to 5 fmol/μl of the M13-S1-b scaffold for 2 hours at 70° C. in 1×SSPE buffer (150 mM sodium chloride, 10 mM sodium phosphate, 1 mM EDTA). The final product was a nanoreporter with 4 segments labeled with A647 (red) interspersed with dark segments.

Hybridization conditions. Hybridization of nanoreporters and ghost probes to target were carried out under the following conditions: 5×SSPE (750 mM sodium chloride, 50 mM sodium phosphate, 5 mM disodium EDTA), 40 pM ghost probe (attachment oligonucleotide S2-a), 40 pM Nanoreporter S2-b, 100 ng/μl sheared salmon sperm DNA, 5× Denhardt's solution and 0.1% Tween. Final target concentrations were 20 pM S2 DNA target (FIG. 6B) and 1 pM S2 RNA target (FIG. 6C). No target was added to the negative control (FIG. 6C). The hybridization reaction was incubated at 65° C. for at least 16 h.

Hybridization reactions were diluted 1:2 with 100 mM Borate buffer solution (pH 9.8) and introduced into a flow cell channel and bound to a streptavidin-coated coverslip forming the bottom of the channel (Streptavidin-OptiChem coverslips from Accelr8). Attachment to the slide by one end of the nanoreporter/target/ghost probe complex was achieved via interaction of the biotinylated ghost probe with the streptavidin surface. After rinsing the channel with additional borate buffer to remove excess reporters not bound to the surface, the buffer was exchanged with 1×TAE (40 mM Tris-acetate, 1 mM EDTA) and a current of 200V was applied to stretch out the nanoreporter/target complexes during image capture.

Images were obtained using a Leica DMI 6000B microscope with a 63× oil immersion objective (1.4 NA), Xcite-120 light source (Exfo), customized filter sets (Chroma Technologies), an Orca-ER CCD camera (Hamamatsu) and Metamorph data acquisition software (Molecular Devices). As predicted, when the correct target molecule S2 hybridizes [FIG. 6A (ii)] to both ghost probe [FIG. 6A (i), S2-a] and S2-b target-specific nanoreporter [FIG. 6A (iii)], the ghost probe/target/nanoreporter complex forms a single species that attaches to the slide and was visualized as 4 spots when exposed to 647 nm wavelength light (FIGS. 6B, 6C, and 6E). The amount of binding was dependent on the target concentration. There was no significant binding in absence of S2 target sequence (FIG. 6D).

6.5 Example 5

Nanoreporter Comprising a Monovalent Antibody Fragment

Where a target molecule is a protein or polypeptide, a nanoreporter can be generated in which the nanoreporter scaffold is a nucleic acid and the target-specific sequence is a monovalent antibody fragment. Using routine methods, an antibody that recognizes a target molecule of interest is optionally digested with pepsin to generate F(ab')2 fragments. The two parts of the antibody or the two F(ab')2 fragments generated by the pepsin digestion are separated by mild reduction, for example with 2-mercaptoethylamine. This reduction separates either the antibody or the two F(ab')2 fragments into two monovalent fragments with two sulfhydryl groups that can be functionalized.

A heterobifunctional crosslinking reagent (e.g., m-Maleimidobenzoyl-N-hydroxysuccinimide ester from Pierce Biotechnology Inc.) is used to attach a maleimide to an oligonucleotide with an amine modification (which can be ordered from many sources, such as Integrated DNA Technologies). The NHS on the cross-linking reagent is reacted with the amine on the oligonucleotides to produce a maleimide-conjugated oligonucleotide.

This maleimide conjugated oligonucleotide is then reacted with one of the sulfhydryl groups on the antibody fragment. Due to steric limitations, it is preferable that only one oligonucleotide is be attached to each fragment. This monovalent antibody fragment attached to an oligonucleotide can then be hybridized to a complementary sequence on a nanoreporter scaffold, to generate a nanoreporter in which the target-specific sequence is an antibody sequence.

Surface attachment. Once the nanoreporters are attached to both target molecule and corresponding labeled nucleic acids, i.e., nucleic acids attached to label monomers, they are attached to a surface and stretched in resolve the order of signals emitted by the label monomers and thus identify the target molecule. In this example, the nanoreporters are stretched to spatially resolve their fluorescent dye codes which correspond to a particular target molecule. The nanoreporters are stretched by attaching one end to a surface (in this example—a coverslip, see preparations below). Two methods for surface attachment may be used: A) streptavidin coated slides from Accelr8 Corporation with the nanoreporters being biotinylated and B) biotin coated slides with the nanoreporters having streptavidin. In buffer, the nanoreporters are brought into contact with the active surface and allowed to incubate for a period of time. The reaction is performed in flow cells which were made from PDMS molded in etched silicon wafers to make the channels. Metal tubing is used to core wells at the ends of the channels for buffer and sample insertion. Channel dimensions are 0.5 mm or 1 mm wide and 54 µm high. Once the sample has been loaded into the flow cell lane and incubated, the nanoreporters should be attached. Nanoreporters can be stretched either by applying a voltage or by removing the liquid with a receding meniscus leaving the strings stretched and dry.

Preparation of surface and assembly of device. The binding surfaces (Accelr8 brand Streptavidin-OptiChem, coated coverslips) are shipped in units of 5 surfaces per slide container, and each container is enclosed with a package of silica dessicant in a foil pouch. The pouches are stored at −20° C. until use.

To prepare the surface for binding, a pouch is first pulled from the freezer and allowed to come to room temperature over several minutes. If previously unopened, the pouch is then sliced along one edge to form a slit, and the container of surfaces is removed. Upon removal of the required surface, the container is replaced in the pouch with its dessicant, the slit is sealed closed with a strip of packaging tape, and the pouch is replaced in the freezer.

The surface is then lightly rinsed with a stream of Nanopure water (Barnstead Nanopure Diamond) and soaked for 10 minutes in 0.2 µm-filtered 1×PBS in a clean, slotted Coplin jar. After soaking, the surface is dipped in Nanopure water and dried by blowing filtered nitrogen across the surface edge.

The PDMS device used to mate with the surface and provide localization of the sample is cleaned just before use by applying cellophane tape to the PDMS surface and then peeling away dust or other particles which may have become attached during storage. The binding side of the Accelr8 surface is laid face-up, and the clean PDMS structure is centered, channel side down, on the surface. PDMS adheres readily to coated glass, and no further attachment mechanism is necessary.

Sample Binding and Washing. The sample is bound to the surface by first applying a 5 µL drop of the sample (currently diluted in 100 mM sodium borate buffer, pH 9.8) in one well of the chosen lane. The drop should just touch the point at which the channel joins the well (some sample may wick into the channel at this point). The channel is filled, and binding is equalized throughout the channel, by pulling the droplet through the channel to the opposite well using a very weak vacuum (<2 kPa). The process is repeated for the other samples in their respective lanes. Excess fluid is then removed from the wells, the wells are taped to reduce evaporation, and the device is incubated at room temperature in the dark for 20 minutes.

After binding, the tape is removed, and the top well of each lane is filled with 100 µL of the borate buffer described above. About 20 µL of that buffer is pulled through the channels to the other wells using the vacuum, and the process is repeated once. All borate buffer is then removed from all wells, and the top well is filled with 1×TAE, pH 8.3. About 50 µL TAE is pulled through the channel, then all TAE is removed and the well is refilled. The process is repeated three times, for a total of about 150 µL of TAE rinse. Finally, all wells are filled with 100 µL 1×TAE.

Electrostretching. The bottom of the coverslip/PDMS device is spotted with immersion oil and placed on the microscope. Electrodes are inserted into the wells on opposite ends of the first PDMS channel (negative electrode in top well, positive in bottom). The first image of the channel will be taken close to the bottom well; the microscope stage is adjusted so that the area of interest is in focus.

Voltage (200 V) is then applied across the channel. Voltage is supplied by a DC power supply (Agilent E3630A) and amplified 100× through a amplified by a high voltage amplifier (Matsusada Precision Inc.). After the current is applied, focus is readjusted, and the imaging process begins.

The electrostretching and imaging process is then repeated with the remaining channels. Image the nanoreporters.

Light source for the fluorescent dyes on the nanoreporter. In using an arc lamp as a light source, the best fluorophore selection is the brightest types without leading to fluorescent overlap such as Alexa 488, Cy3, and Alexa 594. Weaker fluorescent dyes such as Alexa 647 and Cy5.5 may also be used.

Filters to image the fluorescent dyes on the nanoreporter. For the selected fluorophores Alexa 488, Cy3, Alexa 594 and Alexa 647 there maybe an overlap between the Cy3 and Alexa 594. However, custom ordering an emission filter with a bandwidth of 572-600 nm minimizes the overlap.

Microscope and objective lens to image the nanoreporters. The microscope model used is the Nikon Eclipse TE2000E from Nikon Incorporation using the inverted fluorescence imaging station which has 6 filter cassettes that allow the selection of fluorescent emission from multiple fluorescent dye candidates. For the selected dyes, the optical resolution required is about 400 nm for all the wavelengths (500-700 nm). The selected objective lens is the Nikon Plan Apo TIRF lens which has a NA of 1.45 and magnification of 60. The optical resolution is ~210-300 nm for different wavelengths.

Five minutes before using the microscope (Nikon Eclipse TE2000E), turn on the light source (X-cite 120, Exfo Corporation) and make sure the intensity is the maximum. Turn on the CCD camera driver (Hamamatsu, Orca Ag) and the shutter controller. Use the oil objective of 60×1.45NA (Plan Apo TIRF, Nikon) to evaluate the nanoreporters. For all the nanoreporter evaluations the optivar is set at 1×. Open the Metamorph software (Universal Imaging Corporation). Acquire the images using the corresponding filter sets such as cy3, A647 (Chroma Technologies).

7. REFERENCES CITED

All publications, patents and patent applications cited in this specification are herein incorporated by reference to the same extent as if each individual publication or patent or patent application was specifically and individually indicated to be incorporated by reference in its entirety herein for all purposes.

The present invention can be implemented as a computer program product that comprises a computer program mechanism embedded in a computer readable storage medium. For instance, the computer program product could contain the program modules shown in FIG. 9. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The program modules in the computer program product can also be distributed electronically, via the Internet or otherwise, by transmission of a computer data signal (in which the software modules are embedded) either digitally or on a carrier wave.

Many modifications and variations of this invention can be made without departing from its spirit and scope, as will be apparent to those skilled in the art. For instance, data storage module 44, label identification module 50, and probe identification module 54 can be combined into a single program, can each be a separate program, or could, in fact, be dispersed in multiple (e.g., three or more) programs. The specific embodiments described herein are offered by way of example only, and the invention is to be limited only by the terms of the appended claims, along with the full scope of equivalents to which such claims are entitled.

What is claimed is:

1. A computer program product, wherein the computer program product comprises a non-transitory computer readable storage medium containing a computer program mechanism embedded therein, the computer program mechanism for detecting the presence of a probe within a sample overlayed on a substrate, wherein the probe comprises a plurality of spatially arranged labels, the computer program mechanism comprising:

a data storage module comprising instructions for storing a plurality of light images, each light image in the plurality of light images being for light received from the sample at a wavelength range in a plurality of different wavelength ranges;

a label identification module comprising instructions for identifying a plurality of labels, in the plurality of light images, that are proximate to each other on the substrate, wherein a spatial order of the plurality of labels determines a string sequence of the plurality of labels; and a probe identification module comprising instructions for determining whether the string sequence of the plurality of labels comprises a valid reporter sequence, wherein
when the string sequence of the plurality of labels is confirmed as a valid reporter sequence, the plurality of labels is deemed to be the probe; and
when the string sequence of the plurality of labels is not confirmed as a valid reporter sequence, the plurality of labels is deemed to not be the probe.

2. The computer program product of claim 1, wherein a first label in the plurality of labels is associated with a first position on the substrate that emits light in a first wavelength range in the plurality of different wavelength ranges and a second label in the plurality of labels is associated with a second position on the substrate that emits light in a second wavelength range in the plurality of different wavelength ranges.

3. The computer program product of claim 2, wherein a portion of the first wavelength range overlaps with a portion of the second wavelength range.

4. The computer program product of claim 2, wherein the first wavelength range does not overlap with the second wavelength range.

5. The computer program product of claim 1, wherein each label in the plurality of labels is associated with a position on the substrate that emits more than a threshold amount of light in at least one light image in the plurality of light images.

6. The computer program product of claim 1, wherein the computer program mechanism further comprises a lookup table comprising a plurality of valid reporter sequences, and wherein the probe identification module further comprises instructions for comparing the string sequence of the plurality of labels to valid reporter sequences in the lookup table.

7. The computer program product of claim 6, wherein the lookup table is dimensioned and configured to hold up to $4^4$ different valid reporter sequences.

8. The computer program product of claim 6, wherein the lookup table is dimensioned and configured to hold up to $7^4$ different valid reporter sequences.

9. The computer program product of claim 6, wherein the lookup table is dimensioned and configured to hold more than 8 different valid reporter sequences.

10. The computer program product of claim 1, the probe identification module further comprising instructions for storing the string sequence of the plurality of labels that is not confirmed as a valid reporter sequence.

11. The computer program product of claim 1, wherein the data storage module further comprises instructions for aligning a first light image to a second light image in the plurality of light images using a plurality of fiducials present on the substrate.

12. The computer program product of claim 1, wherein the position of the probe on the substrate is random.

13. The computer program product of claim 1, wherein the probe consists of a single molecule.

14. The computer program product of claim 1, wherein the probe comprises a molecular scaffold and wherein each label in the plurality of labels represents a different position on said molecular scaffold.

15. The computer program product of claim 14, wherein each position on said molecular scaffold that is represented by a label is separated from a neighboring position on the scaffold by a spacer.

16. The computer program product of claim 1, wherein the probe comprises a single stranded deoxynucleic acid or ribonucleic acid scaffold and wherein each label in the plurality of labels is represented by a dye laden single stranded deoxynucleic acid or ribonucleic acid sequence that hybridizes to a different position on the scaffold.

17. The computer program product of claim 1, wherein
the probe comprises a molecular scaffold having a first end and a second end;
a target specific sequence is covalently attached to the first end;
a binder sequence is covalently attached to the second end; and
the probe is linearly arranged on the substrate through (i) the binding of the target specific sequence to a first molecular entity that is bound to a first position of the substrate and (ii) the binding of the binder sequence to a second molecular entity that is bound to a second position on the substrate.

18. The computer program product of claim 17, wherein the first molecular entity is a target (single stranded deoxynucleic acid or ribonucleic acid)-biotin complex, and the second molecular entity is a predetermined (single stranded deoxynucleic acid or ribonucleic acid)-biotin complex.

19. The computer program product of claim 1, wherein the label identification module further comprises instructions for identifying a plurality of candidate labels in the plurality of light images, and wherein said plurality of labels is a subset of the plurality of candidate labels that have been validated by the label identification module.

20. The computer program product of claim 19, wherein each candidate label in the plurality of candidate labels is associated with a position on the substrate that emits more than a threshold amount of light in any one light image in the plurality of light images.

21. The computer program product of claim 19, wherein the plurality of labels comprises a first candidate label that is associated with a first position on the substrate that emits light in a first wavelength range in the plurality of different wavelength ranges and a second candidate label that is associated with a second position on the substrate that emits light in a second wavelength range in the plurality of different wavelength ranges.

22. The computer program product of claim 21, wherein a portion of the first wavelength range overlaps with a portion of the second wavelength range.

23. The computer program product of claim 21, wherein the first wavelength range does not overlap with the second wavelength range.

24. The computer program product of claim 19, wherein the instructions for identifying the plurality of labels applies a first distance criterion between a centroid of a first candidate label and a centroid of a second candidate label in the plurality of candidate labels.

25. The computer program product of claim 24, wherein the first distance criterion is determined by a calculated distance between a first label and a second label in the probe.

26. The computer program product of claim 24, wherein the instructions for identifying the plurality of labels applies a second distance criterion between a centroid of the second candidate label and a centroid of a third candidate label in the plurality of candidate labels.

27. The computer program product of claim 26, wherein the second distance criterion is determined by a calculated distance between a second label and a third label in the probe.

28. The computer program product of claim 26, wherein the first distance criterion is the same as the second distance criterion.

29. The computer program product of claim 26, wherein the first distance criterion is different from the second distance criterion.

30. The computer program product of claim 26, wherein a value of the first distance criterion and a value of the second distance criterion contribute to determining whether the plurality of labels is said probe.

31. The computer program product of claim 26, wherein the computer program mechanism further comprises a lookup table comprising a plurality of valid reporter sequences, wherein each valid reporter sequence in the plurality of valid reporter sequences comprises a first distance between a first pair of labels and a second distance between a second pair of labels, and wherein the probe identification module further comprises instructions for comparing the string sequence of the plurality of labels, the first distance criterion, and the second distance criterion, to valid reporter sequences in the lookup table.

32. The computer program product of claim 19, wherein the instructions for identifying the plurality of labels applies an angle criterion to triplets of candidate labels in the plurality of candidate labels.

33. The computer program product of claim 19, wherein the instructions for identifying the plurality of labels comprises instructions for applying a model to select candidate labels in the plurality of candidate labels.

34. The computer program product of claim 33, wherein the instructions for applying a model to select candidate labels comprises instructions for applying linear regression to the select candidate labels.

35. The computer program product of claim 19, wherein the label identification module further comprises instructions for verifying that a candidate label in the plurality of candidate labels satisfies a spot shape criterion.

36. The computer program product of claim 35, wherein the instructions for verifying that a candidate label in the plurality of candidate labels satisfies the spot shape criterion comprises instructions for performing point spread function modeling on the candidate label.

37. The computer program product of claim 35, wherein the instructions for verifying that a candidate label in the plurality of candidate labels satisfies the spot shape criterion comprises instructions for applying a spot segmentation algorithm to the candidate label.

38. The computer program product of claim 37, wherein the spot segmentation algorithm comprises a watershed transformation.

39. The computer program product of claim 19, wherein the instructions for identifying the plurality of labels applies an absolute distance criterion between a centroid of a first terminal candidate label and a centroid of a second terminal candidate label in the plurality of candidate labels.

40. The computer program product of claim 19, wherein the instructions for identifying the plurality of labels comprises instructions for identifying a buffer zone around a portion of the substrate that has select candidate labels in the plurality of candidate labels, wherein there are no candidate labels in the buffer zone.

41. The computer program product of claim 1, wherein the plurality of labels are linearly arranged on the substrate.

42. The computer program product of claim 1, wherein the plurality of labels are linearly arranged on the substrate in the same linear orientation.

43. The computer program product of claim 42, wherein a linear orientation of each label in the plurality of labels is predetermined.

44. The computer program product of claim 43, wherein a linear orientation of each label in the plurality of labels is determined by an application of an electrical current across said substrate.

45. The computer program product of claim 43, wherein a linear orientation of each label in the plurality of labels is determined by an application of a fluid across said substrate.

46. The computer program product of claim 1, wherein each respective label in the plurality of labels occupies between 4 and 20 pixels in a pixilated representation of the respective label in a light image in the plurality of light images.

47. The computer program product of claim 1, wherein each respective label in the plurality of labels occupies between 6 and 30 pixels in a pixilated representation of the respective label in a light image in the plurality of light images.

48. The computer program product of claim 1, wherein each respective label in the plurality of labels occupies between 1 and 30 pixels in a pixilated representation of the respective label in a light image in the plurality of light images.

49. The computer program product of claim 1, wherein each respective label in the plurality of labels occupies between 4 and 100 pixels in a pixilated representation of the respective label in a light image in the plurality of light images.

50. The computer program product of claim 1, wherein the label identification module further comprises:
  instructions for identifying a first candidate label in the plurality of light images; and
  instructions for identifying a second candidate label in the plurality of light images that is within a predetermined distance away from the first candidate label;
  wherein the plurality of labels comprises the first candidate label and the second candidate label.

51. The computer program product of claim 1, wherein the plurality of different wavelength ranges consists of between two different wavelength ranges and six different wavelength ranges.

52. The computer program product of claim 1, wherein the plurality of different wavelength ranges consists of between two different wavelength ranges and twenty different wavelength ranges.

53. The computer program product of claim 1, wherein the plurality of labels comprises four labels.

54. The computer program product of claim 1, wherein the plurality of labels comprises five labels.

55. The computer program product of claim 1, wherein the plurality of labels consists of between two labels and twenty labels.

56. The computer program product of claim 1, wherein a first subset of the labels in the string sequence error check an identity of the labels in a second subset of the labels in the string sequence.

57. The computer program product of claim 1, wherein a first subset of labels in the string sequence are a checksum for a second subset of labels in the string sequence.

58. The computer program product of claim 1, wherein
the label identification module comprises instructions for repeating said instructions for identifying a plurality of labels a plurality of times, wherein each time said instructions for identifying a plurality of labels is repeated, a different plurality of labels is identified, in the plurality of light images, that are proximate to each other on the substrate; and
wherein the probe identification module determines whether each said different plurality of labels identified by the label identification module comprises a valid reporter sequence wherein, for each said different plurality of labels, said probe identification module:
deems the different plurality of labels to be a probe when the string sequence of the different plurality of labels is confirmed as a valid reporter sequence; and
deems the different plurality of labels to not be a probe when the string sequence of the different plurality of labels is not confirmed as a valid reporter sequence.

59. The computer program product of claim 58, wherein a plurality of probes is identified.

60. The computer program product of claim 59, wherein said plurality of probes consists of three or more probes.

61. The computer program product of claim 59, wherein said plurality of probes consists of ten or more probes.

62. The computer program product of claim 59, wherein said plurality of probes consists of less than 50 probes.

63. The computer program product of claim 58, wherein said probe identification module stores each type of probe identified.

64. The computer program product of claim 58, wherein said probe identification model stores each string sequence of each different plurality of labels that is not confirmed as a valid reporter sequence.

65. The computer program product of claim 58, wherein said probe identification model stores each string sequence of each different plurality of labels that is confirmed as a valid reporter sequence.

66. A computer system for detecting the presence of a probe within a sample overlayed on a substrate, wherein the probe comprises a plurality of spatially arranged labels, the computer system comprising:
a central processing unit; and
a memory, coupled to the central processing unit, the memory storing:
a data storage module comprising instructions for storing a plurality of light images, each light image in the plurality of light images being for light received from the sample at a wavelength range in a plurality of different wavelength ranges;
a label identification module comprising instructions for identifying a plurality of labels, in the plurality of light images, that are proximate to each other on the substrate, wherein a spatial order of the plurality of labels determines a string sequence of the plurality of labels; and
a probe identification module comprising instructions for determining whether the string sequence of the plurality of labels comprises a valid reporter sequence, wherein
when the string sequence of the plurality of labels is confirmed as a valid reporter sequence, the plurality of labels is deemed to be the probe; and
when the string sequence of the plurality of labels is not confirmed as a valid reporter sequence, the plurality of labels is deemed to not be the probe.

67. The computer system of claim 66, wherein a first label in the plurality of labels is associated with a first position on the substrate that emits light in a first wavelength range in the plurality of different wavelength ranges and a second label in the plurality of labels is associated with a second position on the substrate that emits light in a second wavelength range in the plurality of different wavelength ranges.

68. The computer system of claim 67, wherein a portion of the first wavelength range overlaps with a portion of the second wavelength range.

69. The computer system of claim 67, wherein the first wavelength range does not overlap with the second wavelength range.

70. The computer system of claim 66, wherein each label in the plurality of labels is associated with a position on the substrate that emits more than a threshold amount of light in any one light image in the plurality of light images.

71. The computer system of claim 66, wherein the memory further stores a lookup table comprising a plurality of valid reporter sequences, and wherein the probe identification module further comprises instructions for comparing the string sequence of the plurality of labels to valid reporter sequences in the lookup table.

72. The computer system of claim 71, wherein the lookup table is dimensioned and configured to hold up to $4^4$ different valid reporter sequences.

73. The computer system of claim 71, wherein the lookup table is dimensioned and configured to hold up to $20^{20}$ different valid reporter sequences.

74. The computer system of claim 66, the probe identification module further comprising instructions for storing the string sequence of the plurality of labels that is not confirmed as a valid reporter sequence.

75. The computer system of claim 66, wherein the data storage module further comprises instructions for aligning a first light image to a second light image in the plurality of light images using a plurality of fiducials present on the substrate.

76. The computer system of claim 66, wherein the position of the probe on the substrate is random.

77. The computer system of claim 66, wherein the probe consists of a single molecule.

78. The computer system of claim 66, wherein the probe comprises a molecular scaffold and wherein each label in the plurality of labels represents a different position on said molecular scaffold.

79. The computer system of claim 78, wherein each position on said molecular scaffold that is represented by a label is separated from a neighboring position on the scaffold by a spacer.

80. The computer system of claim 66, wherein the probe comprises a single stranded deoxynucleic acid or ribonucleic acid scaffold and wherein each label in the plurality of labels is represented by a dye laden single stranded deoxynucleic acid or ribonucleic acid sequence that hybridizes to a different position on the scaffold.

81. The computer system of claim 66, wherein the probe comprises a molecular scaffold having a first end and a second end;
a target specific sequence is covalently attached to the first end;

a binder sequence is covalently attached to the second end; and the probe is linearly arranged on the substrate through (i) the binding of the target specific sequence to a first molecular entity that is bound to a first position of the substrate and (ii) the binding of the binder sequence to a second molecular entity that is bound to a second position on the substrate.

82. The computer system of claim 81, wherein
the first molecular entity is a target (single stranded nucleic acid or ribonucleic acid)-biotin complex, and
the second molecular entity is a predetermined (single stranded deoxynucleic acid or ribonucleic acid)-biotin complex.

83. The computer system of claim 66, wherein the label identification module further comprises instructions for identifying a plurality of candidate labels in the plurality of light images, and wherein said plurality of labels is a subset of the plurality of candidate labels that have been validated by the label identification module.

84. The computer system of claim 83, wherein each candidate label in the plurality of candidate labels is associated with a position on the substrate that emits more than a threshold amount of light in any one light image in the plurality of light images.

85. The computer system of claim 83, wherein the plurality of labels comprises a first candidate label is associated with a first position on the substrate that emits light in a first wavelength range in the plurality of different wavelength ranges and a second candidate label is associated with a second position on the substrate that emits light in a second wavelength range in the plurality of different wavelength ranges.

86. The computer system of claim 85, wherein a portion of the first wavelength range overlaps with a portion of the second wavelength range.

87. The computer system of claim 85, wherein the first wavelength range does not overlap with the second wavelength range.

88. The computer system of claim 83, wherein the instructions for identifying the plurality of labels applies a first distance criterion between a centroid of a first candidate label and a centroid of a second candidate label in the plurality of candidate labels.

89. The computer system of claim 88, wherein the first distance criterion is determined by a calculated distance between a first label and a second label in the probe.

90. The computer system of claim 88, wherein the instructions for identifying the plurality of labels applies a second distance criterion between a centroid of the second candidate label and a centroid of a third candidate label in the plurality of candidate labels.

91. The computer system of claim 90, wherein the second distance criterion is determined by a calculated distance between a second label and a third label in the probe.

92. The computer system of claim 90, wherein a value of the first distance criterion and a value of the second distance criterion contribute to determining whether the plurality of labels is said probe.

93. The computer system of claim 90, wherein the computer program mechanism further comprises a lookup table comprising a plurality of valid reporter sequences, wherein each valid reporter sequence in the plurality of valid reporter sequences comprises a first distance between a first pair of labels and a second distance between a second pair of labels, and wherein the probe identification module further comprises instructions for comparing the string sequence of the plurality of labels, the first distance criterion, and the second distance criterion, to valid reporter sequences in the lookup table.

94. The computer system of claim 83, wherein the instructions for identifying the plurality of labels applies an angle criterion to triplets of candidate labels in the plurality of candidate labels.

95. The computer system of claim 83, wherein the instructions for identifying the plurality of labels comprises instructions for applying a model to select candidate labels in the plurality of candidate labels.

96. The computer system of claim 95, wherein the instructions for applying a model to select candidate labels comprises instructions for applying linear regression to the select candidate labels.

97. The computer system of claim 95, wherein the label identification module further comprises instructions for verifying that a candidate label in the plurality of candidate labels satisfies a spot shape criterion.

98. The computer system of claim 97, wherein said spot shape criterion is a match between an observed spot shape of the candidate label and the theoretical point spread of the diffraction limited point source light determined by a magnification of the candidate label.

99. The computer system of claim 97, wherein the instructions for verifying that a candidate label in the plurality of candidate labels satisfies the spot shape criterion comprises instructions for performing point spread function modeling on the candidate label.

100. The computer system of claim 97, wherein the instructions for verifying that a candidate label in the plurality of candidate labels satisfies the spot shape criterion comprises instructions for applying a spot segmentation algorithm to the candidate label.

101. The computer system of claim 100, wherein the spot segmentation algorithm comprises a watershed transformation.

102. The computer system of claim 83, wherein the instructions for identifying the plurality of labels applies an absolute distance criterion between a centroid of a first terminal candidate label and a centroid of a second terminal candidate label in the plurality of candidate labels.

103. The computer system of claim 83, wherein the instructions for identifying the plurality of labels comprises instructions for identifying a buffer zone around a portion of the substrate that has select candidate labels in the plurality of candidate labels, wherein there are no candidate labels in the buffer zone.

104. The computer system of claim 66, wherein the plurality of labels are linearly arranged on the substrate.

105. The computer system of claim 66, wherein the plurality of labels are linearly arranged on the substrate in the same linear orientation.

106. The computer system of claim 66, wherein each respective label in the plurality of labels occupies between 4 and 20 pixels in a pixilated representation of the respective label in a light image in the plurality of light images.

107. The computer system of claim 66, wherein the label identification module further comprises:
instructions for identifying a first candidate label in the plurality of light images; and
instructions for identifying a second candidate label in the plurality of light images that is within a predetermined distance away from the first candidate label;
wherein the plurality of labels comprises the first candidate label and the second candidate label.

108. The computer system of claim 66, wherein the plurality of different wavelength ranges consists of between two different wavelength ranges and twenty different wavelength ranges.

109. The computer system of claim 66, wherein the plurality of labels consists of between two labels and twenty labels.

110. The computer system of claim 66, wherein a first subset of the labels in the string sequence error check an identity of the labels in a second subset of the labels in the string sequence.

111. The computer system of claim 66, wherein a first subset of labels in the string sequence are a checksum for a second subset of labels in the string sequence.

112. The computer system of claim 66, wherein
the label identification module comprises instructions for repeating said instructions for identifying a plurality of labels a plurality of times, wherein each time said instructions for identifying a plurality of labels is repeated, a different plurality of labels is identified, in the plurality of light images, that are proximate to each other on the substrate; and
wherein the probe identification module determines whether each said different plurality of labels identified by the label identification module comprises a valid reporter sequence, wherein for each said different plurality of labels, said probe identification module:
deems the different plurality of labels to be a probe when the string sequence of the different plurality of labels is confirmed as a valid reporter sequence; and
deems the different plurality of labels to not be a probe when the string sequence of the different plurality of labels is not confirmed as a valid reporter sequence.

113. The computer system of claim 112, wherein a plurality of probes is identified.

114. The computer system of claim 113 wherein said plurality of probes consists of three or more probes.

115. The computer system of claim 112, wherein said probe identification model stores each string sequence of each different plurality of labels that is not confirmed as a valid reporter sequence.

116. The computer system of claim 112, wherein said probe identification model stores each string sequence of each different plurality of labels that is confirmed as a valid reporter sequence.

117. A system for detecting the presence of a probe within a sample overlayed on a substrate, the system comprising:
a light measuring mechanism that measures a plurality of light images, each light image in the plurality of light images being for light received from the sample at a wavelength range in a plurality of different wavelength ranges;
a data storage module comprising instructions for storing said plurality of light images;
a label identification mechanism that identifies a plurality of labels in the plurality of light images that are proximate to each other on the substrate, wherein a spatial order of the plurality of labels determines a string sequence of the plurality of labels; and
a probe identification mechanism that determines whether the string sequence of the plurality of labels comprises a valid reporter sequence, wherein
when the string sequence of the plurality of labels is confirmed as a valid reporter sequence, the plurality of labels is deemed to be the probe; and
when the string sequence of the plurality of labels is not confirmed as a valid reporter sequence, the plurality of labels is deemed to not be the probe.

118. The system of claim 117, wherein a first label in the plurality of labels is associated with a first position on the substrate that emits light in a first wavelength range in the plurality of different wavelength ranges and a second label in the plurality of labels is associated with a second position on the substrate that emits light in a second wavelength range in the plurality of different wavelength ranges.

119. The system of claim 118, wherein a portion of the first wavelength range overlaps with a portion of the second wavelength range.

120. The system of claim 117, wherein the system further comprises an illumination mechanism that illuminates the substrate.

121. The system of claim 120, wherein the illumination mechanism comprises an excitation light source and a plurality of excitation filters, where each excitation filter in the plurality of excitation filters is used in a corresponding light image in the plurality of light images to confine the light source to a corresponding different spectral range when the corresponding light image is measured.

122. The system of claim 117, wherein the light measuring mechanism comprises a plurality of measurement wavelength filters, wherein each measurement wavelength filter in the plurality of measurement wavelength filters is used in a corresponding light image in the plurality of light images to reject light not within a corresponding spectral range.

123. The system of claim 117, wherein the light measuring mechanism comprises a photodetector that forms a detection signal in response to light emitted from the sample.

124. The system of claim 117, wherein the light measuring mechanism comprises a detector circuit addressed by the detection signal that measures light emitted from the sample overlayed on the substrate, the light measuring mechanism further comprising an electronic memory for storing a plurality of label positions, wherein each label position in the plurality of label positions represents a label and each label position in the plurality of label positions originates more than a threshold amount of light.

125. The system of claim 117, wherein the label identification mechanism identifies the plurality of labels that are proximate to each other from among the plurality of label positions stored in electronic memory.

126. The system of claim 117, wherein the label identification mechanism comprises instructions for identifying a plurality of candidate labels in the plurality of light images, and wherein the plurality of labels is a subset of the plurality of candidate labels.

127. The system of claim 126, wherein each candidate label in the plurality of candidate labels comprises a position on the substrate that emits more than a threshold amount of light in any one light image in the plurality of light images.

128. The system of claim 126, wherein the plurality of labels comprises a first candidate label that emits light in a first wavelength range in the plurality of different wavelength ranges and a second candidate label in the plurality of labels that emits light in a second wavelength range in the plurality of different wavelength ranges.

129. The system of claim 126, wherein the instructions for identifying the plurality of labels applies a first distance criterion between a centroid of a first candidate label and a centroid of a second candidate label in the plurality of candidate labels.

130. The system of claim 129, wherein the first distance criterion is determined by a calculated distance between a first label and a second label in the probe.

131. The system of claim 130, wherein the instructions for identifying the plurality of labels applies a second distance criterion between a centroid of the second candidate label and a centroid of a third candidate label in the plurality of candidate labels.

132. The system of claim 131, wherein the second distance criterion is determined by a calculated distance between a second label and a third label in the probe.

133. The system of claim 131, wherein the first distance criterion is the same as the second distance criterion.

134. The system of claim 131, wherein the first distance criterion is different from the second distance criterion.

135. The system of claim 131, wherein a value of the first distance criterion and a value of the second distance criterion contribute to determining whether the plurality of labels is said probe.

136. The system of claim 126, wherein the instructions for identifying the plurality of labels applies an angle criterion to triplets of candidate labels in the plurality of candidate labels.

137. The system of claim 126, wherein the instructions for identifying the plurality of labels comprises instructions for applying a model to select candidate labels in the plurality of candidate labels.

138. The system of claim 137, wherein the instructions for applying a model to select candidate labels comprises instructions for applying linear regression to the select candidate labels.

139. The system of claim 126, wherein the label identification module further comprises instructions for verifying that a candidate label in the plurality of candidate labels satisfies a spot shape criterion.

140. The system of claim 139, wherein said spot shape criterion is a match between an observed spot shape of the candidate label and the theoretical point spread of the diffraction limited point source light determined by a magnification of the candidate label.

141. The system of claim 139, wherein the instructions for verifying that a candidate label in the plurality of candidate labels satisfies the spot shape criterion comprises instructions for performing point spread function modeling on the candidate label.

142. The system of claim 139, wherein the instructions for verifying that a candidate label in the plurality of candidate labels satisfies the spot shape criterion comprises instructions for applying a spot segmentation algorithm to the candidate label.

143. The system of claim 142, wherein the spot segmentation algorithm comprises a watershed transformation.

144. The system of claim 117, wherein the plurality of labels are linearly arranged on the substrate.

145. The system of claim 144, wherein a linear orientation of the plurality of labels is predetermined.

146. The system of claim 144, wherein a linear orientation of the plurality of labels is determined by an application of an electrical current across said substrate.

147. The system of claim 144, wherein the probe within the sample is overlayed on the substrate at a random position on the substrate.

148. A method for detecting the presence of a probe within a sample overlayed on a substrate, wherein the probe comprises a plurality of spatially arranged labels, the method comprising:

identifying a plurality of labels, in a plurality of light images, that are proximate to each other on the substrate, wherein a spatial order of the plurality of labels determines a string sequence of the plurality of labels, wherein each light image in the plurality of light images is for light received from the sample at a wavelength range in a plurality of different wavelength ranges; and determining whether the string sequence of the plurality of labels comprises a valid reporter sequence, wherein when the string sequence of the plurality of labels is confirmed as a valid reporter sequence, the plurality of labels is deemed to be the probe; and when the string sequence of the plurality of labels is not confirmed as a valid reporter sequence, the plurality of labels is deemed to not be the probe.

149. The method of claim 148, where the determining step comprises comparing the string sequence of the plurality of labels to valid reporter sequences in a lookup table.

150. The method of claim 148, the method further comprising storing the string sequence of the plurality of labels that is not confirmed as a valid reporter sequence.

151. The method of claim 148, the method further comprising aligning a first light image to a second light image in the plurality of light images using a plurality of fiducials present on the substrate.

152. The method of claim 148, wherein
the step of identifying a plurality of labels is repeated a plurality of times, wherein each time said step of identifying a plurality of labels is repeated, a different plurality of labels is identified, in the plurality of light images, that are proximate to each other on the substrate; the method further comprising
determining whether each said different plurality of labels comprises a valid reporter sequence, wherein for each said different plurality of labels
the different plurality of labels is deemed to be a probe when the string sequence of the different plurality of labels is confirmed as a valid reporter sequence; and
the different plurality of labels is deemed to not be a probe when the string sequence of the different plurality of labels is not confirmed as a valid reporter sequence.

153. The method of claim 152, wherein a plurality of probes is identified.

154. The method of claim 152, wherein said plurality of probes consists of three or more probes.

155. The method of claim 152, wherein said plurality of probes consists of ten or more probes.

156. The method of claim 152, the method further comprising storing each type of probe identified.

157. The method of claim 152, wherein each string sequence of each different plurality of labels that is not confirmed as a valid reporter sequence is stored.

158. The method of claim 152, wherein each string sequence of each different plurality of labels that is confirmed as a valid reporter sequence is stored.

\* \* \* \* \*

```
                         SEQUENCE LISTING

<160> NUMBER OF SEQ ID NOS: 3

<210> SEQ ID NO 1
<211> LENGTH: 900
<212> TYPE: DNA
<213> ORGANISM: Artificial Sequence
<220> FEATURE:
<223> OTHER INFORMATION: Polynucleotide

<400> SEQUENCE: 1
gagctcggga gatggcgagc tggaagcatc agaaagtagg aagatgacaa aatagggcca      60
tagaagcatg aagaactgaa cgcatgagac aataggaagc tacgccacta gggacctgag     120
aagctgagcg gctcagcggg tccgagcgtc aaaaaataaa agagtgaaac aatagacgaa     180
tgacgcggta aaaccatcca gaagtaaacg ggtacaaaca tacagagata gccacctgga     240
ccaataggca cgtacaaacg tacaagcctg gcgcgatgag gcaatccaca cgtgcagagc     300
tggaacaatg gaaagatgca agaataaacc gataccggga tcgagggctc agcgaataaa     360
gcagtcaaca actggaaaga tccacacata ccggcgtaac cgagtccaaa catacagacc     420
tgcaagactc gcgacatggg acggtaaaac catccgaccg taaaccggta accaggtagc     480
cgggtaaaaa catagcaggg tggagacctc agaacgtaaa gacgtccaag ggtcgccgga     540
tagcgaacta cgcgcatcgc ccaatgggcc aatcaacaga taaacgagta gaaaagtcag     600
aaaataagaa actaacgaaa tacgagggtc caaggatgca agactgaggc cctaaggaga     660
taaggaaata ggccgatgca gacctgaaac gatgcaccga tccgacggta aaagactaga     720
cacgtagccg gatcagggcc tgggaggctg gaaccgtgag cacatagcaa agtcgcagcg     780
tcggcagatg cgccggtaaa aaagtagagg catgaccgga tgggcaaata gcgacgtaca     840
gcagtgaagc actaaaagca tccaagggta ggagactagg cgcctcgacg ggtaggtacc     900

<210> SEQ ID NO 2
<211> LENGTH: 60
<212> TYPE: DNA
<213> ORGANISM: Artificial Sequence
<220> FEATURE:
<223> OTHER INFORMATION: Oligonucleotide

<400> SEQUENCE: 2
gtctatcatc acagcgtcta tcatcacagc gtctatcatc acagcgtcta tcatcacagc      60

<210> SEQ ID NO 3
<211> LENGTH: 15
<212> TYPE: DNA
<213> ORGANISM: Artificial Sequence
<220> FEATURE:
<223> OTHER INFORMATION: Oligonucleotide

<400> SEQUENCE: 3
gctgtgatga tagac                                                       15
```